United States Patent
Sampath et al.

(10) Patent No.: US 11,887,728 B2
(45) Date of Patent: *Jan. 30, 2024

(54) INTELLIGENT MEDICAL ESCALATION PROCESS

(71) Applicant: MASIMO CORPORATION, Irvine, CA (US)

(72) Inventors: Anand Sampath, Corona, CA (US); Bilal Muhsin, San Clemente, CA (US)

(73) Assignee: Masimo Corporation, Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/061,495

(22) Filed: Oct. 1, 2020

(65) Prior Publication Data

US 2021/0027887 A1 Jan. 28, 2021

Related U.S. Application Data

(63) Continuation of application No. 15/498,194, filed on Apr. 26, 2017, now Pat. No. 10,833,983, which is a
(Continued)

(51) Int. Cl.
*G16H 40/67* (2018.01)
*H04L 45/00* (2022.01)
(Continued)

(52) U.S. Cl.
CPC .......... *G16H 40/67* (2018.01); *A61B 5/0022* (2013.01); *G08B 21/02* (2013.01); *G08B 29/20* (2013.01);
(Continued)

(58) Field of Classification Search
CPC ..... G06F 19/3418; G08B 21/02; G08B 29/20; G08B 25/005; G08B 29/16; A61B 5/0022;
(Continued)

(56) References Cited

U.S. PATENT DOCUMENTS 3,646,606 A 2/1972 Buxton et al.
3,690,313 A 9/1972 Weppner et al.
(Continued)

FOREIGN PATENT DOCUMENTS

CN 202889636 4/2013
EP 0 735 499 10/1996
(Continued)

OTHER PUBLICATIONS

US 8,845,543 B2, 09/2014, Diab et al. (withdrawn)
(Continued)

*Primary Examiner* — Shah M Rahman
(74) *Attorney, Agent, or Firm* — Knobbe Martens Olson & Bear LLP

(57) ABSTRACT

A medical network service can replace or supplement some or all of an expensive internally staffed clinical facility network with a cloud-based networking service. The medical network service in certain embodiments can provide networking services via software as a service technologies, platform as a service technologies, and/or infrastructure as a service technologies. The medical network service can provide these services to large existing clinical facilities such as metropolitan hospitals as well as to smaller clinical facilities such as specialized surgical centers. The medical network service can replace and/or supplement existing IT networks in hospitals and other clinical facilities and can therefore reduce costs and increase security and reliability of those networks. In addition, the medical network service can provide synergistic benefits that can improve patient outcomes and patient care. In addition, a medical edge router can provide redundant communications features for transmitting patient data to the medical network service.

20 Claims, 12 Drawing Sheets

Related U.S. Application Data continuation of application No. 14/030,360, filed on Sep. 18, 2013, now Pat. No. 9,749,232.

(60) Provisional application No. 61/738,362, filed on Dec. 17, 2012, provisional application No. 61/713,418, filed on Oct. 12, 2012, provisional application No. 61/703,643, filed on Sep. 20, 2012.

(51) Int. Cl.
*G08B 21/02* (2006.01)
*A61B 5/00* (2006.01)
*G08B 29/20* (2006.01)
*G08B 25/00* (2006.01)
*G08B 29/16* (2006.01)

(52) U.S. Cl.
CPC ............ *H04L 45/70* (2013.01); *G08B 25/005* (2013.01); *G08B 29/16* (2013.01)

(58) Field of Classification Search
CPC ...... A61B 5/0015; H04L 45/70; G16H 40/40; G16H 40/60; G16H 40/67
See application file for complete search history.

(56) References Cited

U.S. PATENT DOCUMENTS

| | | |
|---|---|---|
| 3,810,102 A | 5/1974 | Parks, III et al. |
| 3,815,583 A | 6/1974 | Scheidt |
| 3,972,320 A | 8/1976 | Kalman |
| 3,978,849 A | 9/1976 | Geneen |
| 4,108,166 A | 8/1978 | Schmid |
| 4,231,354 A | 11/1980 | Kurtz et al. |
| 4,589,415 A | 5/1986 | Haaga |
| 4,662,378 A | 5/1987 | Thomis |
| 4,827,943 A | 5/1989 | Bornn et al. |
| 4,838,275 A * | 6/1989 | Lee .................. A61B 5/7465 600/483 |
| 4,852,570 A | 8/1989 | Levine |
| 4,960,128 A | 10/1990 | Gordon et al. |
| 4,964,408 A | 10/1990 | Hink et al. |
| 5,041,187 A | 8/1991 | Hink et al. |
| 5,069,213 A | 12/1991 | Polczynski |
| 5,092,340 A | 3/1992 | Yamaguchi et al. |
| 5,140,519 A | 8/1992 | Friesdorf et al. |
| 5,159,932 A | 11/1992 | Zanetti et al. |
| 5,161,539 A | 11/1992 | Evans et al. |
| 5,163,438 A | 11/1992 | Gordon et al. |
| 5,262,944 A | 11/1993 | Weisner et al. |
| 5,277,189 A | 1/1994 | Jacobs |
| 5,278,627 A | 1/1994 | Aoyagi et al. |
| 5,282,474 A | 2/1994 | Valdes Sosa et al. |
| 5,296,688 A | 3/1994 | Hamilton et al. |
| 5,318,037 A | 6/1994 | Evans et al. |
| 5,319,355 A * | 6/1994 | Russek ............... A61B 5/0002 340/407.1 |
| 5,331,549 A | 7/1994 | Crawford, Jr. |
| 5,333,106 A | 7/1994 | Lanpher et al. |
| 5,337,744 A | 8/1994 | Branigan |
| 5,341,805 A | 8/1994 | Stavridi et al. |
| 5,348,008 A | 9/1994 | Bornn et al. |
| 5,358,519 A | 10/1994 | Grandjean |
| D353,195 S | 12/1994 | Savage et al. |
| D353,196 S | 12/1994 | Savage et al. |
| 5,375,599 A | 12/1994 | Shimizu |
| 5,375,604 A | 12/1994 | Kelly et al. |
| 5,377,676 A | 1/1995 | Vari et al. |
| 5,400,794 A | 3/1995 | Gorman |
| D357,982 S | 5/1995 | Dahl et al. |
| 5,416,695 A | 5/1995 | Stutman et al. |
| D359,546 S | 6/1995 | Savage et al. |
| 5,431,170 A | 7/1995 | Mathews |
| 5,434,611 A | 7/1995 | Tamura |
| 5,436,499 A | 7/1995 | Namavar et al. |
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,462,051 A | 10/1995 | Oka et al. |
| 5,479,934 A | 1/1996 | Imran |
| 5,482,036 A | 1/1996 | Diab et al. |
| 5,483,968 A | 1/1996 | Adam et al. |
| 5,490,505 A | 2/1996 | Diab et al. |
| 5,494,041 A | 2/1996 | Wilk |
| 5,494,043 A | 2/1996 | O'Sullivan et al. |
| 5,503,149 A | 4/1996 | Beavin |
| 5,505,202 A | 4/1996 | Mogi et al. |
| 5,533,511 A | 7/1996 | Kaspari et al. |
| 5,534,851 A | 7/1996 | Russek |
| 5,537,289 A | 7/1996 | Dahl |
| 5,544,649 A | 8/1996 | David et al. |
| 5,553,609 A | 9/1996 | Chen et al. |
| 5,558,638 A | 9/1996 | Evers et al. |
| 5,561,275 A | 10/1996 | Savage et al. |
| 5,562,002 A | 10/1996 | Lalin |
| 5,566,676 A | 10/1996 | Rosenfeldt et al. |
| 5,576,952 A | 11/1996 | Stutman et al. |
| 5,579,001 A | 11/1996 | Dempsey et al. |
| 5,590,649 A | 1/1997 | Caro et al. |
| 5,602,924 A | 2/1997 | Durand et al. |
| 5,619,991 A | 4/1997 | Sloane |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,640,967 A | 6/1997 | Fine et al. |
| 5,645,440 A | 7/1997 | Tobler et al. |
| 5,671,914 A | 9/1997 | Kalkhoran et al. |
| 5,685,299 A | 11/1997 | Diab et al. |
| 5,685,314 A | 11/1997 | Geheb et al. |
| 5,687,717 A | 11/1997 | Halpern et al. |
| 5,694,020 A | 12/1997 | Lang et al. |
| 5,724,580 A | 3/1998 | Levin et al. |
| 5,724,983 A | 3/1998 | Selker et al. |
| 5,725,308 A | 3/1998 | Smith et al. |
| 5,726,440 A | 3/1998 | Kalkhoran et al. |
| 5,734,739 A | 3/1998 | Sheehan et al. |
| D393,830 S | 4/1998 | Tobler et al. |
| 5,743,262 A | 4/1998 | Lepper, Jr. et al. |
| 5,747,806 A | 5/1998 | Khalil et al. |
| 5,750,994 A | 5/1998 | Schlager |
| 5,752,976 A * | 5/1998 | Duffin .................. G16H 40/67 607/32 |
| 5,754,111 A | 5/1998 | Garcia |
| 5,758,079 A | 5/1998 | Ludwig et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,772,585 A | 6/1998 | Lavin et al. |
| 5,782,757 A | 7/1998 | Diab et al. |
| 5,782,805 A | 7/1998 | Meinzer |
| 5,785,659 A | 7/1998 | Caro et al. |
| 5,791,347 A | 8/1998 | Flaherty et al. |
| 5,801,637 A | 9/1998 | Lomholt |
| 5,810,734 A | 9/1998 | Caro et al. |
| 5,813,403 A | 9/1998 | Soller et al. |
| 5,822,544 A | 10/1998 | Chaco et al. |
| 5,822,546 A | 10/1998 | George |
| 5,823,950 A | 10/1998 | Diab et al. |
| 5,829,723 A | 11/1998 | Brunner |
| 5,830,131 A | 11/1998 | Caro et al. |
| 5,833,618 A | 11/1998 | Caro et al. |
| 5,855,550 A | 1/1999 | Lai et al. |
| 5,860,919 A | 1/1999 | Kiani-Azarbayjany et al. |
| 5,876,351 A | 3/1999 | Rohde |
| 5,890,929 A | 4/1999 | Mills et al. |
| 5,904,654 A | 5/1999 | Wohltmann et al. |
| 5,910,139 A | 6/1999 | Cochran et al. |
| 5,919,134 A | 7/1999 | Diab |
| 5,921,920 A | 7/1999 | Marshall et al. |
| 5,924,074 A | 7/1999 | Evans |
| 5,931,160 A | 8/1999 | Gilmore et al. |
| 5,931,791 A | 8/1999 | Saltzstein et al. |

(56) References Cited

U.S. PATENT DOCUMENTS

| | | |
|---|---|---|
| 5,934,925 A | 8/1999 | Tobler et al. |
| 5,940,182 A | 8/1999 | Lepper, Jr. et al. |
| 5,942,986 A | 8/1999 | Shabot et al. |
| 5,951,469 A | 9/1999 | Yamaura |
| 5,987,343 A | 11/1999 | Kinast |
| 5,987,519 A | 11/1999 | Peifer et al. |
| 5,995,855 A | 11/1999 | Kiani et al. |
| 5,997,343 A | 12/1999 | Mills et al. |
| 6,002,952 A | 12/1999 | Diab et al. |
| 6,006,119 A | 12/1999 | Soller et al. |
| 6,010,937 A | 1/2000 | Karam et al. |
| 6,011,986 A | 1/2000 | Diab et al. |
| 6,014,346 A | 1/2000 | Malone |
| 6,018,673 A | 1/2000 | Chin et al. |
| 6,024,699 A | 2/2000 | Surwit et al. |
| 6,027,452 A | 2/2000 | Flaherty et al. |
| 6,032,678 A | 3/2000 | Rottem |
| 6,035,230 A | 3/2000 | Kang et al. |
| 6,036,642 A | 3/2000 | Diab et al. |
| 6,036,718 A | 3/2000 | Ledford et al. |
| 6,040,578 A | 3/2000 | Malin et al. |
| 6,045,509 A | 4/2000 | Caro et al. |
| 6,045,527 A | 4/2000 | Appelbaum et al. |
| 6,057,758 A | 5/2000 | Dempsey et al. |
| 6,066,204 A | 5/2000 | Haven |
| 6,067,462 A | 5/2000 | Diab et al. |
| 6,081,735 A | 6/2000 | Diab et al. |
| 6,088,607 A | 7/2000 | Diab et al. |
| 6,093,146 A | 7/2000 | Filangeri |
| 6,101,478 A | 8/2000 | Brown |
| 6,106,463 A | 8/2000 | Wilk |
| 6,110,522 A | 8/2000 | Lepper, Jr. et al. |
| 6,115,673 A | 9/2000 | Malin et al. |
| 6,124,597 A | 9/2000 | Shehada |
| 6,128,521 A | 10/2000 | Marro et al. |
| 6,129,675 A | 10/2000 | Jay |
| 6,132,218 A | 10/2000 | Benja-Athon |
| 6,139,494 A | 10/2000 | Cairnes |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,167,258 A | 12/2000 | Schmidt et al. |
| D437,058 S | 1/2001 | Gozani |
| 6,168,563 B1 | 1/2001 | Brown |
| 6,171,237 B1 | 1/2001 | Avitall et al. |
| 6,175,752 B1 | 1/2001 | Say et al. |
| 6,183,417 B1 | 2/2001 | Gehab et al. |
| 6,184,521 B1 | 2/2001 | Coffin, IV et al. |
| 6,185,448 B1 | 2/2001 | Borovsky |
| 6,195,576 B1 | 2/2001 | John |
| 6,206,830 B1 | 3/2001 | Diab et al. |
| 6,221,012 B1 | 4/2001 | Maschke et al. |
| 6,224,553 B1 | 5/2001 | Nevo |
| 6,229,856 B1 | 5/2001 | Diab et al. |
| 6,230,142 B1 | 5/2001 | Benigno et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,241,684 B1 | 6/2001 | Amano et al. |
| 6,251,113 B1 | 6/2001 | Appelbaum |
| 6,253,097 B1 | 6/2001 | Aronow et al. |
| 6,255,708 B1 | 7/2001 | Sudharsanan et al. |
| 6,256,523 B1 | 7/2001 | Diab et al. |
| 6,263,222 B1 | 7/2001 | Diab et al. |
| 6,267,723 B1 | 7/2001 | Matsumura et al. |
| 6,269,262 B1 | 7/2001 | Kandori et al. |
| 6,278,522 B1 | 8/2001 | Lepper, Jr. et al. |
| 6,280,213 B1 | 8/2001 | Tobler et al. |
| 6,280,381 B1 | 8/2001 | Malin et al. |
| 6,285,896 B1 | 9/2001 | Tobler et al. |
| 6,301,493 B1 | 10/2001 | Marro et al. |
| 6,304,767 B1 | 10/2001 | Soller et al. |
| 6,308,089 B1 | 10/2001 | von der Ruhr et al. |
| 6,312,378 B1 | 11/2001 | Bardy |
| 6,317,627 B1 | 11/2001 | Ennen et al. |
| 6,321,100 B1 | 11/2001 | Parker |
| 6,322,502 B1 | 11/2001 | Schoenberg et al. |
| 6,325,761 B1 | 12/2001 | Jay |
| 6,329,139 B1 | 12/2001 | Nova et al. |
| 6,332,100 B1 | 12/2001 | Sahai et al. |
| 6,334,065 B1 | 12/2001 | Al-Ali et al. |
| 6,338,039 B1 | 1/2002 | Lonski et al. |
| 6,343,224 B1 | 1/2002 | Parker |
| 6,349,228 B1 | 2/2002 | Kiani et al. |
| 6,352,504 B1 | 3/2002 | Ise |
| 6,354,235 B1 | 3/2002 | Davies |
| 6,360,114 B1 | 3/2002 | Diab et al. |
| 6,364,834 B1 | 4/2002 | Reuss et al. |
| 6,364,839 B1 | 4/2002 | Little et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,385,476 B1 | 5/2002 | Osadchy et al. |
| 6,385,589 B1 | 5/2002 | Trusheim et al. |
| 6,388,240 B2 | 5/2002 | Schulz et al. |
| 6,397,091 B2 | 5/2002 | Diab et al. |
| 6,406,426 B1 | 6/2002 | Reuss et al. |
| 6,407,335 B1 | 6/2002 | Franklin-Lees |
| 6,411,373 B1 | 6/2002 | Garside et al. |
| 6,415,167 B1 | 7/2002 | Blank et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,470,893 B1 | 10/2002 | Boesen |
| 6,480,505 B1 | 11/2002 | Johansson et al. |
| 6,487,429 B2 | 11/2002 | Hockersmith et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,516,289 B2 | 2/2003 | David et al. |
| 6,519,487 B1 | 2/2003 | Parker |
| 6,524,240 B1 | 2/2003 | Thede |
| 6,525,386 B1 | 2/2003 | Mills et al. |
| 6,526,300 B1 | 2/2003 | Kiani et al. |
| 6,534,012 B1 | 3/2003 | Hazen et al. |
| 6,541,756 B2 | 4/2003 | Schulz et al. |
| 6,542,764 B1 | 4/2003 | Al-Ali et al. |
| 6,544,173 B2 | 4/2003 | West et al. |
| 6,544,174 B2 | 4/2003 | West et al. |
| 6,551,243 B2 | 4/2003 | Bocionek et al. |
| 6,570,592 B1 | 5/2003 | Sajdak et al. |
| 6,578,428 B1 | 6/2003 | Dromms et al. |
| 6,580,086 B1 | 6/2003 | Schulz et al. |
| 6,584,336 B1 | 6/2003 | Ali et al. |
| 6,587,196 B1 | 7/2003 | Stippick et al. |
| 6,587,199 B1 | 7/2003 | Luu |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,616,606 B1 | 9/2003 | Peterson et al. |
| 6,632,181 B2 | 10/2003 | Flaherty et al. |
| 6,635,559 B2 | 10/2003 | Greenwald et al. |
| 6,639,668 B1 | 10/2003 | Trepagnier |
| 6,640,116 B2 | 10/2003 | Diab |
| 6,640,117 B2 | 10/2003 | Makarewicz et al. |
| 6,641,533 B2 | 11/2003 | Causey et al. |
| 6,643,530 B2 | 11/2003 | Diab et al. |
| 6,646,556 B1 | 11/2003 | Smith et al. |
| 6,650,917 B2 | 11/2003 | Diab et al. |
| 6,650,939 B2 | 11/2003 | Takpke, II et al. |
| 6,654,624 B2 | 11/2003 | Diab et al. |
| D483,872 S | 12/2003 | Cruz et al. |
| 6,658,276 B2 | 12/2003 | Kianl et al. |
| 6,661,161 B1 | 12/2003 | Lanzo et al. |
| 6,663,570 B2 | 12/2003 | Mott et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,694,180 B1 | 2/2004 | Boesen |

(56) References Cited

U.S. PATENT DOCUMENTS

| | | |
|---|---|---|
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,719,694 B2 | 4/2004 | Weng et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,725,086 B2 | 4/2004 | Marinello |
| 6,728,560 B2 | 4/2004 | Kollias et al. |
| 6,730,026 B2 | 5/2004 | Christ et al. |
| 6,735,459 B2 | 5/2004 | Parker |
| 6,738,652 B2 | 5/2004 | Mattu et al. |
| 6,745,060 B2 | 6/2004 | Diab et al. |
| 6,746,406 B2 | 6/2004 | Lia et al. |
| 6,750,463 B1 | 6/2004 | Riley |
| 6,751,492 B2 | 6/2004 | Ben-haim |
| 6,760,607 B2 | 7/2004 | Al-Ali |
| 6,766,188 B2 | 7/2004 | Soller |
| 6,770,028 B1 | 8/2004 | Ali et al. |
| 6,771,994 B2 | 8/2004 | Kiani et al. |
| 6,783,492 B2 | 8/2004 | Dominguez |
| 6,788,965 B2 | 9/2004 | Ruchti et al. |
| 6,790,178 B1 | 9/2004 | Mault et al. |
| 6,792,300 B1 | 9/2004 | Diab et al. |
| 6,795,724 B2 | 9/2004 | Hogan |
| 6,796,186 B2 | 9/2004 | Lia et al. |
| 6,804,656 B1 | 10/2004 | Rosenfeld |
| 6,807,050 B1 | 10/2004 | Whitehorn et al. |
| 6,813,511 B2 | 11/2004 | Diab et al. |
| 6,816,241 B2 | 11/2004 | Grubisic |
| 6,816,741 B2 | 11/2004 | Diab |
| 6,817,979 B2 | 11/2004 | Nihtila et al. |
| 6,822,564 B2 | 11/2004 | Al-Ali |
| 6,826,419 B2 | 11/2004 | Diab et al. |
| 6,830,711 B2 | 12/2004 | Mills et al. |
| 6,837,848 B2 | 1/2005 | Bonner et al. |
| 6,841,535 B2 | 1/2005 | Divita et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,855,112 B2 | 2/2005 | Kao et al. |
| 6,860,266 B2 | 3/2005 | Blike |
| 6,861,639 B2 | 3/2005 | Al-Ali |
| 6,876,931 B2 | 4/2005 | Lorenz et al. |
| 6,893,396 B2 | 5/2005 | Schulze et al. |
| 6,897,788 B2 | 5/2005 | Khair et al. |
| 6,898,452 B2 | 5/2005 | Al-Ali et al. |
| 6,907,237 B1 | 6/2005 | Dorenbosch et al. |
| 6,915,149 B2 | 7/2005 | Ben-haim |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,952,340 B2 | 10/2005 | Son et al. |
| 6,956,649 B2 | 10/2005 | Acosta et al. |
| 6,957,107 B2 | 10/2005 | Rogers et al. |
| 6,961,598 B2 | 11/2005 | Diab |
| 6,970,792 B1 | 11/2005 | Diab |
| 6,979,812 B2 | 12/2005 | Al-Ali |
| 6,980,419 B2 | 12/2005 | Smith et al. |
| 6,983,179 B2 | 1/2006 | Ben-haim |
| 6,985,764 B2 | 1/2006 | Mason et al. |
| 6,988,989 B2 | 1/2006 | Weiner et al. |
| 6,990,087 B2 | 1/2006 | Rao et al. |
| 6,990,364 B2 | 1/2006 | Ruchti et al. |
| 6,993,371 B2 | 1/2006 | Kiani et al. |
| 6,996,427 B2 | 2/2006 | Ali et al. |
| 6,997,884 B2 | 2/2006 | Ulmsten |
| 6,998,247 B2 | 2/2006 | Monfre et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,025,729 B2 | 4/2006 | de Chazal et al. |
| 7,027,849 B2 | 4/2006 | Al-Ali |
| 7,030,749 B2 | 4/2006 | Al-Ali |
| 7,033,761 B2 | 4/2006 | Shafer |
| 7,035,686 B2 | 4/2006 | Hogan |
| 7,039,449 B2 | 5/2006 | Al-Ali |
| 7,041,060 B2 | 5/2006 | Flaherty et al. |
| 7,042,338 B1 | 5/2006 | Weber |
| 7,044,918 B2 | 5/2006 | Diab |
| 7,044,930 B2 | 5/2006 | Stromberg |
| 7,048,687 B1 | 5/2006 | Reuss et al. |
| 7,063,666 B2 | 6/2006 | Weng et al. |
| 7,067,893 B2 | 6/2006 | Mills et al. |
| 7,079,035 B2 | 7/2006 | Bock et al. |
| D526,719 S | 8/2006 | Richie, Jr. et al. |
| 7,096,052 B2 | 8/2006 | Mason et al. |
| 7,096,054 B2 | 8/2006 | Abdul-Hafiz et al. |
| D529,616 S | 10/2006 | Deros et al. |
| 7,132,641 B2 | 11/2006 | Schulz et al. |
| 7,133,710 B2 | 11/2006 | Acosta et al. |
| 7,142,901 B2 | 11/2006 | Kiani et al. |
| 7,149,561 B2 | 12/2006 | Diab |
| 7,186,966 B2 | 3/2007 | Al-Ali |
| 7,188,621 B2 | 3/2007 | DeVries et al. |
| 7,190,261 B2 | 3/2007 | Al-Ali |
| 7,208,119 B1 | 4/2007 | Kurtock et al. |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,229,415 B2 | 6/2007 | Schwartz |
| 7,239,905 B2 | 7/2007 | Kiani-Azarbayjany et al. |
| 7,241,287 B2 | 7/2007 | Shehada et al. |
| 7,244,251 B2 | 7/2007 | Shehada et al. |
| 7,245,373 B2 | 7/2007 | Soller et al. |
| 7,245,953 B1 | 7/2007 | Parker |
| 7,252,659 B2 | 8/2007 | Shehada et al. |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,256,708 B2 | 8/2007 | Rosenfeld |
| 7,261,691 B1 | 8/2007 | Asomani |
| 7,261,697 B2 | 8/2007 | Berstein |
| 7,264,616 B2 | 9/2007 | Shehada et al. |
| 7,267,671 B2 | 9/2007 | Shehada et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,285,090 B2 | 10/2007 | Stivoric et al. |
| 7,289,835 B2 | 10/2007 | Mansfield et al. |
| 7,292,141 B2 | 11/2007 | Staats et al. |
| 7,292,883 B2 | 11/2007 | De Felice et al. |
| 7,295,866 B2 | 11/2007 | Al-Ali |
| 7,307,543 B2 | 12/2007 | Rosenfeld |
| 7,313,423 B2 | 12/2007 | Griffin et al. |
| 7,314,446 B2 | 1/2008 | Byrd et al. |
| 7,315,825 B2 | 1/2008 | Rosenfeld |
| 7,321,862 B2 | 1/2008 | Rosenfeld |
| 7,322,971 B2 | 1/2008 | Shehada et al. |
| 7,327,219 B2 | 2/2008 | Lederer |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,178 B2 | 4/2008 | Ziel et al. |
| 7,356,365 B2 | 4/2008 | Schurman |
| 7,371,981 B2 | 5/2008 | Abdul-Hafiz |

(56) References Cited

U.S. PATENT DOCUMENTS

| | | |
|---|---|---|
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al Ali et al. |
| 7,377,899 B2 | 5/2008 | Weber et al. |
| 7,378,975 B1 | 5/2008 | Smith et al. |
| 7,382,247 B2 | 6/2008 | Welch et al. |
| 7,383,070 B2 | 6/2008 | Diab et al. |
| 7,390,299 B2 | 6/2008 | Weiner et al. |
| 7,395,158 B2 | 7/2008 | Monfre et al. |
| 7,395,216 B2 | 7/2008 | Rosenfeld |
| 7,402,338 B2 | 7/2008 | Weintritt |
| 7,411,509 B2 | 8/2008 | Rosenfeld |
| 7,413,546 B2 | 8/2008 | Agutter et al. |
| 7,415,297 B2 | 8/2008 | Al-Ali et al. |
| 7,419,483 B2 | 9/2008 | Shehada |
| 7,428,432 B2 | 9/2008 | Ali et al. |
| 7,433,827 B2 | 10/2008 | Rosenfeld |
| 7,438,683 B2 | 10/2008 | Al-Ali et al. |
| 7,439,856 B2 | 10/2008 | Weiner et al. |
| 7,440,787 B2 | 10/2008 | Diab |
| 7,454,240 B2 | 11/2008 | Diab et al. |
| 7,454,359 B2 | 11/2008 | Rosenfeld |
| 7,454,360 B2 | 11/2008 | Rosenfeld |
| 7,462,151 B2 | 12/2008 | Childre et al. |
| 7,467,002 B2 | 12/2008 | Weber et al. |
| 7,467,094 B2 | 12/2008 | Rosenfeld |
| 7,469,157 B2 | 12/2008 | Diab et al. |
| 7,471,969 B2 | 12/2008 | Diab et al. |
| 7,471,971 B2 | 12/2008 | Diab et al. |
| 7,475,019 B2 | 1/2009 | Rosenfeld |
| 7,483,729 B2 | 1/2009 | Al-Ali et al. |
| 7,483,730 B2 | 1/2009 | Diab et al. |
| 7,489,250 B2 | 2/2009 | Bock et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,497,828 B1 | 3/2009 | Wilk et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,514,725 B2 | 4/2009 | Wojtczuk et al. |
| 7,515,043 B2 | 4/2009 | Welch et al. |
| 7,515,044 B2 | 4/2009 | Welch et al. |
| 7,519,406 B2 | 4/2009 | Blank et al. |
| 7,523,044 B2 | 4/2009 | Rosenblood |
| 7,526,328 B2 | 4/2009 | Diab et al. |
| D592,507 S | 5/2009 | Wachman et al. |
| 7,530,942 B1 | 5/2009 | Diab |
| 7,530,949 B2 | 5/2009 | Al Ali et al. |
| 7,530,955 B2 | 5/2009 | Diab et al. |
| 7,532,919 B2 | 5/2009 | Soyemi et al. |
| 7,549,961 B1 | 6/2009 | Hwang |
| 7,551,717 B2 | 6/2009 | Tome et al. |
| 7,559,520 B2 | 7/2009 | Quijano et al. |
| 7,563,110 B2 | 7/2009 | Al-Ali et al. |
| 7,577,475 B2 | 8/2009 | Consentino et al. |
| 7,590,950 B2 | 9/2009 | Collins et al. |
| 7,593,230 B2 | 9/2009 | Abul-Haj et al. |
| 7,596,398 B2 | 9/2009 | Al-Ali et al. |
| 7,597,665 B2 | 10/2009 | Wilk et al. |
| 7,606,608 B2 | 10/2009 | Blank et al. |
| 7,612,999 B2 | 11/2009 | Clark et al. |
| 7,616,303 B2 | 11/2009 | Yang et al. |
| 7,618,375 B2 | 11/2009 | Flaherty |
| 7,620,674 B2 | 11/2009 | Ruchti et al. |
| D606,659 S | 12/2009 | Kiani et al. |
| 7,629,039 B2 | 12/2009 | Eckerbom et al. |
| 7,639,145 B2 | 12/2009 | Lawson et al. |
| 7,640,140 B2 | 12/2009 | Ruchti et al. |
| 7,647,083 B2 | 1/2010 | Al-Ali et al. |
| 7,650,291 B2 | 1/2010 | Rosenfeld |
| D609,193 S | 2/2010 | Al-Ali et al. |
| 7,654,966 B2 | 2/2010 | Westinskow et al. |
| 7,671,733 B2 | 3/2010 | McNeal et al. |
| 7,684,845 B2 | 3/2010 | Juan |
| 7,689,437 B1 | 3/2010 | Teller et al. |
| RE41,236 E | 4/2010 | Seely |
| D614,305 S | 4/2010 | Al-Ali et al. |
| 7,693,697 B2 | 4/2010 | Westinskow et al. |
| 7,697,966 B2 | 4/2010 | Monfre et al. |
| 7,698,105 B2 | 4/2010 | Ruchti et al. |
| RE41,317 E | 5/2010 | Parker |
| RE41,333 E | 5/2010 | Blank et al. |
| 7,722,542 B2 | 5/2010 | Lia et al. |
| 7,729,733 B2 | 6/2010 | Al-Ali et al. |
| 7,734,320 B2 | 6/2010 | Al-Ali |
| 7,736,318 B2 | 6/2010 | Consentino et al. |
| 7,740,590 B2 | 6/2010 | Bernstein |
| 7,749,164 B2 | 7/2010 | Davis |
| 7,761,127 B2 | 7/2010 | Al-Ali et al. |
| 7,761,128 B2 | 7/2010 | Al-Ali et al. |
| 7,763,420 B2 | 7/2010 | Strizker et al. |
| 7,764,982 B2 | 7/2010 | Dalke et al. |
| D621,515 S | 8/2010 | Chua et al. |
| D621,516 S | 8/2010 | Kiani et al. |
| 7,766,818 B2 | 8/2010 | Iketani et al. |
| 7,774,060 B2 | 8/2010 | Westenskow et al. |
| 7,778,851 B2 | 8/2010 | Schoenberg et al. |
| 7,791,155 B2 | 9/2010 | Diab |
| 7,794,407 B2 | 9/2010 | Rothenberg |
| 7,801,581 B2 | 9/2010 | Diab |
| 7,806,830 B2 | 10/2010 | Bernstein |
| 7,820,184 B2 | 10/2010 | Strizker et al. |
| 7,822,452 B2 | 10/2010 | Schurman et al. |
| RE41,912 E | 11/2010 | Parker |
| 7,831,450 B2 | 11/2010 | Schoenberg |
| 7,841,986 B2 | 11/2010 | He et al. |
| 7,844,313 B2 | 11/2010 | Kiani et al. |
| 7,844,314 B2 | 11/2010 | Al-Ali |
| 7,844,315 B2 | 11/2010 | Al-Ali |
| 7,848,935 B2 | 12/2010 | Gotlib |
| 7,858,322 B2 | 12/2010 | Tymianski et al. |
| 7,865,222 B2 | 1/2011 | Weber et al. |
| 7,865,232 B1 | 1/2011 | Krishnaswamy et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,881,892 B2 | 2/2011 | Soyemi et al. |
| 7,884,314 B2 | 2/2011 | Hamada |
| 7,890,156 B2 | 2/2011 | Ooi et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,914,514 B2 | 3/2011 | Calderon |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,942,844 B2 | 5/2011 | Moberg et al. |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,963,927 B2 | 6/2011 | Kelleher et al. |
| 7,967,749 B2 | 6/2011 | Hutchinson et al. |
| 7,976,472 B2 | 7/2011 | Kiani |
| 7,978,062 B2 | 7/2011 | LaLonde et al. |
| 7,988,637 B2 | 8/2011 | Diab |
| 7,988,639 B2 | 8/2011 | Starks |
| 7,990,382 B2 | 8/2011 | Kiani |
| 7,991,446 B2 | 8/2011 | Al-Ali et al. |
| 7,991,463 B2 | 8/2011 | Kelleher et al. |
| 7,991,625 B2 * | 8/2011 | Rosenfeld ............ G08B 21/182 |
| | | 600/300 |

(56) References Cited

U.S. PATENT DOCUMENTS

| | | |
|---|---|---|
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,027,846 B2 | 9/2011 | Schoenberg |
| 8,028,701 B2 | 10/2011 | Al-Ali et al. |
| 8,029,765 B2 | 10/2011 | Bellott et al. |
| 8,033,996 B2 | 10/2011 | Behar |
| 8,036,727 B2 | 10/2011 | Schurman et al. |
| 8,036,728 B2 | 10/2011 | Diab et al. |
| 8,036,736 B2 | 10/2011 | Snyder et al. |
| 8,038,625 B2 | 10/2011 | Afonso et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| 8,068,104 B2 | 11/2011 | Rampersad |
| 8,073,707 B2 | 12/2011 | Teller et al. |
| 8,094,013 B1 | 1/2012 | Lee et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| D659,836 S | 5/2012 | Bensch et al. |
| 8,170,887 B2 | 5/2012 | Rosenfeld |
| 8,175,672 B2 | 5/2012 | Parker |
| 8,175,895 B2 | 5/2012 | Rosenfeld |
| 8,180,420 B2 | 5/2012 | Diab et al. |
| 8,180,650 B2 | 5/2012 | Graves et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,200,308 B2 | 6/2012 | Zhang et al. |
| 8,203,438 B2 | 6/2012 | Kiani et al. |
| 8,203,704 B2 | 6/2012 | Merritt et al. |
| 8,204,566 B2 | 6/2012 | Schurman et al. |
| 8,206,312 B2 | 6/2012 | Farquhar |
| 8,214,007 B2 | 7/2012 | Baker et al. |
| 8,219,172 B2 | 7/2012 | Schurman et al. |
| 8,224,411 B2 | 7/2012 | Al-Ali et al. |
| 8,224,667 B1 * | 7/2012 | Miller ............... G16H 40/67 600/300 |
| 8,228,181 B2 | 7/2012 | Al-Ali |
| 8,229,532 B2 | 7/2012 | Davis |
| 8,229,533 B2 | 7/2012 | Diab et al. |
| 8,233,955 B2 | 7/2012 | Al-Ali et al. |
| 8,235,907 B2 | 8/2012 | Wilk et al. |
| 8,239,780 B2 | 8/2012 | Manetta et al. |
| 8,241,213 B2 | 8/2012 | Lynn et al. |
| 8,244,325 B2 | 8/2012 | Al-Ali et al. |
| 8,249,815 B2 | 8/2012 | Taylor |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,274,360 B2 | 9/2012 | Sampath et al. |
| 8,280,473 B2 | 10/2012 | Al-Ali |
| 8,294,588 B2 | 10/2012 | Fisher et al. |
| 8,294,716 B2 | 10/2012 | Lord et al. |
| 8,298,153 B2 | 10/2012 | Boute et al. |
| 8,301,217 B2 | 10/2012 | Al-Ali et al. |
| 8,306,596 B2 | 11/2012 | Schurman et al. |
| 8,310,336 B2 | 11/2012 | Muhsin et al. |
| 8,311,747 B2 | 11/2012 | Taylor |
| 8,311,748 B2 | 11/2012 | Taylor et al. |
| 8,315,683 B2 | 11/2012 | Al-Ali et al. |
| 8,315,812 B2 | 11/2012 | Taylor |
| 8,315,813 B2 | 11/2012 | Taylor et al. |
| 8,315,814 B2 | 11/2012 | Taylor et al. |
| 8,321,150 B2 | 11/2012 | Taylor |
| RE43,860 E | 12/2012 | Parker |
| 8,326,649 B2 | 12/2012 | Rosenfeld |
| 8,327,002 B1 | 12/2012 | Van Dussen et al. |
| 8,328,793 B2 | 12/2012 | Birkenbach et al. |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,360,936 B2 | 1/2013 | Dibenedetto et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,995 B2 | 2/2013 | Al-Ali et al. |
| 8,385,996 B2 | 2/2013 | Smith et al. |
| D679,018 S | 3/2013 | Fullerton et al. |
| 8,388,353 B2 | 3/2013 | Kiani |
| 8,399,822 B2 | 3/2013 | Al-Ali |
| 8,401,602 B2 | 3/2013 | Kiani |
| 8,401,874 B2 | 3/2013 | Rosenfeld |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,423,378 B1 * | 4/2013 | Goldberg ............... G16H 40/67 705/2 |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellot et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,167 B2 | 7/2013 | Buxton et al. |
| 8,489,364 B2 | 7/2013 | Weber et al. |
| 8,498,684 B2 | 7/2013 | Weber et al. |
| 8,504,128 B2 | 8/2013 | Blank et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,549 B2 | 10/2013 | Schurman et al. |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 8,565,847 B2 | 10/2013 | Buxton et al. |
| 8,570,167 B2 | 10/2013 | Al-Ali |
| 8,570,503 B2 | 10/2013 | Vo et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,578,082 B2 | 11/2013 | Medina et al. |
| 8,579,813 B2 | 11/2013 | Causey, III et al. |
| 8,581,732 B2 | 11/2013 | Al-Ali et al. |
| 8,584,345 B2 | 11/2013 | Al-Ali et al. |
| 8,588,880 B2 | 11/2013 | Abdul-Hafiz et al. |
| 8,588,924 B2 | 11/2013 | Dion |
| 8,597,287 B2 | 12/2013 | Benamou et al. |
| 8,600,467 B2 | 12/2013 | Al-Ali et al. |
| 8,600,777 B2 | 12/2013 | Schoenberg |
| 8,606,342 B2 | 12/2013 | Diab |
| 8,612,260 B2 | 12/2013 | Hasan et al. |
| 8,620,678 B2 | 12/2013 | Gotlib |
| 8,626,255 B2 | 1/2014 | Al-Ali et al. |
| 8,630,691 B2 | 1/2014 | Lamego et al. |
| 8,634,889 B2 | 1/2014 | Al-Ali et al. |
| 8,641,631 B2 | 2/2014 | Sierra et al. |
| 8,652,060 B2 | 2/2014 | Al-Ali |

(56) References Cited

U.S. PATENT DOCUMENTS

| | | |
|---|---|---|
| 8,655,680 B2 | 2/2014 | Bechtel et al. |
| 8,663,107 B2 | 3/2014 | Kiani |
| 8,666,468 B1 | 3/2014 | Al-Ali |
| 8,667,967 B2 | 3/2014 | Al-Ali et al. |
| 8,670,811 B2 | 3/2014 | O'Reilly |
| 8,670,814 B2 | 3/2014 | Diab et al. |
| 8,676,286 B2 | 3/2014 | Weber et al. |
| 8,682,407 B2 | 3/2014 | Al-Ali |
| RE44,823 E | 4/2014 | Parker |
| RE44,875 E | 4/2014 | Kiani et al. |
| 8,688,183 B2 | 4/2014 | Bruinsma et al. |
| 8,690,771 B2 | 4/2014 | Wekell et al. |
| 8,690,799 B2 | 4/2014 | Telfort et al. |
| 8,694,331 B2 | 4/2014 | DeBelser et al. |
| 8,700,112 B2 | 4/2014 | Kiani |
| 8,702,627 B2 | 4/2014 | Telfort et al. |
| 8,706,179 B2 | 4/2014 | Parker |
| 8,712,494 B1 | 4/2014 | MacNeish, III et al. |
| 8,715,206 B2 | 5/2014 | Telfort et al. |
| 8,717,909 B1 | 5/2014 | Shekhar et al. |
| 8,718,735 B2 | 5/2014 | Lamego et al. |
| 8,718,737 B2 | 5/2014 | Diab et al. |
| 8,718,738 B2 | 5/2014 | Blank et al. |
| 8,720,249 B2 | 5/2014 | Al-Ali |
| 8,721,541 B2 | 5/2014 | Al-Ali et al. |
| 8,721,542 B2 | 5/2014 | Al-Ali et al. |
| 8,723,677 B1 | 5/2014 | Kiani |
| 8,740,792 B1 | 6/2014 | Kiani et al. |
| 8,754,776 B2 | 6/2014 | Poeze et al. |
| 8,755,535 B2 | 6/2014 | Telfort et al. |
| 8,755,856 B2 | 6/2014 | Diab et al. |
| 8,755,872 B1 | 6/2014 | Marinow |
| 8,758,020 B2 | 6/2014 | Burdea et al. |
| 8,761,850 B2 | 6/2014 | Lamego |
| D709,846 S | 7/2014 | Oswaks |
| 8,764,671 B2 | 7/2014 | Kiani |
| 8,768,423 B2 | 7/2014 | Shakespeare et al. |
| 8,771,204 B2 | 7/2014 | Telfort et al. |
| 8,777,634 B2 | 7/2014 | Kiani et al. |
| 8,781,543 B2 | 7/2014 | Diab et al. |
| 8,781,544 B2 | 7/2014 | Al-Ali et al. |
| 8,781,549 B2 | 7/2014 | Al-Ali et al. |
| 8,788,003 B2 | 7/2014 | Schurman et al. |
| 8,790,268 B2 | 7/2014 | Al-Ali |
| 8,792,950 B2 | 7/2014 | Larsen et al. |
| 8,801,613 B2 | 8/2014 | Al-Ali et al. |
| 8,818,477 B2 | 8/2014 | Soller |
| 8,821,397 B2 | 9/2014 | Al-Ali et al. |
| 8,821,415 B2 | 9/2014 | Al-Ali et al. |
| 8,830,054 B2 | 9/2014 | Weiss |
| 8,830,449 B1 | 9/2014 | Lamego et al. |
| 8,831,700 B2 | 9/2014 | Schurman et al. |
| 8,840,549 B2 | 9/2014 | Al-Ali et al. |
| 8,847,740 B2 | 9/2014 | Kiani et al. |
| 8,849,365 B2 | 9/2014 | Smith et al. |
| 8,852,094 B2 | 10/2014 | Al-Ali et al. |
| 8,852,994 B2 | 10/2014 | Wojtczuk et al. |
| 8,866,620 B2 | 10/2014 | Amir |
| 8,868,147 B2 | 10/2014 | Stippick et al. |
| 8,868,150 B2 | 10/2014 | Al-Ali et al. |
| 8,870,792 B2 | 10/2014 | Al-Ali et al. |
| 8,873,035 B2 | 10/2014 | Yang et al. |
| 8,878,888 B2 | 11/2014 | Rosenfeld |
| 8,886,271 B2 | 11/2014 | Kiani et al. |
| 8,888,539 B2 | 11/2014 | Al-Ali et al. |
| 8,888,708 B2 | 11/2014 | Diab et al. |
| 8,892,180 B2 | 11/2014 | Weber et al. |
| 8,897,847 B2 | 11/2014 | Al-Ali |
| 8,907,287 B2 | 12/2014 | Vanderpohl |
| 8,909,310 B2 | 12/2014 | Lamego et al. |
| 8,909,330 B2 | 12/2014 | McCombie et al. |
| 8,911,377 B2 | 12/2014 | Al-Ali |
| 8,912,909 B2 | 12/2014 | Al-Ali et al. |
| 8,920,317 B2 | 12/2014 | Al-Ali et al. |
| 8,921,699 B2 | 12/2014 | Al-Ali et al. |
| 8,922,382 B2 | 12/2014 | Al-Ali et al. |
| 8,929,964 B2 | 1/2015 | Al-Ali et al. |
| 8,942,777 B2 | 1/2015 | Diab et al. |
| 8,948,834 B2 | 2/2015 | Diab et al. |
| 8,948,835 B2 | 2/2015 | Diab |
| 8,951,248 B2 | 2/2015 | Messerly et al. |
| 8,956,292 B2 | 2/2015 | Wekell et al. |
| 8,956,294 B2 | 2/2015 | McCombie et al. |
| 8,965,471 B2 | 2/2015 | Lamego |
| 8,983,564 B2 | 3/2015 | Al-Ali |
| 8,989,831 B2 | 3/2015 | Al-Ali et al. |
| 8,996,085 B2 | 3/2015 | Kiani et al. |
| 8,998,809 B2 | 4/2015 | Kiani |
| 8,998,830 B2 | 4/2015 | Halperin et al. |
| 9,028,429 B2 | 5/2015 | Telfort et al. |
| 9,037,207 B2 | 5/2015 | Al-Ali et al. |
| 9,041,530 B2 | 5/2015 | Sprigg et al. |
| 9,057,689 B2 | 6/2015 | Soller |
| 9,058,635 B1 | 6/2015 | Rybkin |
| 9,060,721 B2 | 6/2015 | Reichgott et al. |
| 9,066,666 B2 | 6/2015 | Kiani |
| 9,066,680 B1 | 6/2015 | Al-Ali et al. |
| 9,072,474 B2 | 7/2015 | Al-Ali et al. |
| 9,078,560 B2 | 7/2015 | Schurman et al. |
| 9,084,569 B2 | 7/2015 | Weber et al. |
| 9,095,291 B2 | 8/2015 | Soller |
| 9,095,316 B2 | 8/2015 | Welch et al. |
| 9,104,789 B2 | 8/2015 | Gross et al. |
| 9,106,038 B2 | 8/2015 | Telfort et al. |
| 9,107,625 B2 | 8/2015 | Telfort et al. |
| 9,107,626 B2 | 8/2015 | Al-Ali et al. |
| 9,113,831 B2 | 8/2015 | Al-Ali |
| 9,113,832 B2 | 8/2015 | Al-Ali |
| 9,119,595 B2 | 9/2015 | Lamego |
| 9,125,578 B2 | 9/2015 | Grunwald |
| 9,131,881 B2 | 9/2015 | Diab et al. |
| 9,131,882 B2 | 9/2015 | Al-Ali et al. |
| 9,131,883 B2 | 9/2015 | Al-Ali |
| 9,131,917 B2 | 9/2015 | Telfort et al. |
| 9,138,180 B1 | 9/2015 | Coverston et al. |
| 9,138,182 B2 | 9/2015 | Al-Ali et al. |
| 9,138,192 B2 | 9/2015 | Weber et al. |
| 9,142,117 B2 | 9/2015 | Muhsin et al. |
| 9,153,112 B1 | 10/2015 | Kiani et al. |
| 9,153,121 B2 | 10/2015 | Kiani et al. |
| 9,161,696 B2 | 10/2015 | Al-Ali et al. |
| 9,161,713 B2 | 10/2015 | Al-Ali et al. |
| 9,167,995 B2 | 10/2015 | Lamego et al. |
| 9,176,141 B2 | 11/2015 | Al-Ali et al. |
| 9,186,102 B2 | 11/2015 | Bruinsma et al. |
| 9,192,312 B2 | 11/2015 | Al-Ali |
| 9,192,329 B2 | 11/2015 | Al-Ali |
| 9,192,351 B1 | 11/2015 | Telfort et al. |
| 9,195,385 B2 | 11/2015 | Al-Ali et al. |
| D745,167 S | 12/2015 | Canas et al. |
| 9,211,072 B2 | 12/2015 | Kiani |
| 9,211,095 B1 | 12/2015 | Al-Ali |
| 9,218,454 B2 | 12/2015 | Kiani et al. |
| 9,226,696 B2 | 1/2016 | Kiani |
| 9,241,662 B2 | 1/2016 | Al-Ali et al. |
| 9,245,668 B1 | 1/2016 | Vo et al. |
| 9,259,185 B2 | 2/2016 | Abdul-Hafiz et al. |
| 9,262,586 B2 | 2/2016 | Steiger et al. |
| 9,267,572 B2 | 2/2016 | Barker et al. |
| 9,277,880 B2 | 3/2016 | Poeze et al. |
| 9,289,167 B2 | 3/2016 | Diab et al. |
| 9,295,421 B2 | 3/2016 | Kiani et al. |
| 9,307,928 B1 | 4/2016 | Al-Ali et al. |
| 9,323,894 B2 | 4/2016 | Kiani |
| D755,392 S | 5/2016 | Hwang et al. |
| 9,326,712 B1 | 5/2016 | Kiani |
| 9,333,316 B2 | 5/2016 | Kiani |
| 9,339,220 B2 | 5/2016 | Lamego et al. |
| 9,341,565 B2 | 5/2016 | Lamego et al. |
| 9,351,673 B2 | 5/2016 | Diab et al. |
| 9,351,675 B2 | 5/2016 | Al-Ali et al. |
| 9,364,181 B2 | 6/2016 | Kiani et al. |
| 9,368,671 B2 | 6/2016 | Wojtczuk et al. |
| 9,370,325 B2 | 6/2016 | Al-Ali et al. |

(56) References Cited

U.S. PATENT DOCUMENTS

| | | |
|---|---|---|
| 9,370,326 B2 | 6/2016 | McHale et al. |
| 9,370,335 B2 | 6/2016 | Al-ali et al. |
| 9,375,185 B2 | 6/2016 | Ali et al. |
| 9,384,652 B2 | 7/2016 | Gilham et al. |
| 9,386,953 B2 | 7/2016 | Al-Ali |
| 9,386,961 B2 | 7/2016 | Al-Ali et al. |
| 9,392,945 B2 | 7/2016 | Al-Ali et al. |
| 9,397,448 B2 | 7/2016 | Al-Ali et al. |
| 9,408,542 B1 | 8/2016 | Kinast et al. |
| 9,436,645 B2 | 9/2016 | Al-Ali et al. |
| 9,445,759 B1 | 9/2016 | Lamego et al. |
| 9,466,919 B2 | 10/2016 | Kiani et al. |
| 9,474,474 B2 | 10/2016 | Lamego et al. |
| 9,480,422 B2 | 11/2016 | Al-Ali |
| 9,480,435 B2 | 11/2016 | Olsen |
| 9,492,110 B2 | 11/2016 | Al-Ali et al. |
| 9,510,779 B2 | 12/2016 | Poeze et al. |
| 9,517,024 B2 | 12/2016 | Kiani et al. |
| 9,529,762 B2 | 12/2016 | Gisler et al. |
| 9,532,722 B2 | 1/2017 | Lamego et al. |
| 9,538,949 B2 | 1/2017 | Al-Ali et al. |
| 9,538,980 B2 | 1/2017 | Telfort et al. |
| 9,549,696 B2 | 1/2017 | Lamego et al. |
| 9,554,737 B2 | 1/2017 | Schurman et al. |
| 9,560,996 B2 | 2/2017 | Kiani |
| 9,560,998 B2 | 2/2017 | Al-Ali et al. |
| 9,566,019 B2 | 2/2017 | Al-Ali et al. |
| 9,579,039 B2 | 2/2017 | Jansen et al. |
| 9,591,975 B2 | 3/2017 | Dalvi et al. |
| 9,622,692 B2 | 4/2017 | Lamego et al. |
| 9,622,693 B2 | 4/2017 | Diab |
| D788,312 S | 5/2017 | Al-Ali et al. |
| 9,636,055 B2 | 5/2017 | Al-Ali et al. |
| 9,636,056 B2 | 5/2017 | Al-Ali |
| 9,649,054 B2 | 5/2017 | Lamego et al. |
| 9,662,052 B2 | 5/2017 | Al-Ali et al. |
| 9,668,679 B2 | 6/2017 | Schurman et al. |
| 9,668,680 B2 | 6/2017 | Bruinsma et al. |
| 9,668,703 B2 | 6/2017 | Al-Ali |
| 9,675,286 B2 | 6/2017 | Diab |
| 9,687,160 B2 | 6/2017 | Kiani |
| 9,693,719 B2 | 7/2017 | Al-Ali et al. |
| 9,693,737 B2 | 7/2017 | Al-Ali |
| 9,697,928 B2 | 7/2017 | Al-Ali et al. |
| 9,717,425 B2 | 8/2017 | Kiani et al. |
| 9,717,458 B2 | 8/2017 | Lamego et al. |
| 9,724,016 B1 | 8/2017 | Al-Ali et al. |
| 9,724,024 B2 | 8/2017 | Al-Ali |
| 9,724,025 B1 | 8/2017 | Kiani et al. |
| 9,730,640 B2 | 8/2017 | Diab et al. |
| 9,743,887 B2 | 8/2017 | Al-Ali et al. |
| 9,749,232 B2 | 8/2017 | Sampath et al. |
| 9,750,442 B2 | 9/2017 | Olsen |
| 9,750,443 B2 | 9/2017 | Smith et al. |
| 9,750,461 B1 | 9/2017 | Telfort |
| 9,775,545 B2 | 10/2017 | Al-Ali et al. |
| 9,775,546 B2 | 10/2017 | Diab et al. |
| 9,775,570 B2 | 10/2017 | Al-Ali |
| 9,778,079 B1 | 10/2017 | Al-Ali et al. |
| 9,782,077 B2 | 10/2017 | Lamego et al. |
| 9,782,110 B2 | 10/2017 | Kiani |
| 9,787,568 B2 | 10/2017 | Lamego et al. |
| 9,788,735 B2 | 10/2017 | Al-Ali |
| 9,788,768 B2 | 10/2017 | Al-Ali et al. |
| 9,795,300 B2 | 10/2017 | Al-Ali |
| 9,795,310 B2 | 10/2017 | Al-Ali |
| 9,795,358 B2 | 10/2017 | Telfort et al. |
| 9,795,739 B2 | 10/2017 | Al-Ali et al. |
| 9,801,556 B2 | 10/2017 | Kiani |
| 9,801,588 B2 | 10/2017 | Weber et al. |
| 9,808,188 B1 | 11/2017 | Perea et al. |
| 9,814,418 B2 | 11/2017 | Weber et al. |
| 9,820,691 B2 | 11/2017 | Kiani |
| 9,833,152 B2 | 12/2017 | Kiani et al. |
| 9,833,180 B2 | 12/2017 | Shakespeare et al. |
| 9,839,379 B2 | 12/2017 | Al-Ali et al. |
| 9,839,381 B1 | 12/2017 | Weber et al. |
| 9,847,002 B2 | 12/2017 | Kiani et al. |
| 9,847,749 B2 | 12/2017 | Kiani et al. |
| 9,848,800 B1 | 12/2017 | Lee et al. |
| 9,848,806 B2 | 12/2017 | Al-Ali et al. |
| 9,848,807 B2 | 12/2017 | Lamego |
| 9,861,298 B2 | 1/2018 | Eckerbom et al. |
| 9,861,304 B2 | 1/2018 | Al-Ali et al. |
| 9,861,305 B1 | 1/2018 | Weber et al. |
| 9,867,578 B2 | 1/2018 | Al-Ali et al. |
| 9,872,623 B2 | 1/2018 | Al-Ali |
| 9,876,320 B2 | 1/2018 | Coverston et al. |
| 9,877,650 B2 | 1/2018 | Muhsin et al. |
| 9,877,686 B2 | 1/2018 | Al-Ali et al. |
| 9,891,079 B2 | 2/2018 | Dalvi |
| 9,895,107 B2 | 2/2018 | Al-Ali et al. |
| 9,924,897 B1 | 3/2018 | Abdul-Hafiz |
| 9,936,917 B2 | 4/2018 | Poeze et al. |
| 9,955,937 B2 | 5/2018 | Telfort |
| 9,965,946 B2 | 5/2018 | Al-Ali et al. |
| D820,865 S | 6/2018 | Muhsin et al. |
| 9,986,952 B2 | 6/2018 | Dalvi et al. |
| D822,215 S | 7/2018 | Al-Ali et al. |
| D822,216 S | 7/2018 | Barker et al. |
| 10,010,276 B2 | 7/2018 | Al-Ali et al. |
| 10,086,138 B1 | 10/2018 | Novak, Jr. |
| 10,111,591 B2 | 10/2018 | Dyell et al. |
| D833,624 S | 11/2018 | DeJong et al. |
| 10,123,729 B2 | 11/2018 | Dyell et al. |
| D835,282 S | 12/2018 | Barker et al. |
| D835,283 S | 12/2018 | Barker et al. |
| D835,284 S | 12/2018 | Barker et al. |
| D835,285 S | 12/2018 | Barker et al. |
| 10,149,616 B2 | 12/2018 | Al-Ali et al. |
| 10,154,815 B2 | 12/2018 | Al-Ali et al. |
| 10,159,412 B2 | 12/2018 | Lamego et al. |
| 10,188,348 B2 | 1/2019 | Kiani et al. |
| RE47,218 E | 2/2019 | Ali-Ali |
| RE47,244 E | 2/2019 | Kiani et al. |
| RE47,249 E | 2/2019 | Kiani et al. |
| 10,205,291 B2 | 2/2019 | Scruggs et al. |
| 10,226,187 B2 | 3/2019 | Al-Ali et al. |
| 10,231,657 B2 | 3/2019 | Al-Ali et al. |
| 10,231,670 B2 | 3/2019 | Blank et al. |
| RE47,353 E | 4/2019 | Kiani et al. |
| 10,279,247 B2 | 5/2019 | Kiani |
| 10,292,664 B2 | 5/2019 | Al-Ali |
| 10,299,720 B2 | 5/2019 | Brown et al. |
| 10,327,337 B2 | 6/2019 | Triman et al. |
| 10,327,713 B2 | 6/2019 | Barker et al. |
| 10,332,630 B2 | 6/2019 | Al-Ali |
| 10,383,520 B2 | 8/2019 | Wojtczuk et al. |
| 10,383,527 B2 | 8/2019 | Al-Ali |
| 10,388,120 B2 | 8/2019 | Muhsin et al. |
| D864,120 S | 10/2019 | Forrest et al. |
| 10,441,181 B1 | 10/2019 | Telfort et al. |
| 10,441,196 B2 | 10/2019 | Eckerbom et al. |
| 10,448,844 B2 | 10/2019 | Al-Ali et al. |
| 10,448,871 B2 | 10/2019 | Al-Ali |
| 10,456,038 B2 | 10/2019 | Lamego et al. |
| 10,463,340 B2 | 11/2019 | Telfort et al. |
| 10,471,159 B1 | 11/2019 | Lapotko et al. |
| 10,505,311 B2 | 12/2019 | Al-Ali et al. |
| 10,524,738 B2 | 1/2020 | Olsen |
| 10,532,174 B2 | 1/2020 | Al-Ali |
| 10,537,285 B2 | 1/2020 | Sherim et al. |
| 10,542,903 B2 | 1/2020 | Al-Ali et al. |
| 10,555,678 B2 | 2/2020 | Dalvi et al. |
| 10,568,553 B2 | 2/2020 | O'Neil et al. |
| RE47,882 E | 3/2020 | Al-Ali |
| 10,608,817 B2 | 3/2020 | Haider et al. |
| D880,477 S | 4/2020 | Forrest et al. |
| 10,617,302 B2 | 4/2020 | Al-Ali et al. |
| 10,617,335 B2 | 4/2020 | Al-Ali et al. |
| 10,637,181 B2 | 4/2020 | Al-Ali et al. |
| D886,849 S | 6/2020 | Muhsin et al. |
| D887,548 S | 6/2020 | Abdul-Hafiz et al. |
| D887,549 S | 6/2020 | Abdul-Hafiz et al. |

(56) References Cited

U.S. PATENT DOCUMENTS

| | | |
|---|---|---|
| 10,667,764 B2 | 6/2020 | Ahmed et al. |
| D890,708 S | 7/2020 | Forrest et al. |
| 10,721,785 B2 | 7/2020 | Al-Ali |
| 10,736,518 B2 | 8/2020 | Al-Ali et al. |
| 10,750,984 B2 | 8/2020 | Pauley et al. |
| D897,098 S | 9/2020 | Al-Ali |
| 10,779,098 B2 | 9/2020 | Iswanto et al. |
| 10,827,961 B1 | 11/2020 | Iyengar et al. |
| 10,828,007 B1 | 11/2020 | Telfort et al. |
| 10,832,818 B2 | 11/2020 | Muhsin et al. |
| 10,833,983 B2 | 11/2020 | Sampath et al. |
| 10,849,554 B2 | 12/2020 | Shreim et al. |
| 10,856,750 B2 | 12/2020 | Indorf |
| D906,970 S | 1/2021 | Forrest et al. |
| D908,213 S | 1/2021 | Abdul-Hafiz et al. |
| 10,918,281 B2 | 2/2021 | Al-Ali et al. |
| 10,932,705 B2 | 3/2021 | Muhsin et al. |
| 10,932,729 B2 | 3/2021 | Kiani et al. |
| 10,939,878 B2 | 3/2021 | Kiani et al. |
| 10,956,950 B2 | 3/2021 | Al-Ali et al. |
| D916,135 S | 4/2021 | Indorf et al. |
| D917,046 S | 4/2021 | Abdul-Hafiz et al. |
| D917,550 S | 4/2021 | Indorf et al. |
| D917,564 S | 4/2021 | Indorf et al. |
| D917,704 S | 4/2021 | Al-Ali et al. |
| 10,987,066 B2 | 4/2021 | Chandran et al. |
| 10,991,135 B2 | 4/2021 | Al-Ali et al. |
| D919,094 S | 5/2021 | Al-Ali et al. |
| D919,100 S | 5/2021 | Al-Ali et al. |
| 11,006,867 B2 | 5/2021 | Al-Ali |
| D921,202 S | 6/2021 | Al-Ali et al. |
| 11,024,064 B2 | 6/2021 | Muhsin et al. |
| 11,026,604 B2 | 6/2021 | Chen et al. |
| D925,597 S | 7/2021 | Chandran et al. |
| D927,699 S | 8/2021 | Al-Ali et al. |
| 11,076,777 B2 | 8/2021 | Lee et al. |
| 11,114,188 B2 | 9/2021 | Poeze et al. |
| D933,232 S | 10/2021 | Al-Ali et al. |
| D933,233 S | 10/2021 | Al-Ali et al. |
| D933,234 S | 10/2021 | Al-Ali et al. |
| 11,145,408 B2 | 10/2021 | Sampath et al. |
| 11,147,518 B1 | 10/2021 | Al-Ali et al. |
| 11,185,262 B2 | 11/2021 | Al-Ali et al. |
| 11,191,484 B2 | 12/2021 | Kiani et al. |
| D946,596 S | 3/2022 | Ahmed |
| D946,597 S | 3/2022 | Ahmed |
| D946,598 S | 3/2022 | Ahmed |
| D946,617 S | 3/2022 | Ahmed |
| 11,272,839 B2 | 3/2022 | Al-Ali et al. |
| 11,289,199 B2 | 3/2022 | Al-Ali |
| RE49,034 E | 4/2022 | Al-Ali |
| 11,298,021 B2 | 4/2022 | Muhsin et al. |
| D950,580 S | 5/2022 | Ahmed |
| D950,599 S | 5/2022 | Ahmed |
| D950,738 S | 5/2022 | Al-Ali et al. |
| D957,648 S | 7/2022 | Al-Ali |
| 11,382,567 B2 | 7/2022 | O'Brien et al. |
| 11,389,093 B2 | 7/2022 | Triman et al. |
| 11,406,286 B2 | 8/2022 | Al-Ali et al. |
| 11,417,426 B2 | 8/2022 | Muhsin et al. |
| 11,439,329 B2 | 9/2022 | Lamego |
| 11,445,948 B2 | 9/2022 | Scruggs et al. |
| D965,789 S | 10/2022 | Al-Ali et al. |
| D967,433 S | 10/2022 | Al-Ali et al. |
| 11,464,410 B2 | 10/2022 | Muhsin |
| 11,504,058 B1 | 11/2022 | Sharma et al. |
| 11,504,066 B1 | 11/2022 | Dalvi et al. |
| D971,933 S | 12/2022 | Ahmed |
| D973,072 S | 12/2022 | Ahmed |
| D973,685 S | 12/2022 | Ahmed |
| D973,686 S | 12/2022 | Ahmed |
| D974,193 S | 1/2023 | Forrest et al. |
| D979,516 S | 2/2023 | Al-Ali et al. |
| D980,091 S | 3/2023 | Forrest et al. |
| 11,596,363 B2 | 3/2023 | Lamego |
| 11,627,919 B2 | 4/2023 | Kiani et al. |
| 11,637,437 B2 | 4/2023 | Al-Ali et al. |
| D985,498 S | 5/2023 | Al-Ali et al. |
| 11,653,862 B2 | 5/2023 | Dalvi et al. |
| D989,112 S | 6/2023 | Muhsin et al. |
| 11,678,829 B2 | 6/2023 | Al-Ali et al. |
| 11,692,934 B2 | 7/2023 | Normand et al. |
| 2001/0011355 A1 | 8/2001 | Kawai |
| 2001/0031922 A1 | 10/2001 | Weng et al. |
| 2001/0034477 A1 | 10/2001 | Mansfield et al. |
| 2001/0039483 A1 | 11/2001 | Brand et al. |
| 2001/0046366 A1 | 11/2001 | Susskind |
| 2001/0051765 A1 | 12/2001 | Walker et al. |
| 2002/0010401 A1 | 1/2002 | Bushmakin et al. |
| 2002/0038392 A1 | 3/2002 | De La Huerga |
| 2002/0045836 A1 | 4/2002 | Alkawwas |
| 2002/0052311 A1 | 5/2002 | Solomon et al. |
| 2002/0058864 A1 | 5/2002 | Mansfield et al. |
| 2002/0062230 A1 | 5/2002 | Morag et al. |
| 2002/0063690 A1 | 5/2002 | Chung et al. |
| 2002/0099275 A1 | 7/2002 | Schmidt et al. |
| 2002/0133080 A1 | 9/2002 | Apruzzese et al. |
| 2002/0140675 A1 | 10/2002 | Ali et al. |
| 2002/0177758 A1 | 11/2002 | Schoenberg |
| 2002/0198445 A1 | 12/2002 | Dominguez et al. |
| 2003/0013975 A1 | 1/2003 | Kiani |
| 2003/0018243 A1 | 1/2003 | Gerhardt et al. |
| 2003/0027326 A1 | 2/2003 | Ulmsten et al. |
| 2003/0036683 A1 | 2/2003 | Kehr et al. |
| 2003/0052787 A1 | 3/2003 | Zerhusen et al. |
| 2003/0058838 A1 | 3/2003 | Wengrovitz |
| 2003/0144582 A1 | 7/2003 | Cohen et al. |
| 2003/0149598 A1 | 8/2003 | Santoso et al. |
| 2003/0156288 A1 | 8/2003 | Barnum et al. |
| 2003/0158466 A1 | 8/2003 | Lynn et al. |
| 2003/0172940 A1 | 9/2003 | Rogers et al. |
| 2003/0212312 A1 | 11/2003 | Coffin, IV et al. |
| 2003/0216670 A1 | 11/2003 | Beggs |
| 2004/0013647 A1 | 1/2004 | Solomon et al. |
| 2004/0059599 A1 | 3/2004 | McIvor |
| 2004/0106163 A1 | 6/2004 | Workman, Jr. et al. |
| 2004/0122787 A1 | 6/2004 | Avinash et al. |
| 2004/0126007 A1 | 7/2004 | Ziel et al. |
| 2004/0139571 A1 | 7/2004 | Chang et al. |
| 2004/0147818 A1 | 7/2004 | Levy et al. |
| 2004/0172222 A1 | 9/2004 | Simpson et al. |
| 2004/0172302 A1 | 9/2004 | Martucci et al. |
| 2004/0186357 A1 | 9/2004 | Soderberg et al. |
| 2004/0230118 A1 | 11/2004 | Shehada et al. |
| 2004/0230132 A1 | 11/2004 | Shehada et al. |
| 2004/0230179 A1 | 11/2004 | Shehada et al. |
| 2004/0243017 A1 | 12/2004 | Causevic |
| 2004/0249670 A1 | 12/2004 | Noguchi et al. |
| 2004/0254431 A1 | 12/2004 | Shehada et al. |
| 2004/0254432 A1 | 12/2004 | Shehada et al. |
| 2004/0267103 A1 | 12/2004 | Li et al. |
| 2005/0020918 A1 | 1/2005 | Wilk et al. |
| 2005/0038332 A1 | 2/2005 | Saidara et al. |
| 2005/0038680 A1 | 2/2005 | McMahon |
| 2005/0055242 A1 | 3/2005 | Bello et al. |
| 2005/0055244 A1 | 3/2005 | Mullan et al. |
| 2005/0055276 A1 | 3/2005 | Kiani et al. |
| 2005/0080336 A1 | 4/2005 | Byrd et al. |
| 2005/0096542 A1 | 5/2005 | Weng et al. |
| 2005/0113653 A1 | 5/2005 | Fox et al. |
| 2005/0124864 A1 | 6/2005 | Mack et al. |
| 2005/0125256 A1 | 6/2005 | Schoenberg |
| 2005/0143671 A1 | 6/2005 | Hastings et al. |
| 2005/0146431 A1 | 7/2005 | Hastings et al. |
| 2005/0148890 A1 | 7/2005 | Hastings |
| 2005/0164933 A1 | 7/2005 | Tymianski et al. |
| 2005/0190747 A1 | 9/2005 | Sindhwani et al. |
| 2005/0191294 A1 | 9/2005 | Arap et al. |
| 2005/0203775 A1 | 9/2005 | Achan |
| 2005/0234317 A1 | 10/2005 | Kiani |
| 2005/0268401 A1 | 12/2005 | Dixon et al. |
| 2005/0277872 A1 | 12/2005 | Colby, Jr. et al. |
| 2006/0049936 A1 | 3/2006 | Collins, Jr. et al. |
| 2006/0058647 A1 | 3/2006 | Strommer et al. |

(56) References Cited

U.S. PATENT DOCUMENTS

| | | |
|---|---|---|
| 2006/0073719 A1 | 4/2006 | Kiani |
| 2006/0089543 A1 | 4/2006 | Kim et al. |
| 2006/0094936 A1 | 5/2006 | Russ |
| 2006/0149393 A1 | 7/2006 | Calderon |
| 2006/0155175 A1 | 7/2006 | Ogino et al. |
| 2006/0161054 A1 | 7/2006 | Reuss et al. |
| 2006/0169773 A1 | 8/2006 | Lyons et al. |
| 2006/0189871 A1 | 8/2006 | Al-Ali et al. |
| 2006/0190833 A1 | 8/2006 | SanGiovanni et al. |
| 2006/0200009 A1 | 9/2006 | Wekell et al. |
| 2006/0217684 A1 | 9/2006 | Shehada et al. |
| 2006/0217685 A1 | 9/2006 | Shehada et al. |
| 2006/0224413 A1 | 10/2006 | Kim et al. |
| 2006/0235300 A1 | 10/2006 | Weng et al. |
| 2006/0253042 A1 | 11/2006 | Stahmann et al. |
| 2007/0000490 A1 | 1/2007 | DeVries et al. |
| 2007/0002533 A1 | 1/2007 | Kogan et al. |
| 2007/0021675 A1 | 1/2007 | Childre et al. |
| 2007/0027368 A1 | 2/2007 | Collins et al. |
| 2007/0032733 A1 | 2/2007 | Burton et al. |
| 2007/0055116 A1 | 3/2007 | Clark et al. |
| 2007/0055544 A1 | 3/2007 | Jung et al. |
| 2007/0060798 A1 | 3/2007 | Krupnik et al. |
| 2007/0073116 A1 | 3/2007 | Kiani et al. |
| 2007/0073555 A1* | 3/2007 | Buist .............. G16H 40/20 600/300 |
| 2007/0088406 A1 | 4/2007 | Bennett et al. |
| 2007/0096897 A1 | 5/2007 | Weiner |
| 2007/0100222 A1 | 5/2007 | Mastrototaro et al. |
| 2007/0118399 A1 | 5/2007 | Avinash et al. |
| 2007/0140475 A1 | 6/2007 | Kurtock et al. |
| 2007/0156033 A1 | 7/2007 | Causey et al. |
| 2007/0157285 A1 | 7/2007 | Frank et al. |
| 2007/0159332 A1 | 7/2007 | Koblasz |
| 2007/0163589 A1 | 7/2007 | DeVries et al. |
| 2007/0180140 A1 | 8/2007 | Welch et al. |
| 2007/0185390 A1 | 8/2007 | Perkins et al. |
| 2007/0185739 A1 | 8/2007 | Ober et al. |
| 2007/0192140 A1 | 8/2007 | Gropper |
| 2007/0213600 A1 | 9/2007 | John et al. |
| 2007/0232941 A1 | 10/2007 | Rabinovich |
| 2007/0244377 A1 | 10/2007 | Cozad et al. |
| 2007/0244724 A1 | 10/2007 | Pendergast et al. |
| 2007/0254593 A1 | 11/2007 | Jollota et al. |
| 2007/0255114 A1 | 11/2007 | Ackermann et al. |
| 2007/0255116 A1 | 11/2007 | Mehta et al. |
| 2007/0255250 A1 | 11/2007 | Moberg et al. |
| 2007/0282478 A1 | 12/2007 | Al-Ali et al. |
| 2008/0000479 A1 | 1/2008 | Elaz et al. |
| 2008/0001735 A1 | 1/2008 | Tran |
| 2008/0003200 A1 | 1/2008 | Arap et al. |
| 2008/0015903 A1 | 1/2008 | Rodgers |
| 2008/0021854 A1 | 1/2008 | Jung et al. |
| 2008/0033661 A1 | 2/2008 | Syroid et al. |
| 2008/0039701 A1 | 2/2008 | Ali et al. |
| 2008/0053438 A1 | 3/2008 | DeVries et al. |
| 2008/0058657 A1 | 3/2008 | Schwartz et al. |
| 2008/0064965 A1 | 3/2008 | Jay et al. |
| 2008/0090626 A1 | 4/2008 | Griffin et al. |
| 2008/0091089 A1 | 4/2008 | Guillory et al. |
| 2008/0091090 A1 | 4/2008 | Guillory et al. |
| 2008/0091471 A1 | 4/2008 | Michon et al. |
| 2008/0094228 A1 | 4/2008 | Welch et al. |
| 2008/0097167 A1 | 4/2008 | Yudkovitch et al. |
| 2008/0099366 A1 | 5/2008 | Niemiec et al. |
| 2008/0119412 A1 | 5/2008 | Tymianski et al. |
| 2008/0138278 A1 | 6/2008 | Scherz et al. |
| 2008/0169922 A1 | 7/2008 | Issokson |
| 2008/0171919 A1 | 7/2008 | Stivoric et al. |
| 2008/0188795 A1 | 8/2008 | Katz et al. |
| 2008/0194918 A1 | 8/2008 | Kulik et al. |
| 2008/0201174 A1 | 8/2008 | Ramasubramanian et al. |
| 2008/0208912 A1 | 8/2008 | Garibaldi |
| 2008/0221396 A1 | 9/2008 | Garces et al. |
| 2008/0221418 A1 | 9/2008 | Al-Ali et al. |
| 2008/0228077 A1 | 9/2008 | Wilk et al. |
| 2008/0249804 A1 | 10/2008 | Kim |
| 2008/0275309 A1 | 11/2008 | Stivoric et al. |
| 2008/0281167 A1 | 11/2008 | Soderberg et al. |
| 2008/0281168 A1 | 11/2008 | Gibson et al. |
| 2008/0281181 A1 | 11/2008 | Manzione et al. |
| 2008/0287751 A1 | 11/2008 | Stivoric et al. |
| 2008/0292172 A1 | 11/2008 | Assmann et al. |
| 2008/0300020 A1 | 12/2008 | Nishizawa et al. |
| 2008/0319275 A1 | 12/2008 | Chiu et al. |
| 2008/0319354 A1 | 12/2008 | Bell et al. |
| 2009/0005651 A1 | 1/2009 | Ward et al. |
| 2009/0018808 A1 | 1/2009 | Bronstein et al. |
| 2009/0024008 A1 | 1/2009 | Brunner et al. |
| 2009/0036759 A1 | 2/2009 | Ault et al. |
| 2009/0043172 A1 | 2/2009 | Zagorchev et al. |
| 2009/0046837 A1 | 2/2009 | Thiel |
| 2009/0052623 A1 | 2/2009 | Tome et al. |
| 2009/0054735 A1 | 2/2009 | Higgins et al. |
| 2009/0054743 A1 | 2/2009 | Wekell et al. |
| 2009/0062682 A1 | 3/2009 | Bland et al. |
| 2009/0069642 A1 | 3/2009 | Gao et al. |
| 2009/0093687 A1 | 4/2009 | Telfort et al. |
| 2009/0095926 A1 | 4/2009 | MacNeish, III |
| 2009/0099480 A1 | 4/2009 | Salgo et al. |
| 2009/0119330 A1 | 5/2009 | Sampath et al. |
| 2009/0119843 A1 | 5/2009 | Rodgers et al. |
| 2009/0124867 A1 | 5/2009 | Hirsch et al. |
| 2009/0131759 A1 | 5/2009 | Sims et al. |
| 2009/0143832 A1 | 6/2009 | Saba |
| 2009/0146822 A1* | 6/2009 | Soliman .............. A61B 5/0002 705/3 |
| 2009/0157058 A1 | 6/2009 | Ferren et al. |
| 2009/0164236 A1* | 6/2009 | Gounares .............. G16H 40/20 705/2 |
| 2009/0171170 A1 | 7/2009 | Li et al. |
| 2009/0171225 A1 | 7/2009 | Gadodia et al. |
| 2009/0177090 A1 | 7/2009 | Grunwald et al. |
| 2009/0182287 A1 | 7/2009 | Kassab |
| 2009/0204977 A1 | 8/2009 | Tavares et al. |
| 2009/0221880 A1 | 9/2009 | Soderberg et al. |
| 2009/0226372 A1 | 9/2009 | Ruoslahti et al. |
| 2009/0247984 A1 | 10/2009 | Lamego et al. |
| 2009/0264778 A1 | 10/2009 | Markowitz et al. |
| 2009/0275813 A1 | 11/2009 | Davis |
| 2009/0275844 A1 | 11/2009 | Al-Ali |
| 2009/0281462 A1 | 11/2009 | Heliot et al. |
| 2009/0299157 A1 | 12/2009 | Telfort et al. |
| 2009/0309755 A1 | 12/2009 | Williamson |
| 2009/0322540 A1 | 12/2009 | Richardson et al. |
| 2010/0004518 A1 | 1/2010 | Vo et al. |
| 2010/0030040 A1 | 2/2010 | Poeze et al. |
| 2010/0030094 A1 | 2/2010 | Lundback |
| 2010/0036209 A1 | 2/2010 | Ferren et al. |
| 2010/0069725 A1 | 3/2010 | Al-Ali |
| 2010/0088120 A1* | 4/2010 | Gonzalvo .............. G06Q 10/10 705/14.39 |
| 2010/0088121 A1 | 4/2010 | Shih et al. |
| 2010/0099964 A1 | 4/2010 | O'Reilly et al. |
| 2010/0125217 A1 | 5/2010 | Kuo et al. |
| 2010/0144627 A1 | 6/2010 | Vitek et al. |
| 2010/0185101 A1 | 7/2010 | Sakai et al. |
| 2010/0188230 A1 | 7/2010 | Lindsay |
| 2010/0198622 A1 | 8/2010 | Gajic et al. |
| 2010/0210958 A1 | 8/2010 | Manwaring et al. |
| 2010/0234718 A1 | 9/2010 | Sampath et al. |
| 2010/0270257 A1 | 10/2010 | Wachman et al. |
| 2010/0298650 A1 | 11/2010 | Moon et al. |
| 2010/0298659 A1 | 11/2010 | McCombie et al. |
| 2010/0298661 A1 | 11/2010 | McCombie et al. |
| 2010/0298742 A1 | 11/2010 | Perlman et al. |
| 2010/0305412 A1 | 12/2010 | Darrah et al. |
| 2010/0312103 A1 | 12/2010 | Gorek et al. |
| 2010/0317936 A1 | 12/2010 | Al-Ali et al. |
| 2010/0317951 A1 | 12/2010 | Rutkowski et al. |
| 2011/0001605 A1 | 1/2011 | Kiani et al. |
| 2011/0021930 A1 | 1/2011 | Mazzeo et al. |
| 2011/0023130 A1 | 1/2011 | Gudgel et al. |
| 2011/0028806 A1 | 2/2011 | Merritt et al. |

(56) References Cited

U.S. PATENT DOCUMENTS

| | | |
|---|---|---|
| 2011/0028809 A1 | 2/2011 | Goodman |
| 2011/0040197 A1 | 2/2011 | Welch et al. |
| 2011/0046495 A1 | 2/2011 | Osypka |
| 2011/0066051 A1 | 3/2011 | Moon et al. |
| 2011/0077473 A1 | 3/2011 | Lisogurski |
| 2011/0077488 A1 | 3/2011 | Buxton et al. |
| 2011/0078596 A1 | 3/2011 | Rawlins et al. |
| 2011/0080294 A1 | 4/2011 | Tanishima et al. |
| 2011/0082711 A1 | 4/2011 | Poeze et al. |
| 2011/0087081 A1 | 4/2011 | Kiani et al. |
| 2011/0087083 A1 | 4/2011 | Poeze et al. |
| 2011/0087084 A1 | 4/2011 | Jeong et al. |
| 2011/0087117 A1 | 4/2011 | Tremper et al. |
| 2011/0087756 A1 | 4/2011 | Biondi |
| 2011/0098583 A1 | 4/2011 | Pandia et al. |
| 2011/0105854 A1 | 5/2011 | Kiani et al. |
| 2011/0105956 A1 | 5/2011 | Hirth |
| 2011/0106561 A1 | 5/2011 | Eaton, Jr. et al. |
| 2011/0106565 A1 | 5/2011 | Compton et al. |
| 2011/0117878 A1 | 5/2011 | Barash et al. |
| 2011/0118561 A1 | 5/2011 | Tari et al. |
| 2011/0118573 A1 | 5/2011 | Mckenna |
| 2011/0125060 A1 | 5/2011 | Telfort et al. |
| 2011/0130636 A1 | 6/2011 | Daniel et al. |
| 2011/0137297 A1 | 6/2011 | Kiani et al. |
| 2011/0140896 A1* | 6/2011 | Menzel .................. A61B 5/746 |
| | | 340/573.1 |
| 2011/0152629 A1 | 6/2011 | Eaton et al. |
| 2011/0166465 A1 | 7/2011 | Clements et al. |
| 2011/0167133 A1 | 7/2011 | Jain |
| 2011/0172498 A1 | 7/2011 | Olsen et al. |
| 2011/0172967 A1 | 7/2011 | Al-Ali et al. |
| 2011/0178373 A1 | 7/2011 | Pacey et al. |
| 2011/0184252 A1 | 7/2011 | Archer et al. |
| 2011/0184253 A1 | 7/2011 | Archer et al. |
| 2011/0208015 A1 | 8/2011 | Welch et al. |
| 2011/0208018 A1 | 8/2011 | Kiani |
| 2011/0208073 A1 | 8/2011 | Matsukawa et al. |
| 2011/0209915 A1 | 9/2011 | Telfort et al. |
| 2011/0212090 A1 | 9/2011 | Pedersen et al. |
| 2011/0213210 A1 | 9/2011 | Temby et al. |
| 2011/0213212 A1 | 9/2011 | Al-Ali |
| 2011/0227739 A1 | 9/2011 | Gilham et al. |
| 2011/0230733 A1 | 9/2011 | Al-Ali |
| 2011/0237911 A1 | 9/2011 | Lamego et al. |
| 2011/0237969 A1 | 9/2011 | Eckerbom et al. |
| 2011/0245707 A1* | 10/2011 | Castle .................. A61B 5/31 |
| | | 600/544 |
| 2011/0257544 A1 | 10/2011 | Kaasinen et al. |
| 2011/0263950 A1 | 10/2011 | Larson et al. |
| 2011/0288383 A1 | 11/2011 | Diab |
| 2011/0295094 A1 | 12/2011 | Doyle et al. |
| 2011/0301444 A1 | 12/2011 | Al-Ali |
| 2012/0002791 A1 | 1/2012 | Kraus et al. |
| 2012/0004579 A1 | 1/2012 | Luo et al. |
| 2012/0025992 A1 | 2/2012 | Tallent et al. |
| 2012/0029300 A1 | 2/2012 | Paquet |
| 2012/0029304 A1 | 2/2012 | Medina et al. |
| 2012/0029879 A1 | 2/2012 | Sing et al. |
| 2012/0041316 A1 | 2/2012 | Al-Ali et al. |
| 2012/0041783 A1* | 2/2012 | McKee .................. G16H 40/67 |
| | | 705/3 |
| 2012/0046557 A1 | 2/2012 | Kiani |
| 2012/0059230 A1 | 3/2012 | Teller et al. |
| 2012/0059267 A1 | 3/2012 | Lamego et al. |
| 2012/0071771 A1 | 3/2012 | Behar |
| 2012/0075464 A1 | 3/2012 | Derenne et al. |
| 2012/0088984 A1 | 4/2012 | Al-Ali et al. |
| 2012/0095778 A1 | 4/2012 | Gross et al. |
| 2012/0101353 A1 | 4/2012 | Reggiardo et al. |
| 2012/0112903 A1 | 5/2012 | Kaib et al. |
| 2012/0116175 A1 | 5/2012 | Al-Ali et al. |
| 2012/0123231 A1 | 5/2012 | O'Reilly |
| 2012/0123799 A1 | 5/2012 | Nolen et al. |
| 2012/0134257 A1 | 5/2012 | Knox |
| 2012/0136221 A1 | 5/2012 | Killen et al. |
| 2012/0165629 A1 | 6/2012 | Merritt et al. |
| 2012/0179006 A1 | 7/2012 | Jansen et al. |
| 2012/0184120 A1 | 7/2012 | Basta et al. |
| 2012/0197619 A1 | 8/2012 | Namer Yelin et al. |
| 2012/0203078 A1 | 8/2012 | Sze et al. |
| 2012/0209082 A1 | 8/2012 | Al-Ali |
| 2012/0209084 A1 | 8/2012 | Olsen et al. |
| 2012/0226117 A1 | 9/2012 | Lamego et al. |
| 2012/0226160 A1 | 9/2012 | Kudoh |
| 2012/0227739 A1 | 9/2012 | Kiani |
| 2012/0239434 A1 | 9/2012 | Breslow et al. |
| 2012/0242501 A1 | 9/2012 | Tran et al. |
| 2012/0259233 A1* | 10/2012 | Chan .................. A61B 5/08 |
| | | 600/484 |
| 2012/0265039 A1 | 10/2012 | Kiani |
| 2012/0278104 A1 | 11/2012 | Traughber et al. |
| 2012/0282583 A1 | 11/2012 | Thaler et al. |
| 2012/0283524 A1 | 11/2012 | Kiani et al. |
| 2012/0284053 A1 | 11/2012 | Rosenfeld |
| 2012/0286955 A1 | 11/2012 | Welch et al. |
| 2012/0293323 A1 | 11/2012 | Kaib et al. |
| 2012/0294801 A1 | 11/2012 | Scherz et al. |
| 2012/0296178 A1 | 11/2012 | Lamego et al. |
| 2012/0302894 A1 | 11/2012 | Diab et al. |
| 2012/0303476 A1 | 11/2012 | Krzyzanowski et al. |
| 2012/0306881 A1* | 12/2012 | Nemoto .................. G16H 40/63 |
| | | 345/440 |
| 2012/0315867 A1* | 12/2012 | Davis .................. H04W 4/12 |
| | | 455/404.1 |
| 2012/0319816 A1 | 12/2012 | Al-Ali |
| 2012/0330112 A1 | 12/2012 | Lamego et al. |
| 2013/0006131 A1 | 1/2013 | Narayan et al. |
| 2013/0006151 A1 | 1/2013 | Main et al. |
| 2013/0012830 A1 | 1/2013 | Leininger |
| 2013/0023775 A1 | 1/2013 | Lamego et al. |
| 2013/0035603 A1 | 2/2013 | Jarausch et al. |
| 2013/0041591 A1 | 2/2013 | Lamego |
| 2013/0046197 A1 | 2/2013 | Dlugos, Jr. et al. |
| 2013/0046204 A1 | 2/2013 | Lamego et al. |
| 2013/0060108 A1 | 3/2013 | Schurman et al. |
| 2013/0060147 A1 | 3/2013 | Welch et al. |
| 2013/0069802 A1 | 3/2013 | Foghel et al. |
| 2013/0079610 A1 | 3/2013 | Al-Ali |
| 2013/0092805 A1 | 4/2013 | Funk et al. |
| 2013/0096405 A1 | 4/2013 | Garfio |
| 2013/0096936 A1 | 4/2013 | Sampath et al. |
| 2013/0109929 A1 | 5/2013 | Menzel |
| 2013/0109935 A1 | 5/2013 | Al-Ali et al. |
| 2013/0123616 A1 | 5/2013 | Merritt et al. |
| 2013/0162433 A1 | 6/2013 | Muhsin et al. |
| 2013/0178749 A1 | 7/2013 | Lamego |
| 2013/0190581 A1 | 7/2013 | Al-Ali et al. |
| 2013/0197328 A1 | 8/2013 | Diab et al. |
| 2013/0197364 A1 | 8/2013 | Han |
| 2013/0211214 A1 | 8/2013 | Olsen |
| 2013/0243021 A1 | 9/2013 | Siskavich |
| 2013/0253334 A1 | 9/2013 | Al-Ali et al. |
| 2013/0261494 A1 | 10/2013 | Bloom et al. |
| 2013/0267804 A1 | 10/2013 | Al-Ali |
| 2013/0274571 A1 | 10/2013 | Diab et al. |
| 2013/0274572 A1 | 10/2013 | Al-Ali et al. |
| 2013/0279109 A1 | 10/2013 | Lindblad et al. |
| 2013/0296672 A1 | 11/2013 | O'Neil et al. |
| 2013/0296713 A1 | 11/2013 | Al-Ali et al. |
| 2013/0304559 A1 | 11/2013 | Stone et al. |
| 2013/0317327 A1 | 11/2013 | Al-Ali et al. |
| 2013/0317370 A1 | 11/2013 | Dalvi et al. |
| 2013/0317393 A1 | 11/2013 | Weiss et al. |
| 2013/0324804 A1 | 12/2013 | McKeown et al. |
| 2013/0324808 A1 | 12/2013 | Al-Ali et al. |
| 2013/0324817 A1 | 12/2013 | Diab |
| 2013/0331660 A1 | 12/2013 | Al-Ali et al. |
| 2013/0331670 A1 | 12/2013 | Kiani |
| 2013/0338461 A1 | 12/2013 | Lamego et al. |
| 2013/0340176 A1 | 12/2013 | Stevens et al. |
| 2013/0345921 A1 | 12/2013 | Al-Ali et al. |
| 2014/0012100 A1 | 1/2014 | Al-Ali et al. |
| 2014/0022081 A1 | 1/2014 | Ribble et al. |

(56) References Cited

U.S. PATENT DOCUMENTS

| | | |
|---|---|---|
| 2014/0025306 A1 | 1/2014 | Weber et al. |
| 2014/0031650 A1 | 1/2014 | Weber et al. |
| 2014/0034353 A1 | 2/2014 | Al-Ali et al. |
| 2014/0046674 A1 | 2/2014 | Rosenfeld |
| 2014/0051952 A1 | 2/2014 | Reichgott et al. |
| 2014/0051953 A1 | 2/2014 | Lamego et al. |
| 2014/0051954 A1 | 2/2014 | Al-Ali et al. |
| 2014/0058230 A1 | 2/2014 | Abdul-Hafiz et al. |
| 2014/0066783 A1 | 3/2014 | Kiani et al. |
| 2014/0073167 A1 | 3/2014 | Al-Ali et al. |
| 2014/0081090 A1 | 3/2014 | Picard et al. |
| 2014/0081097 A1 | 3/2014 | Al-Ali et al. |
| 2014/0081100 A1 | 3/2014 | Muhsin et al. |
| 2014/0081175 A1 | 3/2014 | Telfort |
| 2014/0094667 A1 | 4/2014 | Schurman et al. |
| 2014/0097961 A1 | 4/2014 | Vaglio et al. |
| 2014/0100434 A1 | 4/2014 | Diab et al. |
| 2014/0114199 A1 | 4/2014 | Lamego et al. |
| 2014/0120564 A1 | 5/2014 | Workman et al. |
| 2014/0121482 A1 | 5/2014 | Merritt et al. |
| 2014/0121483 A1 | 5/2014 | Kiani |
| 2014/0127137 A1 | 5/2014 | Bellott et al. |
| 2014/0128696 A1 | 5/2014 | Al-Ali |
| 2014/0128699 A1 | 5/2014 | Al-Ali et al. |
| 2014/0129702 A1 | 5/2014 | Lamego et al. |
| 2014/0135588 A1 | 5/2014 | Al-Ali et al. |
| 2014/0142399 A1 | 5/2014 | Al-Ali et al. |
| 2014/0142401 A1 | 5/2014 | Al-Ali et al. |
| 2014/0142402 A1 | 5/2014 | Al-Ali et al. |
| 2014/0152673 A1 | 6/2014 | Lynn et al. |
| 2014/0155712 A1 | 6/2014 | Lamego et al. |
| 2014/0162598 A1 | 6/2014 | Villa-Real |
| 2014/0163344 A1 | 6/2014 | Al-Ali |
| 2014/0163402 A1 | 6/2014 | Lamego et al. |
| 2014/0166076 A1 | 6/2014 | Kiani et al. |
| 2014/0171763 A1 | 6/2014 | Diab |
| 2014/0180038 A1 | 6/2014 | Kiani |
| 2014/0180154 A1 | 6/2014 | Sierra et al. |
| 2014/0180160 A1 | 6/2014 | Brown et al. |
| 2014/0187973 A1 | 7/2014 | Brown et al. |
| 2014/0188516 A1 | 7/2014 | Kamen |
| 2014/0194709 A1 | 7/2014 | Al-Ali et al. |
| 2014/0194711 A1 | 7/2014 | Al-Ali |
| 2014/0194766 A1 | 7/2014 | Al-Ali et al. |
| 2014/0200422 A1 | 7/2014 | Weber et al. |
| 2014/0206963 A1 | 7/2014 | Al-Ali |
| 2014/0213864 A1 | 7/2014 | Abdul-Hafiz et al. |
| 2014/0243627 A1 | 8/2014 | Diab et al. |
| 2014/0257057 A1 | 9/2014 | Reis Cunha et al. |
| 2014/0266787 A1 | 9/2014 | Tran |
| 2014/0266790 A1 | 9/2014 | Al-Ali et al. |
| 2014/0275808 A1 | 9/2014 | Poeze et al. |
| 2014/0275835 A1 | 9/2014 | Lamego et al. |
| 2014/0275871 A1 | 9/2014 | Lamego et al. |
| 2014/0275872 A1 | 9/2014 | Merritt et al. |
| 2014/0275881 A1 | 9/2014 | Lamego et al. |
| 2014/0276115 A1 | 9/2014 | Dalvi et al. |
| 2014/0288400 A1 | 9/2014 | Diab et al. |
| 2014/0288947 A1* | 9/2014 | Simpson ............ G16H 10/60 705/2 |
| 2014/0296664 A1 | 10/2014 | Bruinsma et al. |
| 2014/0303520 A1 | 10/2014 | Telfort et al. |
| 2014/0309506 A1 | 10/2014 | Lamego et al. |
| 2014/0309559 A1 | 10/2014 | Telfort et al. |
| 2014/0316217 A1 | 10/2014 | Purdon et al. |
| 2014/0316218 A1 | 10/2014 | Purdon et al. |
| 2014/0316228 A1 | 10/2014 | Blank et al. |
| 2014/0316804 A1* | 10/2014 | Tran ................ G16H 80/00 705/2 |
| 2014/0323825 A1 | 10/2014 | Al-Ali et al. |
| 2014/0323897 A1 | 10/2014 | Brown et al. |
| 2014/0323898 A1 | 10/2014 | Purdon et al. |
| 2014/0330092 A1 | 11/2014 | Al-Ali et al. |
| 2014/0330098 A1 | 11/2014 | Merritt et al. |
| 2014/0330099 A1 | 11/2014 | Al-Ali et al. |
| 2014/0333440 A1 | 11/2014 | Kiani |
| 2014/0336481 A1 | 11/2014 | Shakespeare et al. |
| 2014/0343436 A1 | 11/2014 | Kiani |
| 2014/0343889 A1 | 11/2014 | Ben Shalom et al. |
| 2014/0357966 A1 | 12/2014 | Al-Ali et al. |
| 2014/0358574 A1 | 12/2014 | Tara et al. |
| 2014/0371548 A1 | 12/2014 | Al-Ali et al. |
| 2014/0371632 A1 | 12/2014 | Al-Ali et al. |
| 2014/0378784 A1 | 12/2014 | Kiani et al. |
| 2015/0001302 A1 | 1/2015 | Gelay et al. |
| 2015/0005600 A1 | 1/2015 | Blank et al. |
| 2015/0011907 A1 | 1/2015 | Purdon et al. |
| 2015/0012231 A1 | 1/2015 | Poeze et al. |
| 2015/0018650 A1 | 1/2015 | Al-Ali et al. |
| 2015/0019231 A1 | 1/2015 | Sadler et al. |
| 2015/0025406 A1 | 1/2015 | Al-Ali |
| 2015/0032029 A1 | 1/2015 | Al-Ali et al. |
| 2015/0038859 A1 | 2/2015 | Dalvi et al. |
| 2015/0045637 A1 | 2/2015 | Dalvi |
| 2015/0051462 A1 | 2/2015 | Olsen |
| 2015/0073241 A1 | 3/2015 | Lamego |
| 2015/0080754 A1 | 3/2015 | Purdon et al. |
| 2015/0087936 A1 | 3/2015 | Al-Ali et al. |
| 2015/0094546 A1 | 4/2015 | Al-Ali |
| 2015/0094618 A1 | 4/2015 | Russell et al. |
| 2015/0097701 A1 | 4/2015 | Al-Ali et al. |
| 2015/0099950 A1 | 4/2015 | Al-Ali et al. |
| 2015/0099951 A1 | 4/2015 | Al-Ali et al. |
| 2015/0099955 A1 | 4/2015 | Al-Ali et al. |
| 2015/0101844 A1 | 4/2015 | Al-Ali et al. |
| 2015/0106121 A1 | 4/2015 | Muhsin et al. |
| 2015/0112151 A1 | 4/2015 | Muhsin et al. |
| 2015/0116076 A1 | 4/2015 | Al-Ali et al. |
| 2015/0126830 A1 | 5/2015 | Schurman et al. |
| 2015/0133755 A1 | 5/2015 | Smith et al. |
| 2015/0140863 A1 | 5/2015 | Al-Ali et al. |
| 2015/0141781 A1 | 5/2015 | Weber et al. |
| 2015/0165312 A1 | 6/2015 | Kiani |
| 2015/0196237 A1 | 7/2015 | Lamego |
| 2015/0196249 A1 | 7/2015 | Brown et al. |
| 2015/0201874 A1 | 7/2015 | Diab |
| 2015/0208966 A1 | 7/2015 | Al-Ali |
| 2015/0213217 A1* | 7/2015 | Amarasingham ...... G16H 50/30 705/2 |
| 2015/0216459 A1 | 8/2015 | Al-Ali et al. |
| 2015/0220696 A1 | 8/2015 | Lekutai et al. |
| 2015/0223705 A1 | 8/2015 | Sadhu |
| 2015/0230755 A1 | 8/2015 | Al-Ali et al. |
| 2015/0238722 A1 | 8/2015 | Al-Ali |
| 2015/0245773 A1 | 9/2015 | Lamego et al. |
| 2015/0245794 A1 | 9/2015 | Al-Ali |
| 2015/0257689 A1 | 9/2015 | Al-Ali et al. |
| 2015/0272514 A1 | 10/2015 | Kiani et al. |
| 2015/0351697 A1 | 12/2015 | Weber et al. |
| 2015/0359429 A1 | 12/2015 | Al-Ali et al. |
| 2015/0366472 A1 | 12/2015 | Kiani |
| 2015/0366507 A1 | 12/2015 | Blank et al. |
| 2015/0374298 A1 | 12/2015 | Al-Ali et al. |
| 2015/0380875 A1 | 12/2015 | Coverston et al. |
| 2016/0000362 A1 | 1/2016 | Diab et al. |
| 2016/0007930 A1 | 1/2016 | Weber et al. |
| 2016/0029932 A1 | 2/2016 | Al-Ali |
| 2016/0029933 A1 | 2/2016 | Al-Ali et al. |
| 2016/0045118 A1 | 2/2016 | Kiani |
| 2016/0051205 A1 | 2/2016 | Al-Ali et al. |
| 2016/0058338 A1 | 3/2016 | Schurman et al. |
| 2016/0058347 A1 | 3/2016 | Reichgott et al. |
| 2016/0066823 A1 | 3/2016 | Al-Ali et al. |
| 2016/0066824 A1 | 3/2016 | Al-Ali et al. |
| 2016/0066879 A1 | 3/2016 | Telfort et al. |
| 2016/0072429 A1 | 3/2016 | Kiani et al. |
| 2016/0073967 A1 | 3/2016 | Lamego et al. |
| 2016/0078747 A1 | 3/2016 | King et al. |
| 2016/0081552 A1 | 3/2016 | Wojtczuk et al. |
| 2016/0095543 A1 | 4/2016 | Telfort et al. |
| 2016/0095548 A1 | 4/2016 | Al-Ali et al. |
| 2016/0103598 A1 | 4/2016 | Al-Ali et al. |
| 2016/0113527 A1 | 4/2016 | Al-Ali |
| 2016/0143548 A1 | 5/2016 | Al-Ali |

(56) References Cited

U.S. PATENT DOCUMENTS

| | | |
|---|---|---|
| 2016/0166182 A1 | 6/2016 | Al-Ali et al. |
| 2016/0166183 A1 | 6/2016 | Poeze et al. |
| 2016/0166188 A1 | 6/2016 | Bruinsma et al. |
| 2016/0166210 A1 | 6/2016 | Al-Ali |
| 2016/0192869 A1 | 7/2016 | Kiani et al. |
| 2016/0196388 A1 | 7/2016 | Lamego |
| 2016/0197436 A1 | 7/2016 | Barker et al. |
| 2016/0213281 A1 | 7/2016 | Eckerbom et al. |
| 2016/0228043 A1 | 8/2016 | O'Neil et al. |
| 2016/0233632 A1 | 8/2016 | Scruggs et al. |
| 2016/0234944 A1 | 8/2016 | Triman et al. |
| 2016/0270735 A1 | 9/2016 | Diab et al. |
| 2016/0283665 A1 | 9/2016 | Sampath et al. |
| 2016/0285717 A1 | 9/2016 | Kim et al. |
| 2016/0287090 A1 | 10/2016 | Al-Ali et al. |
| 2016/0287786 A1 | 10/2016 | Kiani |
| 2016/0296169 A1 | 10/2016 | McHale et al. |
| 2016/0310052 A1 | 10/2016 | Al-Ali et al. |
| 2016/0314260 A1 | 10/2016 | Kiani |
| 2016/0321904 A1 | 11/2016 | Johnson et al. |
| 2016/0324486 A1 | 11/2016 | Al-Ali et al. |
| 2016/0324488 A1 | 11/2016 | Olsen |
| 2016/0327984 A1 | 11/2016 | Al-Ali et al. |
| 2016/0328528 A1 | 11/2016 | Al-Ali et al. |
| 2016/0331332 A1 | 11/2016 | Al-Ali |
| 2016/0361026 A1* | 12/2016 | Sarkar .................. A61N 1/3956 |
| 2016/0367173 A1 | 12/2016 | Dalvi et al. |
| 2017/0007134 A1 | 1/2017 | Al-Ali et al. |
| 2017/0007198 A1 | 1/2017 | Al-Ali et al. |
| 2017/0014083 A1 | 1/2017 | Diab et al. |
| 2017/0014084 A1 | 1/2017 | Al-Ali et al. |
| 2017/0024748 A1 | 1/2017 | Haider |
| 2017/0027456 A1 | 2/2017 | Kinast et al. |
| 2017/0042488 A1 | 2/2017 | Muhsin |
| 2017/0055851 A1 | 3/2017 | Al-Ali et al. |
| 2017/0055882 A1 | 3/2017 | Al-Ali et al. |
| 2017/0055887 A1 | 3/2017 | Al-Ali |
| 2017/0055896 A1 | 3/2017 | Al-Ali et al. |
| 2017/0079594 A1 | 3/2017 | Telfort et al. |
| 2017/0086723 A1 | 3/2017 | Al-Ali et al. |
| 2017/0102901 A1 | 4/2017 | Burke |
| 2017/0143281 A1 | 5/2017 | Olsen |
| 2017/0147774 A1 | 5/2017 | Kiani |
| 2017/0156620 A1 | 6/2017 | Al-Ali et al. |
| 2017/0173632 A1 | 6/2017 | Al-Ali |
| 2017/0187146 A1 | 6/2017 | Kiani et al. |
| 2017/0188919 A1 | 7/2017 | Al-Ali et al. |
| 2017/0196464 A1 | 7/2017 | Jansen et al. |
| 2017/0196470 A1 | 7/2017 | Lamego et al. |
| 2017/0202490 A1 | 7/2017 | Al-Ali et al. |
| 2017/0224262 A1 | 8/2017 | Al-Ali |
| 2017/0235910 A1 | 8/2017 | Cantillon et al. |
| 2017/0245790 A1 | 8/2017 | Al-Ali et al. |
| 2017/0251974 A1 | 9/2017 | Shreim et al. |
| 2017/0251975 A1 | 9/2017 | Shreim et al. |
| 2017/0258403 A1 | 9/2017 | Abdul-Hafiz et al. |
| 2017/0311891 A1 | 11/2017 | Kiani et al. |
| 2017/0325728 A1 | 11/2017 | Al-Ali et al. |
| 2017/0332976 A1 | 11/2017 | Al-Ali et al. |
| 2017/0340293 A1 | 11/2017 | Al-Ali et al. |
| 2017/0360310 A1 | 12/2017 | Kiani et al. |
| 2017/0367632 A1 | 12/2017 | Al-Ali et al. |
| 2018/0008146 A1 | 1/2018 | Al-Ali et al. |
| 2018/0014752 A1 | 1/2018 | Al-Ali et al. |
| 2018/0028124 A1 | 2/2018 | Al-Ali et al. |
| 2018/0055385 A1 | 3/2018 | Al-Ali |
| 2018/0055390 A1 | 3/2018 | Kiani et al. |
| 2018/0055430 A1 | 3/2018 | Diab et al. |
| 2018/0064381 A1 | 3/2018 | Shakespeare et al. |
| 2018/0069776 A1 | 3/2018 | Lamego et al. |
| 2018/0103874 A1 | 4/2018 | Lee et al. |
| 2018/0199871 A1 | 7/2018 | Pauley et al. |
| 2018/0213583 A1 | 7/2018 | Al-Ali |
| 2018/0216370 A1 | 8/2018 | Ishiguro et al. |
| 2018/0242926 A1 | 8/2018 | Muhsin et al. |
| 2018/0247353 A1 | 8/2018 | Al-Ali et al. |
| 2018/0247712 A1 | 8/2018 | Muhsin et al. |
| 2018/0256087 A1 | 9/2018 | Al-Ali et al. |
| 2018/0296161 A1 | 10/2018 | Shreim et al. |
| 2018/0300919 A1 | 10/2018 | Muhsin et al. |
| 2018/0310822 A1 | 11/2018 | Indorf et al. |
| 2018/0310823 A1 | 11/2018 | Al-Ali et al. |
| 2018/0317826 A1 | 11/2018 | Muhsin |
| 2019/0015023 A1 | 1/2019 | Monfre |
| 2019/0090760 A1 | 3/2019 | Kinast et al. |
| 2019/0117070 A1 | 4/2019 | Muhsin et al. |
| 2019/0130730 A1 | 5/2019 | Boyer |
| 2019/0200941 A1 | 7/2019 | Chandran et al. |
| 2019/0239787 A1 | 8/2019 | Pauley et al. |
| 2019/0320906 A1 | 10/2019 | Olsen |
| 2019/0374139 A1 | 12/2019 | Kiani et al. |
| 2019/0374173 A1 | 12/2019 | Kiani et al. |
| 2019/0374713 A1 | 12/2019 | Kiani et al. |
| 2020/0060869 A1 | 2/2020 | Telfort et al. |
| 2020/0111552 A1 | 4/2020 | Ahmed |
| 2020/0113435 A1 | 4/2020 | Muhsin |
| 2020/0113488 A1 | 4/2020 | Al-Ali et al. |
| 2020/0113496 A1 | 4/2020 | Scruggs et al. |
| 2020/0113497 A1 | 4/2020 | Triman et al. |
| 2020/0113520 A1 | 4/2020 | Abdul-Hafiz et al. |
| 2020/0138288 A1 | 5/2020 | Al-Ali et al. |
| 2020/0138368 A1 | 5/2020 | Kiani et al. |
| 2020/0163597 A1 | 5/2020 | Dalvi et al. |
| 2020/0196877 A1 | 6/2020 | Vo et al. |
| 2020/0219335 A1 | 7/2020 | Gintz et al. |
| 2020/0253474 A1 | 8/2020 | Muhsin et al. |
| 2020/0253544 A1 | 8/2020 | Belur Nagaraj et al. |
| 2020/0275841 A1 | 9/2020 | Telfort et al. |
| 2020/0288983 A1 | 9/2020 | Telfort et al. |
| 2020/0321793 A1 | 10/2020 | Al-Ali et al. |
| 2020/0329983 A1 | 10/2020 | Al-Ali et al. |
| 2020/0329984 A1 | 10/2020 | Al-Ali et al. |
| 2020/0329993 A1 | 10/2020 | Al-Ali et al. |
| 2020/0330037 A1 | 10/2020 | Al-Ali et al. |
| 2021/0022628 A1 | 1/2021 | Telfort et al. |
| 2021/0104173 A1 | 4/2021 | Pauley et al. |
| 2021/0113121 A1 | 4/2021 | Diab et al. |
| 2021/0117525 A1 | 4/2021 | Kiani et al. |
| 2021/0118581 A1 | 4/2021 | Kiani et al. |
| 2021/0121582 A1 | 4/2021 | Krishnamani et al. |
| 2021/0161465 A1 | 6/2021 | Barker et al. |
| 2021/0236729 A1 | 8/2021 | Kiani et al. |
| 2021/0256267 A1 | 8/2021 | Ranasinghe et al. |
| 2021/0256835 A1 | 8/2021 | Ranasinghe et al. |
| 2021/0275101 A1 | 9/2021 | Vo et al. |
| 2021/0290060 A1 | 9/2021 | Ahmed |
| 2021/0290072 A1 | 9/2021 | Forrest |
| 2021/0290080 A1 | 9/2021 | Ahmed |
| 2021/0290120 A1 | 9/2021 | Al-Ali |
| 2021/0290177 A1 | 9/2021 | Novak, Jr. |
| 2021/0290184 A1 | 9/2021 | Ahmed |
| 2021/0296008 A1 | 9/2021 | Novak, Jr. |
| 2021/0330228 A1 | 10/2021 | Olsen et al. |
| 2021/0386382 A1 | 12/2021 | Olsen et al. |
| 2021/0402110 A1 | 12/2021 | Pauley et al. |
| 2022/0026355 A1 | 1/2022 | Normand et al. |
| 2022/0039707 A1 | 2/2022 | Sharma et al. |
| 2022/0053892 A1 | 2/2022 | Al-Ali et al. |
| 2022/0071562 A1 | 3/2022 | Kiani |
| 2022/0096603 A1 | 3/2022 | Kiani et al. |
| 2022/0151521 A1 | 5/2022 | Krishnamani et al. |
| 2022/0218244 A1 | 7/2022 | Kiani et al. |
| 2022/0287574 A1 | 9/2022 | Telfort et al. |
| 2022/0296161 A1 | 9/2022 | Al-Ali et al. |
| 2022/0361819 A1 | 11/2022 | Al-Ali et al. |
| 2022/0379059 A1 | 12/2022 | Yu et al. |
| 2022/0392610 A1 | 12/2022 | Kiani et al. |
| 2023/0028745 A1 | 1/2023 | Al-Ali |
| 2023/0038389 A1 | 2/2023 | Vo |
| 2023/0045647 A1 | 2/2023 | Vo |
| 2023/0058052 A1 | 2/2023 | Al-Ali |
| 2023/0058342 A1 | 2/2023 | Kiani |
| 2023/0069789 A1 | 3/2023 | Koo et al. |
| 2023/0087671 A1 | 3/2023 | Telfort et al. |

(56) References Cited

U.S. PATENT DOCUMENTS

| | | |
|---|---|---|
| 2023/0110152 A1 | 4/2023 | Forrest et al. |
| 2023/0111198 A1 | 4/2023 | Yu et al. |
| 2023/0115397 A1 | 4/2023 | Vo et al. |
| 2023/0116371 A1 | 4/2023 | Mills et al. |
| 2023/0135297 A1 | 5/2023 | Kiani et al. |
| 2023/0138098 A1 | 5/2023 | Telfort et al. |
| 2023/0145155 A1 | 5/2023 | Krishnamani et al. |
| 2023/0147750 A1 | 5/2023 | Barker et al. |
| 2023/0210417 A1 | 7/2023 | Al-Ali et al. |

FOREIGN PATENT DOCUMENTS

| | | |
|---|---|---|
| EP | 1 075 831 | 2/2001 |
| EP | 1 226 783 | 7/2002 |
| EP | 2 335 569 | 6/2011 |
| EP | 2 766 834 | 8/2014 |
| EP | 2 811 894 | 12/2014 |
| JP | 10-336064 | 12/1998 |
| JP | 2002-513602 | 5/2002 |
| JP | 2002-165764 | 6/2002 |
| JP | 2002-172096 | 6/2002 |
| JP | 2002-542493 | 12/2002 |
| JP | 2005-218036 | 8/2005 |
| JP | 2005-295375 | 10/2005 |
| JP | 2007-021213 | 2/2007 |
| JP | 2007-095365 | 4/2007 |
| JP | 2007-174051 | 7/2007 |
| JP | 2008-519635 | 6/2008 |
| JP | 2008-541045 | 11/2008 |
| JP | 2009-017959 | 1/2009 |
| JP | 2009-207836 | 9/2009 |
| JP | 2010-503134 | 1/2010 |
| JP | 2010-524510 | 7/2010 |
| JP | 2011-519607 | 7/2011 |
| JP | 2011-519684 | 7/2011 |
| JP | 2011-152261 | 8/2011 |
| JP | 2014-533997 | 12/2014 |
| WO | WO 98/029790 | 7/1998 |
| WO | WO 99/013766 | 3/1999 |
| WO | WO 99/056613 | 11/1999 |
| WO | WO 00/063713 | 10/2000 |
| WO | WO 2004/056266 | 7/2004 |
| WO | WO 2004/059551 | 7/2004 |
| WO | WO 2006/051461 | 5/2006 |
| WO | WO 2011/001302 | 1/2011 |
| WO | WO 2011/002904 | 1/2011 |
| WO | WO 2011/025549 | 3/2011 |
| WO | WO 2013/056160 | 4/2013 |
| WO | WO 2013/119982 | 8/2013 |
| WO | WO 2015/054665 | 4/2015 |
| WO | WO 2019/204368 | 10/2019 |

OTHER PUBLICATIONS

US 2022/0192529 A1, 06/2022, Al-Ali et al. (withdrawn)
Invitation to Pay Additional Fees in PCT Application No. PCT/US2019/027772, dated Jul. 5, 2019.
International Search Report & Written Opinion in PCT Application No. PCT/US2019/027772, dated Aug. 29, 2019.
International Preliminary Report on Patentability & Written Opinion in PCT Application No. PCT/US2019/027772, dated Oct. 29, 2020.
Cahalin et al., "The Six-Minute Walk Test Predicts Peak Oxygen Uptake and Survival in Patients with Advanced Heart Failure", Chest, 110(2):325-332, (Aug. 1996), Downloaded from http://journal.publications.chestnet.org/ on Oct. 16, 2013.
Capuano et al., "Remote Telemetry—New Twists for Old Technology", Nursing Management, Jul. 1995, vol. 26, No. 7, pp. 26-32.
Elmer-Dewitt, Philip, "Apple's iWatch: The killer apps may be in hospitals, not health clubs", Fortune.com, Feb. 3, 2014, http://fortune.com/2014/02/03/apples-iwatch-the-killer-apps-may-be-in-hospitals-not-health-clubs/, 4 pages.
Grundy et al., "Telemedicine in Critical Care: An Experiment in Health Care Delivery", JACEP, Oct. 1977, vol. 6, No. 10, pp. 439-444.
Grundy et al., "Telemedicine in Critical Care: Problems in Design, Implementation and Assessment", Jul. 1982, vol. 10, No. 7, pp. 471-475.
"Multihoming"—Wikipedia, the free encyclopedia, Retrieved from http://en.wikipedia.org/w/index.php?title=Multihoming&oldid=511630157 on Sep. 25, 2012.
Ruppen et al., "A Wot Approach to eHealth: Case Study of a Hospital Laboratory Alert Escalation System", Proceedings of the Third International Workshop on the Web of Things; 2012, vol. 1. No. 6, pp. 6.
Rysavy, Peter, "Making the Call with Two-Way Paging", Network Computing, Published Jan. 15, 1997, www.rysavy.com/Articles/twoway.htm, pp. 5.
Wachter et al., "The Employment of an Iterative Design Process to Develop a Pulmonary Graphical Display", Journal of the American Medical Informatics Association, vol. 10, No. 4, Jul./Aug. 2003, pp. 363-372.

* cited by examiner

INTELLIGENT MEDICAL ESCALATION PROCESS

INCORPORATION BY REFERENCE TO ANY RELATED APPLICATIONS

Any and all applications, if any, for which a foreign or domestic priority claim is identified in the Application Data Sheet of the present application are hereby incorporated by reference under 37 CFR 1.57.

BACKGROUND

Hospitals, nursing homes, and other patient care facilities typically include patient monitoring devices at one or more bedsides in the facility. Patient monitoring devices generally include sensors, processing equipment, and displays for obtaining and analyzing a medical patient's physiological parameters. Physiological parameters include, for example, respiratory rate, $SpO_2$ level, pulse, and blood pressure, among others. Clinicians, including doctors, nurses, and certain other medical personnel use the physiological parameters obtained from the medical patient to diagnose illnesses and to prescribe treatments. Clinicians also use the physiological parameters to monitor a patient during various clinical situations to determine whether to increase the level of medical care given to the patient.

Patient monitors capable of measuring pulse oximetry parameters, such as $SpO_2$ and pulse rate in addition to advanced parameters, such as HbCO, HbMet and total hemoglobin (Hbt) and corresponding multiple wavelength optical sensors are described in at least U.S. patent application Ser. No. 11/367,013, filed Mar. 1, 2006 and entitled Multiple Wavelength Sensor Emitters and U.S. patent application Ser. No. 11/366,208, filed Mar. 1, 2006 and entitled Noninvasive Multi-Parameter Patient Monitor, both assigned to Masimo Laboratories, Irvine, CA (Masimo Labs) and both incorporated by reference herein. Further, noninvasive blood parameter monitors and corresponding multiple wavelength optical sensors, such as Rainbow™ adhesive and reusable sensors and RAD-57™ and Radical-7™ monitors for measuring $SpO_2$, pulse rate, perfusion index, signal quality, HbCO and HbMet among other parameters are also available from Masimo Corporation, Irvine, CA (Masimo).

Advanced physiological monitoring systems may incorporate pulse oximetry in addition to advanced features for the calculation and display of other blood parameters, such as carboxyhemoglobin (HbCO), methemoglobin (HbMet) and total hemoglobin (Hbt or SpHb), as a few examples. Advanced physiological monitors and corresponding multiple wavelength optical sensors capable of measuring parameters in addition to $SpO_2$, such as HbCO, HbMet and Hbt are described in at least U.S. patent application Ser. No. 11/367,013, filed Mar. 1, 2006, titled Multiple Wavelength Sensor Emitters and U.S. patent application Ser. No. 11/366,208, filed Mar. 1, 2006, titled Noninvasive Multi-Parameter Patient Monitor, incorporated by reference herein. Further, noninvasive blood parameter monitors and corresponding multiple wavelength optical sensors, such as Rainbow™ adhesive and reusable sensors and RAD-57™ and Radical-7™ monitors for measuring $SpO_2$, pulse rate, perfusion index (PI), signal quality (SiQ), pulse variability index (PVI), HbCO and HbMet among other parameters are also available from Masimo.

SUMMARY

For purposes of summarizing the disclosure, certain aspects, advantages and novel features of several embodiments have been described herein. It is to be understood that not necessarily all such advantages can be achieved in accordance with any particular embodiment of the embodiments disclosed herein. Thus, the embodiments disclosed herein can be embodied or carried out in a manner that achieves or optimizes one advantage or group of advantages as taught herein without necessarily achieving other advantages as can be taught or suggested herein.

This disclosure describes embodiments of a medical network service that can replace or supplement some or all of an expensive internally staffed clinical facility network with a cloud-based networking service. The medical network service in certain embodiments can provide networking services via software as a service (SaaS) technologies, platform as a service (PaaS) technologies, and/or infrastructure as a service (IaaS) technologies. The medical network service can provide these services to large existing clinical facilities such as metropolitan hospitals as well as to smaller clinical facilities such as specialized surgical centers. The networking services provided by the medical network service can replace and/or supplement existing IT networks in hospitals and other clinical facilities and can therefore reduce costs and increase security and reliability of those networks. In addition, the medical network service can provide synergistic benefits that can improve patient outcomes and patient care.

In certain embodiments, a method of providing patient monitoring data over a network may include, by a medical edge router having one or more hardware processors, receiving input packets with the medical edge router, where the input packets include information related to patient monitoring data, analyzing the input packets to identify any patient monitoring alarms in the input packets, transmitting first ones of the input packets that do not correspond to a patient alarm over a first communications channel, and in response to detecting a patient monitoring alarm in second ones of the input packets, transmitting the second packets over multiple second communications channels.

In certain embodiments, a system for providing patient monitoring data over a network can include a medical edge router having one or more hardware processors. The medical edge router can include a traffic inspector that can receive input packets including information related to patient monitoring data and to analyze the input packets to identify any patient monitoring alarms in the input packets. Further, the medical edge router can include a routing module that can transmit first ones of the input packets that do not correspond to a patient alarm over a first communications channel and transmit second ones of the input packets over multiple second communications channels in response to detecting a patient monitoring alarm in the second input packets.

In certain embodiments, a method of providing patient monitoring data over a network can include, by a medical edge router having one or more hardware processors, receiving input data with the medical edge router. The input data can include information related to patient monitoring data. The method may also include attempting to transmit the input data over a first communications channel. Further, the method may include, in response to determining that the first communications channel is unavailable, attempting to transmit the input data over a second communications channel. Moreover, the method may include, in response to determining that the second communications channel is unavailable, transmitting a reduced form of the input data over a third communications channel.

In certain embodiments, a method of configuring a patient profile in a patient monitoring device can include, by a medical network service including one or more hardware processors, determining whether a patient admitted to a clinical facility is associated with an existing alarm settings profile stored with the medical network service. The method may also include, in response to determining that the patient is associated with the existing alarm settings profile, assigning the existing alarm settings profile to a monitoring device associated with the patient. Further, the method may also include, in response to determining that the patient is not associated with an existing alarm settings profile: identifying a matching alarm profile template that matches one or more attributes of the patient, and assigning the matching alarm profile template to the monitoring device.

The method of the preceding paragraph may include any combination of the following features. For instance, the method may further include obtaining the one or more attributes of the patient when the patient is admitted to the clinical facility. The one or more attributes of the patient can include one or more of the following attributes: age, gender, health condition, and medication associated with the patient. The identifying of the matching alarm profile template can include selecting a neonate alarm template in response to determining that the age of the patient corresponds to a neonate. The neonate alarm template can have different alarm settings than an adult alarm template. Further, the method may also include presenting the matching alarm profile template to a clinician for approval prior to assigning the matching alarm profile template to the monitoring device. The method may also include presenting the matching alarm profile template to a clinician for customization prior to assigning the matching alarm profile template to the monitoring device. The existing alarm settings profile may be generated at a second clinical facility different from the clinical facility and stored in computer storage for subsequent access.

In certain embodiments, a system for configuring a patient profile in a patient monitoring device can include a medical network service having one or more hardware processors. The medical network service can determine whether a patient admitted to a clinical facility is associated with an existing alarm settings profile stored with the medical network service. In response to determining that the patient is associated with the existing alarm settings profile, the medical network service can also assign the existing alarm settings profile to a monitoring device associated with the patient. In response to determining that the patient is not associated with an existing alarm settings profile, the medical network service can also identify a matching alarm profile template that matches one or more attributes of the patient and associating the matching alarm profile template with the patient.

The system of the preceding paragraph may include any combination of the following features. For instance, the medical network service may also obtain the one or more attributes of the patient when the patient is admitted to the clinical facility. The one or more attributes of the patient comprise one or more of the following attributes: age, gender, health condition, and medication associated with the patient. The medical network service can also identify the matching alarm profile template by at least selecting a neonate alarm template in response to determining that the age of the patient corresponds to a neonate. The neonate alarm template may have different alarm settings than an adult alarm template. The medical network service may also present the matching alarm profile template to a clinician for approval prior to associating the matching alarm profile template with the patient. The medical network service may also present the matching alarm profile template to a clinician for approval prior to associating the matching alarm profile template with the patient. The existing alarm settings profile may be generated at a second clinical facility different from the clinical facility and stored in computer storage for subsequent access.

BRIEF DESCRIPTION OF THE DRAWINGS

Throughout the drawings, reference numbers are re-used to indicate correspondence between referenced elements. The drawings are provided to illustrate embodiments of the inventions described herein and not to limit the scope thereof.

DETAILED DESCRIPTION

I. Introduction

Figure 1:
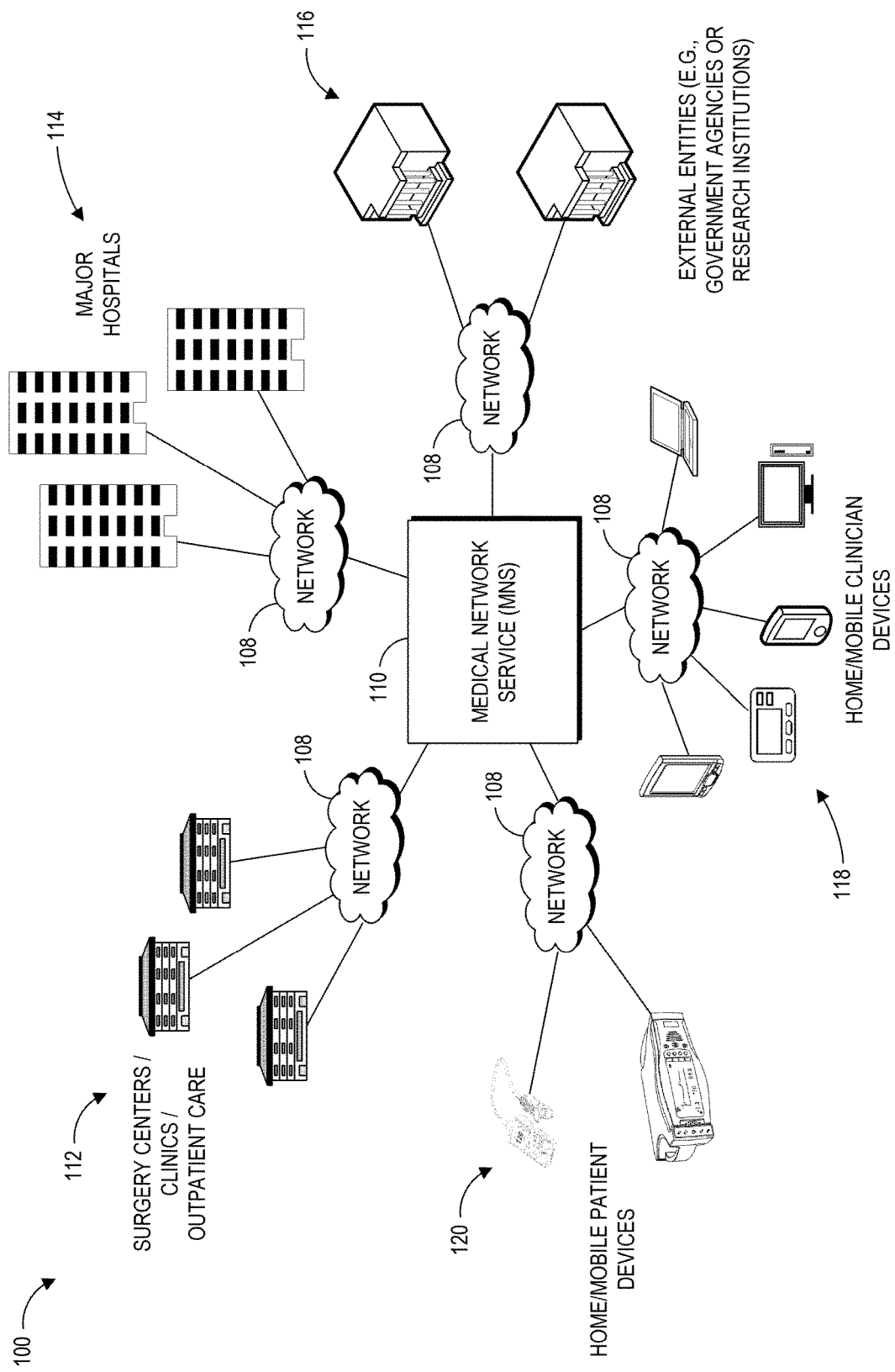
FIG. 1 depicts an embodiment of a computing environment in which various computing devices and patient monitoring devices can obtain network services from a medical network service.

A trend in hospitals today is to move away from big box hospitals that provide all services typically provided by hospitals and to provide smaller community hospitals closer to people in suburban communities. The smaller community hospitals can be more specialized and may, for example, include surgical centers that specialize in a few types of surgery or even a single type of surgery. Smaller community hospitals can provide efficiency gains in time and healthcare costs by being closer to patients and by focusing on a few areas of specialties. However, a drawback from having such facilities is that these facilities tend not to have the same financial capability as larger hospital organizations and therefore tend not to be able to afford expensive information technology network infrastructure for communicating between patient monitoring devices and clinician devices. In addition, such facilities typically also may not have the resources to purchase an electronic medical records (EMR) system, paging systems, or other systems that can be useful in caring for patients.

Furthermore, such systems can be expense for large hospitals to maintain as well. Hospitals prefer to focus on caring for patients rather than managing information technology and hospital networks. However, due to the realities of modern medical practice, many large hospitals and other clinical facilities have entire information technology (IT) departments to deal with internal networking issues including, for example, server maintenance and wireless networking maintenance. Because hospitals have a core competency in providing care for patients, hospitals tend to hire qualified IT personnel to staff their IT departments. However, as hospitals tend to reduce costs to improve patient care while impacting patients less financially, there is a risk that hospitals may be forced to cut IT costs for their IT departments and, as a result, may unintentionally compromise security and ultimately patient safety due to lower reliability of hospital networks.

This disclosure describes embodiments of a medical network service that can replace or supplement some or all of an expensive internally staffed clinical facility network with a cloud-based networking service. The medical network service in certain embodiments can provide networking services via software as a service (SaaS) technologies, platform as a service (PaaS) technologies, and/or infrastructure as a service (IaaS) technologies. The medical network service can provide these services to large existing clinical facilities such as metropolitan hospitals as well as to smaller clinical facilities such as specialized surgical centers. The networking services provided by the medical network service can replace and/or supplement existing IT networks in hospitals and other clinical facilities and can therefore reduce costs and increase security and reliability of those networks. In addition, the medical network service can provide synergistic benefits that can improve patient outcomes and patient care.

In addition, various embodiments of a medical edge router are described herein. The medical edge router can be an intelligent edge router or the like that provides redundant communications features for transmitting patient data to the medical network service.

II. Medical Network Service Embodiments

Turning to the Figures, FIG. 1 depicts an embodiment of a computing environment 100 in which various computing devices and patient monitoring devices can obtain network services from a medical network service 110. Various institutions 112, 114, 116 and devices 118, 120 are shown in the computing environment 100. These institutions include surgery centers/clinics/outpatient care centers (collectively referred to herein as small clinics 112), major hospitals 114, external entities such as government agencies 116. The example devices 118, 120 shown include home/mobile clinician devices 118, and home/mobile patient devices 120. The various institutions 112, 114, and 116 may each include internal networks of devices having computing devices and patient monitoring devices that communicate over networks 108 with the medical network service 110. The medical network service 110 can provide the users of the institutions 112, 114, and 116 with access to a variety of features that are typically included in an internal IT network installation at a hospital, some examples of which include electronic medical records or EMR, paging systems, wellness index computational services, and the like.

In addition, the MNS 110 can communicate with the home/mobile clinician devices 118 over a network 108 and the home mobile patient devices 120 of a network 108. The example networks 108 shown can be local area networks (LAN), wide area networks (WAN), the Internet, an intranet, combinations of the same or the like. Any type of clinician computing device 118 can communicate with the MNS 110 including, for example, laptops, desktops, servers, work stations, tablets, wireless handheld devices such as cell phones, smart phones, personal digital assistants and wireless pagers, combinations of the same or the like. Likewise, the MNS 110 can communicate with any type of patient monitoring device 120 including bedside devices, body worn devices, telemetry devices, and the like. Any of these patient devices 112 can output parameter data, trend data and/or alarms which can be provided to the MNS 110 over the network 108 and then re-routed by the MNS 110 to institutions 112, 114, or computers thereof, and mobile clinician devices 118.

Advantageously, in certain embodiments, by providing network services to the various entities shown, the MNS 110 can provide greater reliability, security and therefore patient safety compared to existing networks in hospitals and other clinical facilities. The MNS 110 may be implemented in one or more computing devices, such as servers, which may be geographically located, for example, in a data center, or which may be geographically disbursed, for example, in multiple data centers. The MNS 110 can include enterprise-class networking capabilities of any state of the art or currently available data center today including, for example, load balancing features, failover features, intelligent network problem detection and resolution features, and the like.

Thus for example, one benefit that the MNS 110 can provide in contrast with existing hospital networks is that if a switch or other network device were to fail at an existing hospital network, that network would then go down and deprive patients of necessary care. In contrast, in the MNS 110, if a component such as a switch goes down, the MNS 110 may be able to reroute network traffic through other switches and other components and continue or resume critical patient care services for the various institutions and devices shown.

Further, the MNS 110 can be configured such that service level agreements (SLAs) can be provided to institutions so that guarantees of service can be met by the MNS 110. An example SLA guarantee can be that alarms processed by the MNS 110 can be provided to clinician devices in the institutions 112, 114 within a specified period of time, such as a few seconds or the like. The MNS 110 may also provide uptime guarantees through SLAs or the like.

Moreover, by providing network services from the cloud, in certain embodiments, the MNS 110 can provide synergistic effects that are greater than the benefits of simply moving the networking services out of the hospital and into a centralized data center. Many examples of synergistic benefits are described in detail with respect to FIGS. 2-8 below. However, one example of a synergistic benefit of the MNS 110 in certain embodiments is that patient profiles from different institutions or clinical facilities can be maintained by the MNS 110 as a single patient profile. Thus, if a patient is in a first facility and has a profile that specifies alarm settings that are unique to that patient's health conditions, the MNS 110 can store these alarm settings in the patient's profile in the cloud. If this patient subsequently is admitted to a different facility, the MNS 110 can provide this second facility with access to the patient's profile, including the alarm settings that were previously set in the first facility. Patient profiles can enable clinicians to avoid having to re-establish useful alarm settings and/or other monitoring settings for the patient. Furthermore, the MNS 110 can enable these patient profiles to be updated and customized at the second facility.

In addition to these features, in certain embodiments any of the data collected by the MNS 110 can be anonymized and provided to the external entities 116 including, for example, government agencies or research institutions for demographic and healthcare research purposes, additional examples of which are described below with respect to FIG. 2.

Figure 2:
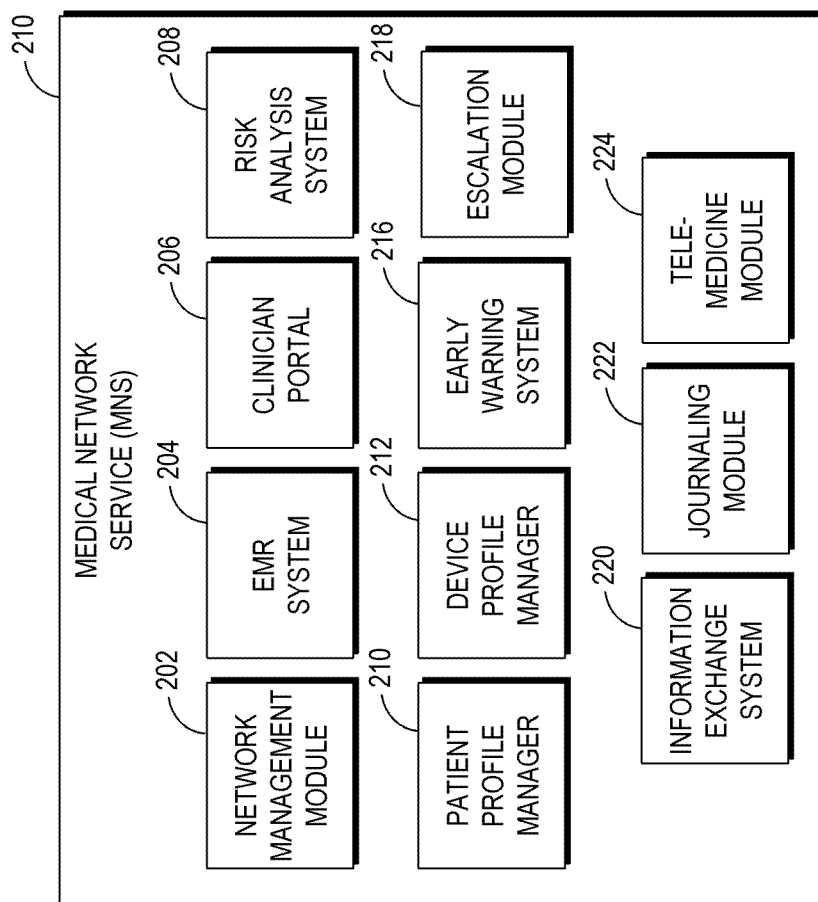
FIG. 2 depicts a more detailed embodiment of the medical network service of FIG. 1.

Turning to FIG. 2, a more detailed embodiment of a medical network service (MNS) is shown, the MNS 210. The MNS 210 can have all of the features of the MNS 110 described above. In the depicted embodiment, the MNS has several subsystems or modules that can be implemented in hardware and/or software. The example modules or components shown group functionality of embodiments of the MNS 210 together under logical descriptions. It should be understood, however, that the various modules and systems shown in the MNS 210 or portions thereof could be implemented together in a single system. In addition, not all of the systems or modules shown need be implemented on the same computing device but could instead be implemented in separate computing devices.

The MNS 210 includes, for example, a network management module 202. The network management module 202 can manage network communications with other networks, including networks in hospitals and other facilities as well as communications with mobile patient devices and clinician devices. For example, the network management module 202 can communicate with devices in hospitals and outside of hospitals, or inside of facilities and outside of facilities. The network management module 202 can provide the networking services described above with respect to FIG. 1, such as load balancing, failover, and the like. In addition, if a patient is monitored in a facility that communicates with the network management module 202, and then the patient is discharged from the facility, the network management module 202 can maintain connectivity with a body-worn or other mobile medical device associated with the patient, for example, over cellular or Wi-Fi links. Additional example features of the network management module 202 are described below with respect to FIG. 6.

The MNS 210 also includes an EMR system 204 that can generally store patient data from any facility, including data collected from patient monitoring devices in patients' homes or while patients are mobile outside of their homes or out of facilities. For example, the EMR system 204 can include such information as parameter values, trend values, alarm histories, patient demographic data, patient condition data including diagnoses, patient medical histories, and patient medications, among a variety of other patient data. The data in the EMR 204 can advantageously be used by other components of the MNS 210 as described below to improve patient care.

A clinician portal 206 of the MNS 210 can provide a user interface or user interfaces that can be accessed by clinicians via their clinician devices to monitor the health status of their patients for whom they are responsible. The clinician portal 206 may, for example, be implemented in one or more web pages, mobile applications, or other network applications and may provide information about the wellness or relative wellness of each patient.

In one embodiment, a wellness score or index is computed for each patient by a risk analysis system 208 of the MNS 210, and the clinician portal 206 can depict these wellness indices among other parameter data, trend data and alarms for each patient. In one embodiment, the clinician portal 206 facilities triaging patients by providing functionality for patients to be ordered or ranked based on their wellness scores or indices as computed by the risk analysis system 208. Example features for computing wellness indices or risk assessments are described in Appendices IV and V. For example, the risk analysis system 208 can take into two or more parameters, such as any combination of the following parameters: oxygen saturation (e.g., $SpO_2$), respiratory rate, pulse rate, heart rate, total hemoglobin level, methemoglobin, carboxyemoglobin, blood pressure, ECG output, encephalography output, or the like. The risk analysis system 208 can combine data from such parameters and reduce this data to a single value or data representation of the combination of those parameters. The single value may be, for example, an index or score that is on a scale of 0 to 10, where 10 may represent a most healthy state, while 0 may represent a least healthy state. Thus, such scores could be used to rank the relative health state or acuity of patient sicknesses and such numerical rankings can be output for presentation to clinicians in the clinician portal 206, thereby enabling clinicians to quickly triage patients.

Advantageously, in certain embodiments, the risk analysis system 208 also leverages aspects of the cloud-based infrastructure of the MNS 210 to improve the wellness index calculation. For example, the risk analysis system 208 may be able to access patient profile data from the MNS 210 that comes from previous hospital visits or other clinical facility visits from a single facility or multiple facilities to compute historical wellness indices or to compute a current wellness index. The risk analysis system 208 can also personalize the wellness index based on patient attributes stored in the EMR system 204. For example, the risk analysis system 208 can personalize which parameters are weighted more heavily in the combination of parameters that are output as a wellness index based on previous patient conditions listed in EMR system 204. In currently available systems, different institutions typically do not share their EMR data, and EMRs therefore cannot be used to correlate patient data from multiple institutions together and thereby improve risk analysis and wellness indices. However, such advantages can be made possible in certain embodiments by the centralized cloud nature of the MNS 210.

The MNS 210 also includes a patient profile manager 211. The patient profile manager 211 can manage patient profiles, which can include information about patient demographics, patient alarm settings, including alarm settings from previous visits to potentially multiple different facilities, patient conditions and so forth, and example features of which are described in greater detail below with respect to FIG. 3. The MNS 210 further includes a device profile manager 212 that can manage and store device profiles for medical devices that interact with the MNS 210 as well as optionally other computing devices. The profiles may have information about rules that can be used to track the usage of these devices as well as a variety of other features, examples of which are described in greater detail below with respect to FIGS. 4 and 5.

The MNS 210 also includes an early warning system 216. The early warning system 216 can issue early warning alarms based on parameter measurements, indices such as the wellness index or other indices. The early warning system 216 can look for patterns in patients to facilitate detecting never events, including events that should occur never or rarely, like a patient dying in bed without any intervention, particularly when a patient is home and would not ordinarily be under the care of a hospital or have access to a system like the risk analysis system 208 or the early warning system 216.

An escalation module 218 of the MNS 210 can provide functionality for escalating alarms from a first or primary care provider to a second or subsequent care provider in case the primary care provider is unavailable. However, the escalation module 218 may also provide additional functionality such as obtaining information from a remote primary care provider and providing this information to a secondary local care provider who is local to the patient and can therefore intervene using the information provided by the first care provider. Such embodiments are described below in greater detail with respect to FIG. 8.

An information exchange system 220 of the MNS 210 facilitates communicating information about patients to government or research institutions 118 described above with respect to FIG. 1. One scenario where patient information may be submitted (anonymously) to government or research institutions is where a disease outbreak has occurred. For example, information may be provided that indicates several patients in a hospital have come down with the flu. The information exchange system 220 can report this occurrence to an external entity such as the CDC or the Center for Disease Control, or state or local government agency or national government agency or worldwide agency to alert such agencies other institutions of the potentiality of a disease outbreak. If multiple institutions are using the services of the MNS 210, then such information about patient conditions can be correlated and provided to these institutions as described above. More generally, the information exchange system 220 can provide data about changing patient conditions continuously or periodically to government or research organizations to enable such organizations to rapidly respond to changes in regional health issues.

Further, the data provided by the information exchange system 220 can be valuable to government agencies or research institutions to determine the effects of local conditions on health conditions. It may be discovered, for instance, that patients that go to a specific facility or set of facilities in a region are afflicted with disease related to nearby coal mining which can be ascertained by research institution or a government agency that has responsibility over such activities. Accordingly, the information exchange system 220 can provide value data that can provide reports that can be used by external entities to improve patient care.

A journaling module 222 of the MNS 210 can capture clinician interactions with medical devices that are in the institutions and/or that are in patients' homes or that are body worn in mobile situations. The interactions can include any type of button press, alarm setting change, RFID tag interaction, or the like and can be recorded for the purposes of determining clinician response times to alarms or other measures of the quality of a clinician's care. The journaling module 222 can further leverage the centralized monitoring capabilities of the MNS 210 to compare the quality of care as journaled or otherwise calculated amongst different institutions as an apples-to-apples comparison because some or all of the data from these institutions can be provided to the centralized MNS 210.

Further, the journal module 222 can facilitate comparing the quality of care between different units in a hospital or other facility including different floors or groups of clinicians or shifts, or the like. The journal module 222 can also facilitate comparing similar groups amongst different facilities, such as an ICU group in two different facilities, and can thereby enable an organization to identify gaps or deficiencies of care in different facilities that can be corrected. This information can be provided in real time or near-real time so that adverse patient care outcomes can be quickly addressed, in contrast to the past where information about quality of care is often analyzed well after an adverse care event has occurred (or even after a patient has been discharged). Further embodiments of journaling and detecting clinician interactions with devices (including via RFID tags) are described in greater detail in Appendices I through III.

A telemedicine module 224 of the MNS 210 can facilitate telecommunications between clinicians and patients, including telepresence communications where clinicians can diagnosis, treat, or otherwise attend to the needs of patients remotely using audio visual systems or the like. The telemedicine module 224 can also be used in conjunction with features of the escalation module 218 described below with respect to FIG. 8.

Figure 3:
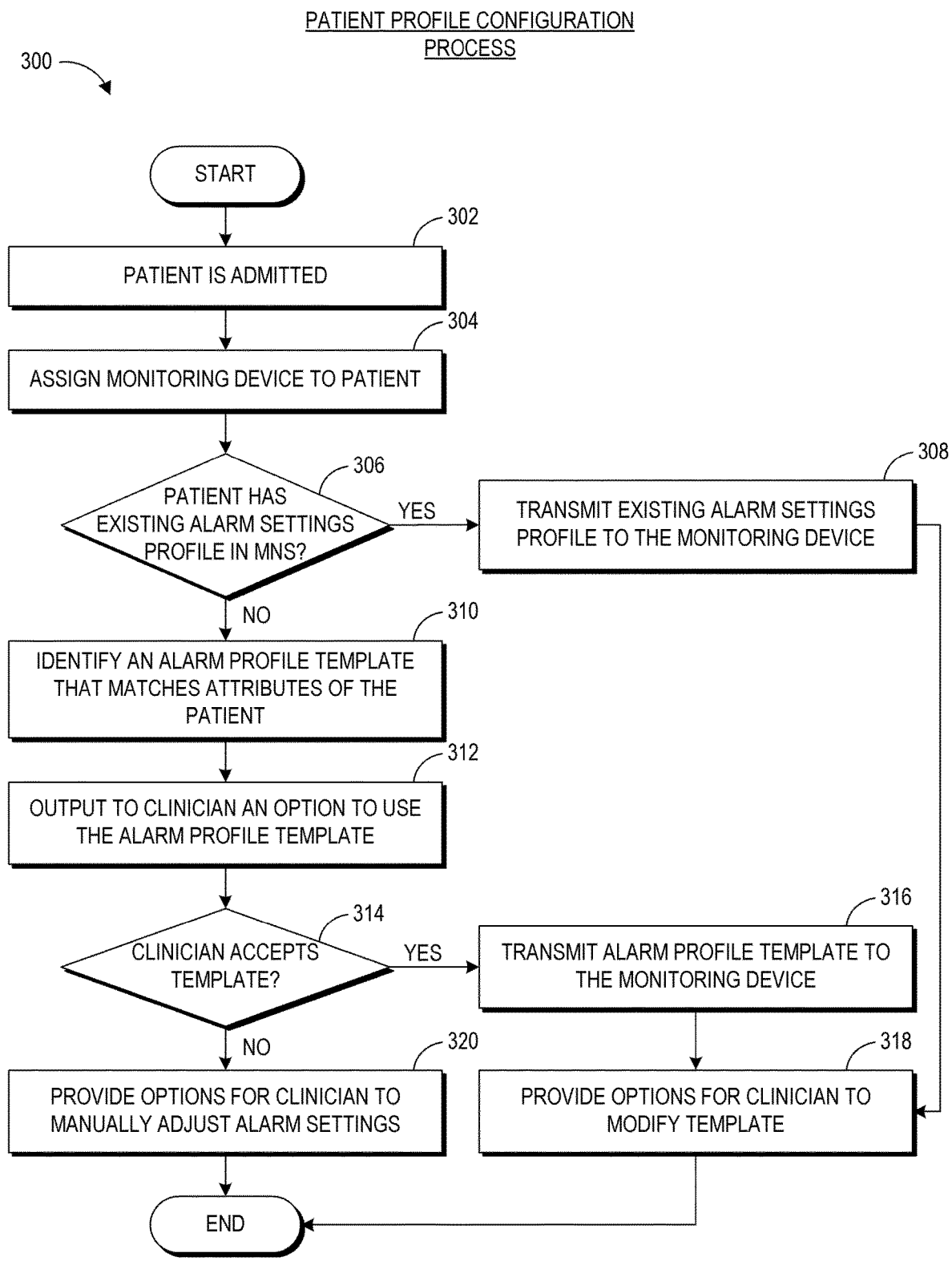
FIG. 3 depicts an embodiment of a patient profile configuration process.

FIG. 3 depicts an embodiment of a patient profile configuration process 300. The patient profile configuration process 300 can be implemented by any of the medical network services described above, including the MNS 110 or 210. In addition, portions of the process 300 can be implemented by other devices in any of the institutions described above, or any of the medical devices or clinician devices described above. Thus the processing of the process 300 can be distributed amongst different devices. However, although different devices including devices other than those shown or described herein could implement the process 300, for convenience certain aspects of the process 300 are described as being implemented by the patient profile manager 211 of FIG. 2. Advantageously, in certain embodiments the patient profile configuration process 300 can facilitate improved monitoring of patients by maintaining patient profiles from visit to visit, a particular institution and/or from visit to visit amongst multiple institutions.

The process 300 begins at block 302 where a patient is admitted to a hospital. In the admission process, the patient may provide demographic information to the hospital, including the gender, age, weight, other health conditions that the patient has, medications that the patient is on and so forth. This information can be stored in the EMR described above with respect to FIG. 2. In another embodiment, when a patient is admitted, the patient provides insurance information or other identifying information that uniquely identifies the patient and thereby enables the patient profile manager 211 to look up the patient's profiled date stored in the MNS 210.

At block 304, the patient is assigned a monitoring device. The monitoring device may be a bedside device or a body worn device and could be used in an institution such as a hospital or at the patient's home or while the patient is mobile. At block 306 the patient profile manager 211 determines whether the patient has existing alarm settings profile in the MNS 210. An existing alarm settings profile may include customized alarm settings based on the demographics of the patient. Different types of patients may benefit better from different alarm settings. For instance, neonates or children may require different alarm settings from adults because their physiology differs from adults. Likewise, alarm settings can be based on gender, race due to physiological differences among races (however slight), as well as due to age and previous medical conditions or medications that a person is on or symptoms that the patient is reporting when admitted to the hospital.

If the patient has an existing alarm settings profile in the MNS, then the patient profile manager 211 transmits, uploads, or otherwise downloads the existing alarm settings profile to the monitoring device associated with the patient at block 308. Thus, it can be seen that an advantage in certain embodiments of the patient profile manager 211 is that the existing profile can be stored in the cloud and therefore accessed whenever that patient is readmitted to a hospital or other clinical facility. However, if the patient does not have an existing alarm profile, at block 310 the patient profile manager 211 can identify an alarm profile template that matches attributes of the patient, including any of the demographic attributes described above. So, for example, if the patient is a neonate, the patient profile manager 211 can access the stored template of alarm settings for neonate.

At block 312, the patient profile manager 211 outputs an option to use the alarm profile template to a clinician. The clinician can then decide whether to use that particular template, select a different template, or customize the template to meet the needs of the particular patient. Thus, continuing at decision block 314, the patient profile manager 211 determines whether the clinician accepts the template. If so, the patient profile manager 211 transmits, uploads, or otherwise downloads the alarm profile template to the monitoring device and provides options for the clinician to modify the template at block 318. Block 318 may also be reached after block 308 where the existing alarm settings profile is downloaded to the monitoring device. However, if the clinician does not accept the template 314 as described above, at block 320 the patient profile manager 211 can provide options for the clinician to manually adjust alarm settings or to select another template.

In alternative embodiments, instead of downloading or transmitting patient profiles to devices, each device may already have several patient profiles already installed, and the patient profile module 211 selects one and assigns it to the device for the particular patient.

Figure 4:
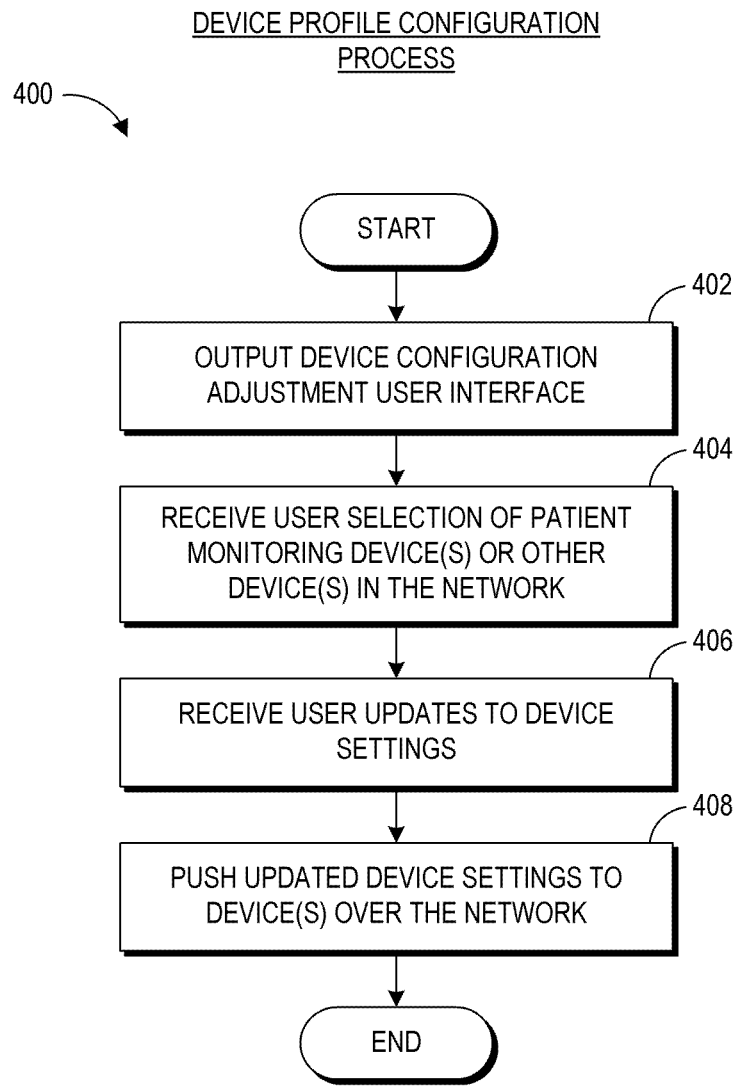
FIG. 4 depicts an embodiment of a device profile configuration process.

FIG. 4 depicts an embodiment of a device profile configuration process 400. Like the process 300, the process 400 can be implemented by any of the MNSs as described above including the MNS 110 or 210, or any of the other devices described herein. In an embodiment the device profile configuration process 400 is implemented by the device profile manager 212 of FIG. 2. Accordingly, for ease of illustration the process 400 will be described as being implemented by the device profile manager 212 although it should be understood that any other device or system could implement the process 400. The process 400 can advantageously provide centralized management of patient monitoring devices by the MNS.

Figure 5:
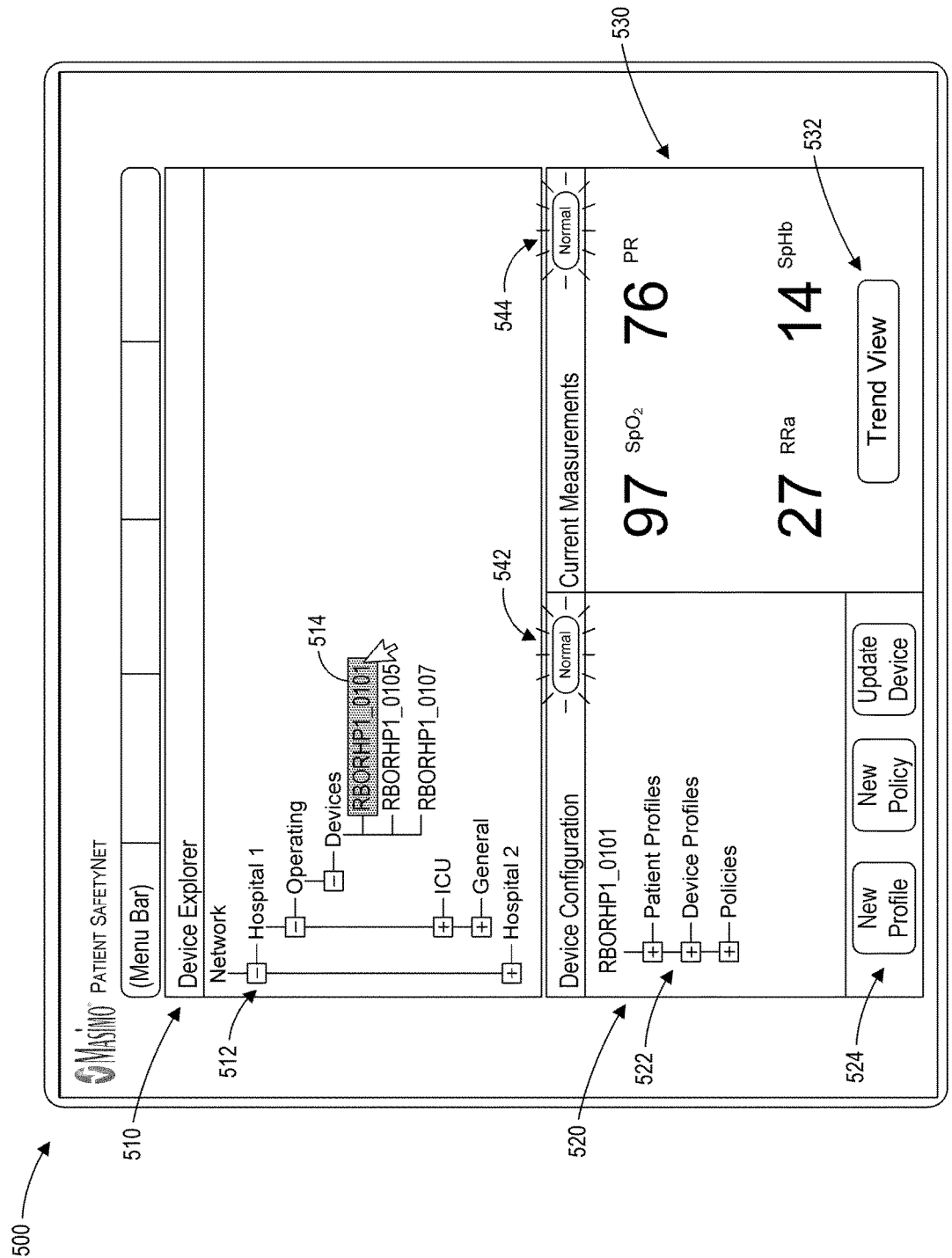
FIG. 5 depicts an example device configuration adjustment user interface.

At block 402, the device profile manager 212 outputs a device configuration adjustment user interface. An example of such a user interface is shown in FIG. 5 and described in greater detail below. Generally speaking, the device configuration adjustment user interface can provide functionality for a user, such as a network professional, to monitor the configuration status of monitoring devices and/or adjust configuration status of such devices. Devices may have profiles associated with them that include information about alarm settings and other settings. Profiles can be patient profiles that are associated with devices, clinician profiles that are associated with devices and so forth. In addition, the user interface can enable users to update software on the monitoring devices.

At block 404, the device profile manager 212 receives a user selection of a patient monitoring device or other device in the network from the user interface. The user may select any device shown in the user interface to obtain more data about that device, e.g., to change settings on the device or to set policies or rules for the device. At block 406, the device profile manager 212 receives user updates to the device settings and pushes those updated device settings to the devices over the network at block 408.

Turning to FIG. 5, an example of a device configuration adjustment user interface 500 is shown. The example user interface 500 could be output by the device profile manager 212 according to the process 400. The user interface 500 can be implemented in a web browser or other application software that may or may not be implemented in a web browser.

The user interface 500 includes a device explorer 510, device configuration pane 520, and a current measurements pane 530. The device explorer 510 includes a tree 512 or hierarchy of facilities and devices, enabling users to select a facility, explore floors or subsections of that facility, and select devices within those floors or subsections. In the depicted embodiment, the tree 512 shown includes data representing a hospital that has an operating room floor, an intensive care unit (ICU) floor, and a general floor. The operating room floor option is expanded to show devices within the operating room floor. One of the devices 514 is shown selected by a user (e.g., using a mouse or touch screen input).

Advantageously, in certain embodiments, the user interface 500 can provide access to any device that connects to the MNS. Thus, network administrators can drill down into any device among several different facilities. In addition to a tree view, in some embodiments, other views of the devices can be shown, such as a topology view that shows interconnections between devices in the network.

Upon user selection of one of the devices 514, the device profile manager 212 can output details 522 of the device 514 in the device configuration pane 520. These details 522 include configuration settings about the device and possibly other information stored on the device, including patient profiles, device profiles, policies, what network the device is connected to (not shown), and optionally applications installed on the device and settings thereof (not shown). These details 522 can be selected by a user to adjust the configuration settings of the selected device 512. For example, a user can select specific patient profiles to add or remove to the device.

In one embodiment, each device can have one or more profiles. In one embodiment, each device has a single device profile that specifies where in the facility the devices belongs (such as what floor), what network the device is connected to, and so forth. Policies can also be associated with a device and may be part of a device's profile. Policies can include rules about how a device may be used and may be defined by users (including clinicians and/or network technicians or the manufacturer of the device). For example, a policy may be defined that states that a device is to be used for general floor monitoring and not intensive care or operating room monitoring. Accordingly, if a clinician attempts to associate the device with a patient in the ICU or operating room floor, software in the device (or in the MNS) can detect that the device is being used on the wrong floor and therefore may prevent operation of the device or issue an audio/visual warning to not use the device. The device or MNS can detect that the device is on the wrong floor, for instance, by analyzing network traffic to and from the device to determine where in the network the device is connected.

Another example of a policy is related to patient profiles. A user can define a policy that the device may be used only with neonates or only with adults. In another example scenario, a user can define a policy that the device will issue a warning if a user changes alarm limits on the device or changes alarm limits beyond certain thresholds. Another policy could be defined to state that alarm thresholds cannot be changed on the device unless the device is associated with an existing patient profile. Software on the device and/or the MNS can enforce the policies by warning users of violations and/or preventing operation of the device until the policies are complied with. Accordingly, the policies used in devices can improve patient care outcomes.

Advantageously, in certain embodiments, because the MNS may be implemented in a centralized cloud architecture, the user interface 500 can enable policies, profiles, and settings to be adjusted for a plurality of devices at once instead of one at a time. As a result, network and device maintenance can be streamlined. Likewise, the user interface 500 can facilitate pushing software updates to multiple of the devices at once. Example user interface controls 524 are shown, which are buttons in the depicted embodiment, for adding new profiles, policies, and updating devices.

Moreover, the device profile manager 212 can detect problems occurring in different devices and report these problems or a representation thereof on the user interface 500. In the depicted embodiment, a device health indicator 542 is shown that can reflect the health of a device on the network. The device health indicator 542 can be a light or graphic that is green, yellow, or red depending on whether a device is functioning well, functioning poorly, or not functioning at all. Other indicators may be used than a colored light, such as text, a graph, a number, 1-5 star ratings, or any combinations of the same or the like. The device profile manager 212 can score devices based on device performance and adjust the output of the indicator 542 accordingly. Instead of a separate indicator, a graphic for each device in the device explorer 510 could instead show colors for each device, corresponding to the health of each device.

The current measurements pane 530 depicts current measurements on the selected device 514 and is optional in some embodiments. A trend view button 532 can allow a user to see trends on these measurements. Like the device health indicator 542, a patient health indicator 544 is also shown that may have some or all of the same functionality as the device health indicator 542 except with respect to a patient. The patient health indicator 544 can also be displayed on a medical device associated with the patient, a clinician device remote from the medical device, or a nurse's workstation, to name a few examples. The patient health indicator 544 can reflect an overall health or wellness of the patient and may be based on the wellness index described above. In other embodiments, the patient health indicator 544 can include or be the wellness index.

Figure 6:
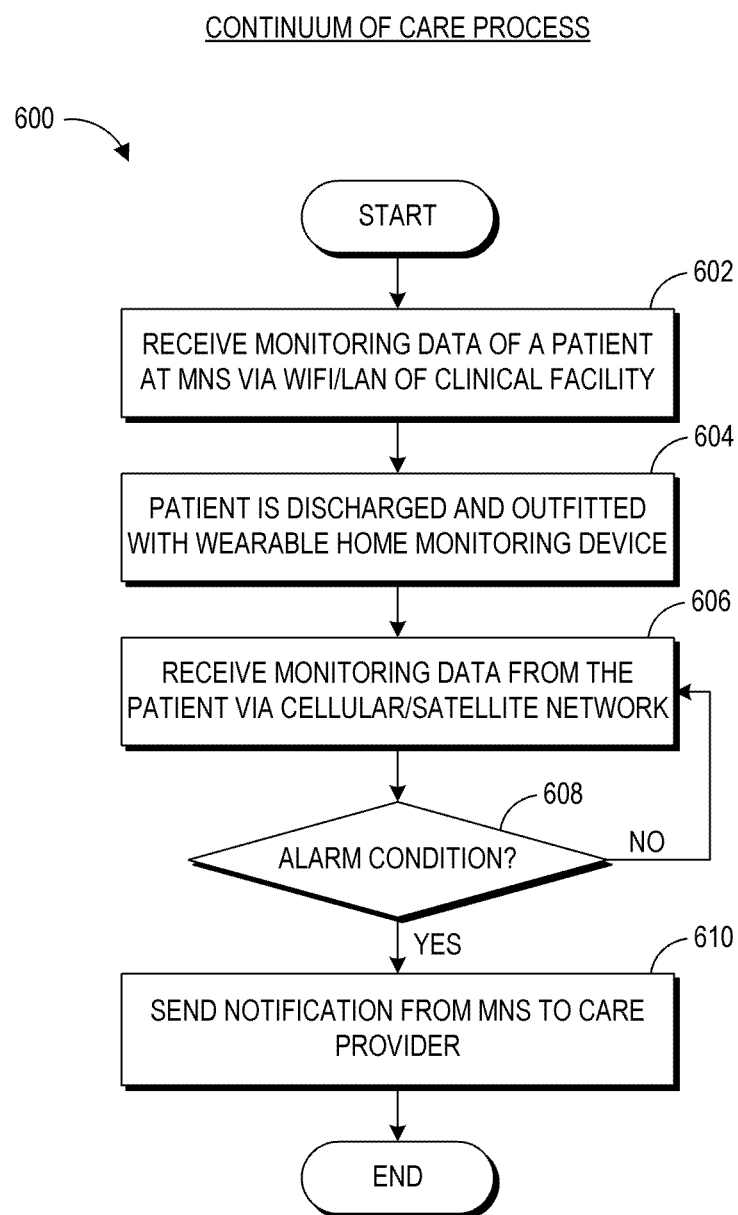
FIG. 6 depicts an embodiment of a continuum of care process.

FIG. 6 depicts an embodiment of a continuum of care process 600. Like the process 300, the process 600 can be implemented by the MNS 110 or 210, or any of the other devices described herein. In an embodiment, the process 600 can be implemented at least in part by the network management module 202 to facilitate continued patient monitoring when a patient leaves a hospital or other facility.

At block 602, the network management module 202 receives monitoring data of a patient at the MNS via WiFi, LAN, or other networking technologies of the clinical facility to which the patient is admitted. Once the patient is discharged, the patient may be outfitted with a wearable home monitoring device 604. The wearable monitoring device may be the same device used to monitor the patient in the clinical facility. In addition, the device may be a mobile device that need not be wearable in some embodiments. The device may, for instance, be any of the devices or variations thereof described in U.S. patent application Ser. No. 13/010,653, filed Jan. 20, 2011, titled "Wireless Patient Monitoring System," the disclosure of which is hereby incorporated by reference in its entirety.

When a patient is discharged, the patient typically leaves the hospital network. Accordingly, in currently-available systems, there is a typically a period of time where the patient is not being monitored once the patient leaves the facility. However, the network management module 212 can facilitate continued monitoring of the patient by receiving monitoring data from the patient via a cellular or satellite network at block 606. Then, if an alarm condition is detected at block 608, the network management module 212 (or the early warning system 216 using the network management module 212) can pass a notification from the MNS to a care provider 610. Accordingly, the MNS can facilitate a continuum of care for a patient and continuous monitoring even when a patient has left a clinical facility.

Figure 7:
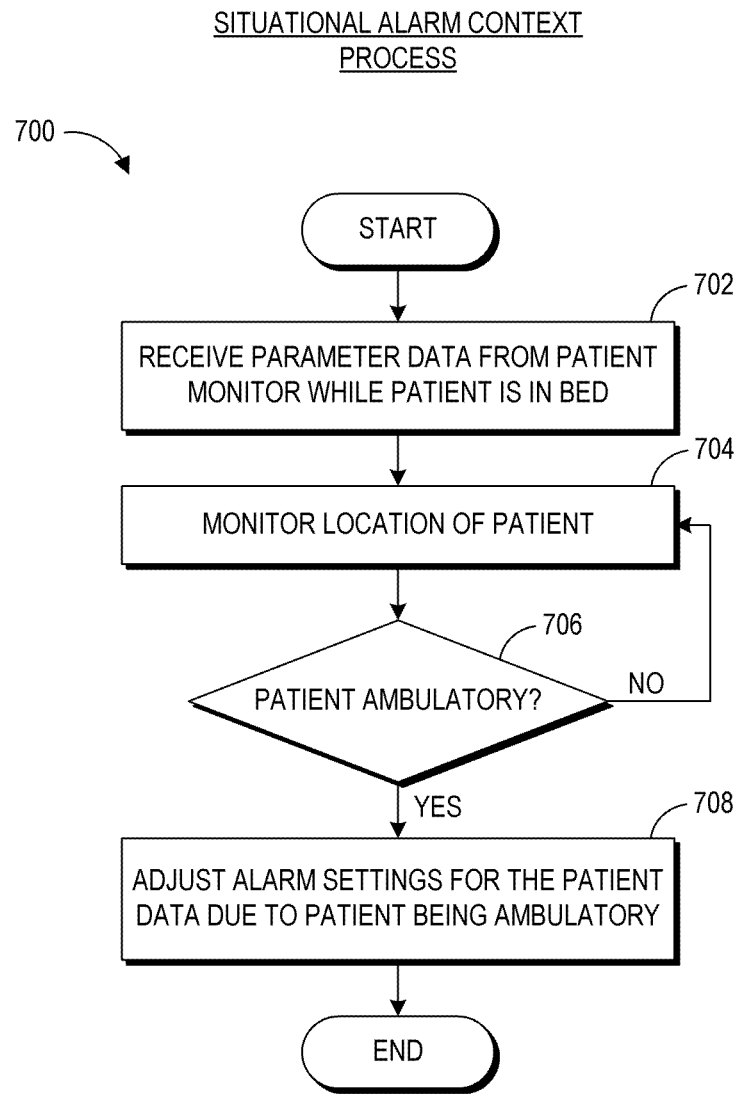
FIG. 7 depicts an embodiment of a situational alarm context process.

FIG. 7 depicts an embodiment of a situational alarm context process 700. Like the process 300, the process 700 can be implemented by the MNS 110 or 210, or any of the other devices described herein. In an embodiment, the situational alarm context process 700 is implemented by the risk analysis system 218. The situational alarm context process 700 can take into account more than just the measured parameters of a patient when determining whether to alarm. The process 700 can also take into account the situational context of the patient, such as whether the patient is moving.

At block 702, the risk analysis system 718 receives parameter data from the patient monitor while the patient is in bed. When the patient is in bed, the patient is typically resting and may have a lower heart rate than when the patient is moving, all other factors being equal. However, when the patient moves, the patient's heart rate may elevate, and other parameters associated with the patient may change as well. It can be desirable to adjust patient monitoring to account for patient changes in movement or other situational context to avoid producing false alarms.

Thus, the location and/or motion of the patient are monitored at block 704. The location and/or motion of the patient may be monitored in several ways. One or more motion sensors may be included in the patient monitoring device, and the monitoring device may be worn on the patient. Thus, for example, the monitoring device may include a gyroscope, accelerometer, or the like that can determine whether the patient is moving, walking, or the like. Telemetry can also be used to ascertain where a patient is located and/or moving to. For instance, when a patient is wearing a patient monitor that communicates over wireless networks, the MNS can determine the patient's position by triangulation of nearby access points to which the patient's monitoring device is sending and receiving signals. In other situations, patients may take an assisted walk with a nurse or other clinician. The nurse or other clinician may have an RFID tag or the like that can be detected by the patient monitoring device (as described in Appendix III), giving a clue as to the movement and/or location of the patient.

Thus, the risk analysis system 218 determines at block 706 whether the patient is ambulatory or moving. If so, the risk analysis system 218 can adjust alarm settings for the patient due to the patient being ambulatory. For example, the risk analysis system 218 can increase a heart rate threshold limit that would trigger an alarm if it detects that the patient is ambulatory. If the patient is not ambulatory, the process loops back to block 704, where the patient is continued being monitored using existing alarm settings.

In other embodiments, the risk analysis system 218 may adjust patient monitoring differently. Instead of adjusting alarm settings, for example, the risk analysis module 218 can assign scores to patients based on their activity level and incorporate these scores into the wellness index described above. For instance, if the patient is walking, the risk analysis module 218 may lower the weight given to heart rate in calculating the wellness index so as to avoid an increased heart rate adversely impacting the wellness index calculation. The risk analysis module 218 can also take into account additional factors before determining whether to adjust the weight applied to the heart rate, however, such as the health conditions or diseases of the patient. If the patient has heart disease or some other condition, it may be prudent to alarm or indicate an adverse health condition whenever the patient's heart rate rises, no matter the activity level of the patient. Thus, the risk analysis module 218 may use the health condition of the patient to override other considerations such as patient movement.

Figure 8:
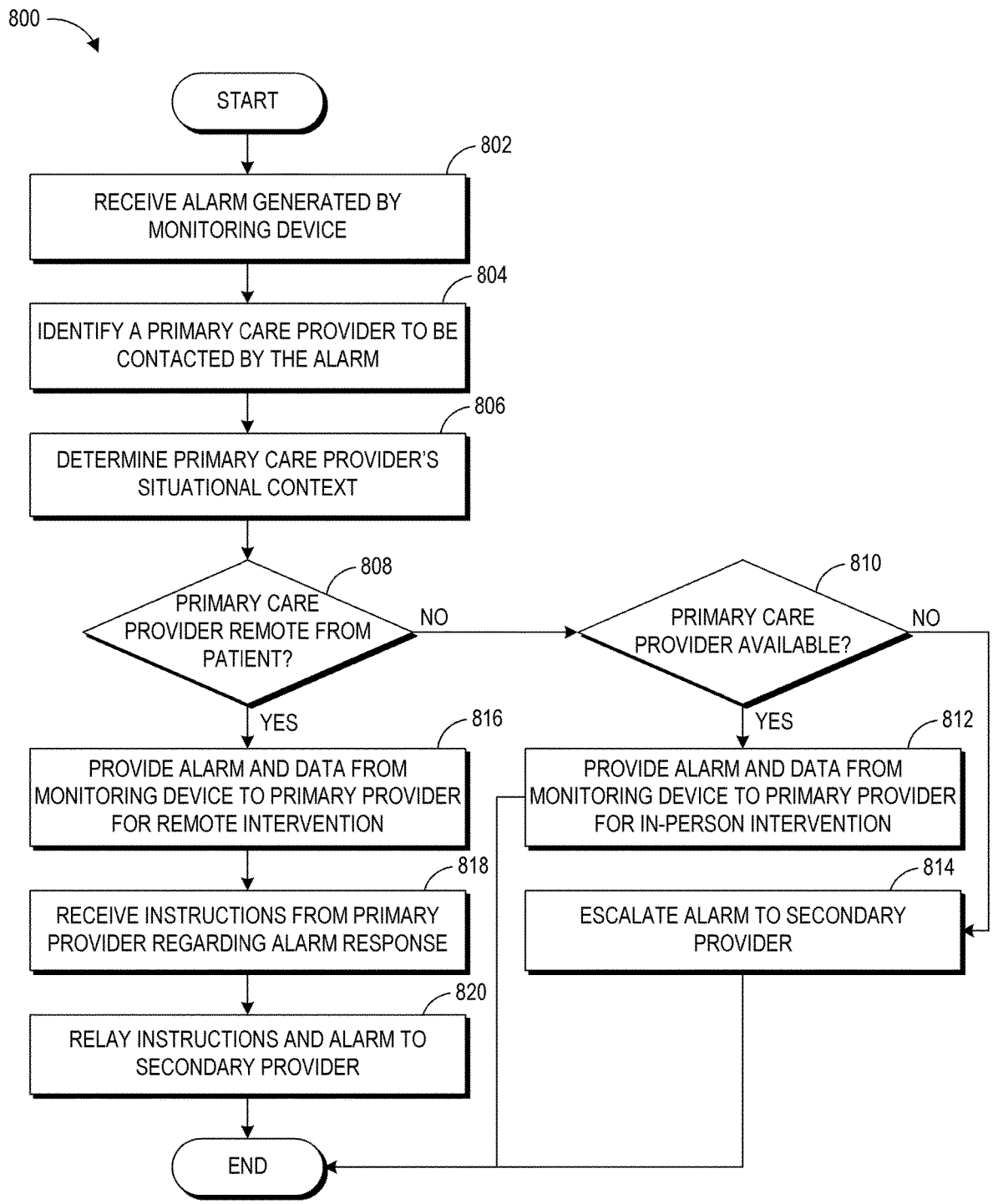
FIG. 8 depicts an embodiment of a situational escalation process.

FIG. 8 depicts an embodiment of a situational escalation process 800. Like the process 300, the process 800 can be implemented by the MNS 110 or 210, or any of the other devices described herein. As described above, alarms may be escalated from a primary provider (or group of providers) to a secondary provider (or group of providers) if the primary provider is unavailable to address an alarm. In an embodiment, the process 800 is implemented by the escalation module 218 and enables clinicians to remotely provide information useful to a secondary provider to whom an alarm is escalated.

At block 802, an alarm generated by a monitoring device is received by the escalation module 218. The escalation module 218 identifies a primary provider to be contacted by the alarm at block 804. The escalation module 218 may store a list of providers that are associated with a patient and may provide a user interface that enables users to adjust this list in certain embodiments. At block 806, the escalation module 218 determines the primary care provider's situational context. If the situational context of the primary care provider is that the provider is located far from the patient, the escalation module 218 may perform intelligent escalation as described below.

The situation where the primary provider is far removed from the patient may occur increasingly more commonly. In particular, as smaller clinics replace some functionality of larger hospitals, clinicians may not all be co-located in the same hospital. Further, modern travel conveniences make it possible for surgeons and other specialists to travel to patient sites and vice versa to perform patient care. Accordingly, a primary provider may be distant from several of his or her patients.

The escalation module 218 determines at block 808 whether the primary care provider is located remotely from the patient. If not, the escalation module 218 further determines at block 810 whether the primary care provider is available. The primary care provider may be off duty or unable to take a page, for example, in which case the escalation module 218 escalates the alarm to a secondary provider at block 814. Otherwise, the escalation module 218 can provide the alarm and optionally data from the monitoring device (such as trend data) the primary provider for possible in-person intervention at block 812.

However, in the scenario where the primary care provider is not located close by but may be available, the escalation module 218 can still provide the alarm and optionally data from the monitoring device to the primary provider for remote intervention at block 816. The primary provider may use telepresence technologies to interact with the patient, e.g., using the telemedicine module 224 of the MNS 210. The escalation module 218 can then receive instructions from the primary provider regarding an alarm response at block 818, e.g., through a user interface or telepresence technology. These instructions can include a diagnosis, recommended medication, or other recommended course of actions that the escalation module 218 can relay to the secondary provider along with the alarm at block 820.

Thus, in certain embodiments, the process 800 enables a remote primary care provider to provide instructions to a secondary, local care provider to better enable the secondary care provider to respond to an alarm. This process 800 can therefore improve upon currently-available processes, which typically require the secondary provider (who may be less familiar with the patient than the primary provider) to interpret the patient's alarm without guidance from the remote primary care provider.

III. Additional Medical Network Service Embodiments

In addition to the embodiments described above, in certain embodiments, clinician devices (including mobile devices) can interact with the MNS and/or with the patient monitoring devices directly. A clinician's mobile device, for instance, can receive alarms, trend data, parameter data, or any other data associated with a patient from the MNS or directly from the patient monitoring devices. The clinician's device may also receive data from multiple patients that are associated with the clinician, including features of the clinician portal described above. Thus, for example, the clinician's device may depict wellness indices for the various patients and thereby enable the clinician to triage alarms. The clinician device can also include the capability to silence alarms remotely (e.g., by transmitting an instruction input by the clinician to the patient monitoring device). In an embodiment, the clinician device communicates directly with the patient monitoring device using Bluetooth (e.g., if in the same room or nearby) or WiFi or another wireless technology. In another embodiment, the clinician device communicates with the patient monitoring device through MNS if the clinician (or the clinician's organization) is affiliated with the MNS (e.g., is a paying customer) but otherwise directly communicates with the patient monitoring device. In the scenario where the clinician is affiliated with the MNS, the clinician may be able to advantageously obtain trend data for a plurality of patients, whereas directly connecting to each patient device individually may or may not provide this functionality.

Further, in certain embodiments, each patient device includes a network communications module that enables the patient device to communicate with the MNS over a network. In anther embodiment, a gateway device (not shown) is provided in each room of a facility, or in a few rooms of a facility, which connects to the patient device and which communicates with a plurality of devices in the room or rooms. The gateway device may itself be a patient monitor that includes ports for connecting to other devices. The gateway device can receive data from these other medical devices and pass the data on to the MNS for storage in the EMR, analysis by the risk analysis module 218, and the like. Some examples of other devices in a typical clinical facility that can connect through the gateway device include ventilators, pumps, general oxygen equipment, and the like. An example gateway device that may be used with the features described herein is described in U.S. application Ser. No.

13/651,167, filed Oct. 12, 2012, titled "Medical Monitoring Hub," the disclosure of which is hereby incorporated by reference in its entirety.

Moreover, any of the features described herein can be implemented in conjunction with features from any of the following applications, the disclosure of each of which is hereby incorporated by reference in their entirety: U.S. application Ser. No. 11/633,656, filed Dec. 4, 2006, titled "Physiological Alarm Notification System"; U.S. application Ser. No. 12/904,925, filed Oct. 14, 2010, titled "Systems and Methods for Storing, Analyzing, Retrieving, and Displaying Streaming Medical Data"; U.S. application Ser. No. 12/904,377, filed Oct. 14, 2010, titled "Medical Monitoring System"; U.S. application Ser. No. 13/269,296, filed Oct. 7, 2011, titled "Risk Analysis System"; and U.S. application Ser. No. 13/371,767, filed Feb. 13, 2012, titled "Medical Characterization System."

IV. Medical Edge Router Embodiments

Figure 9:
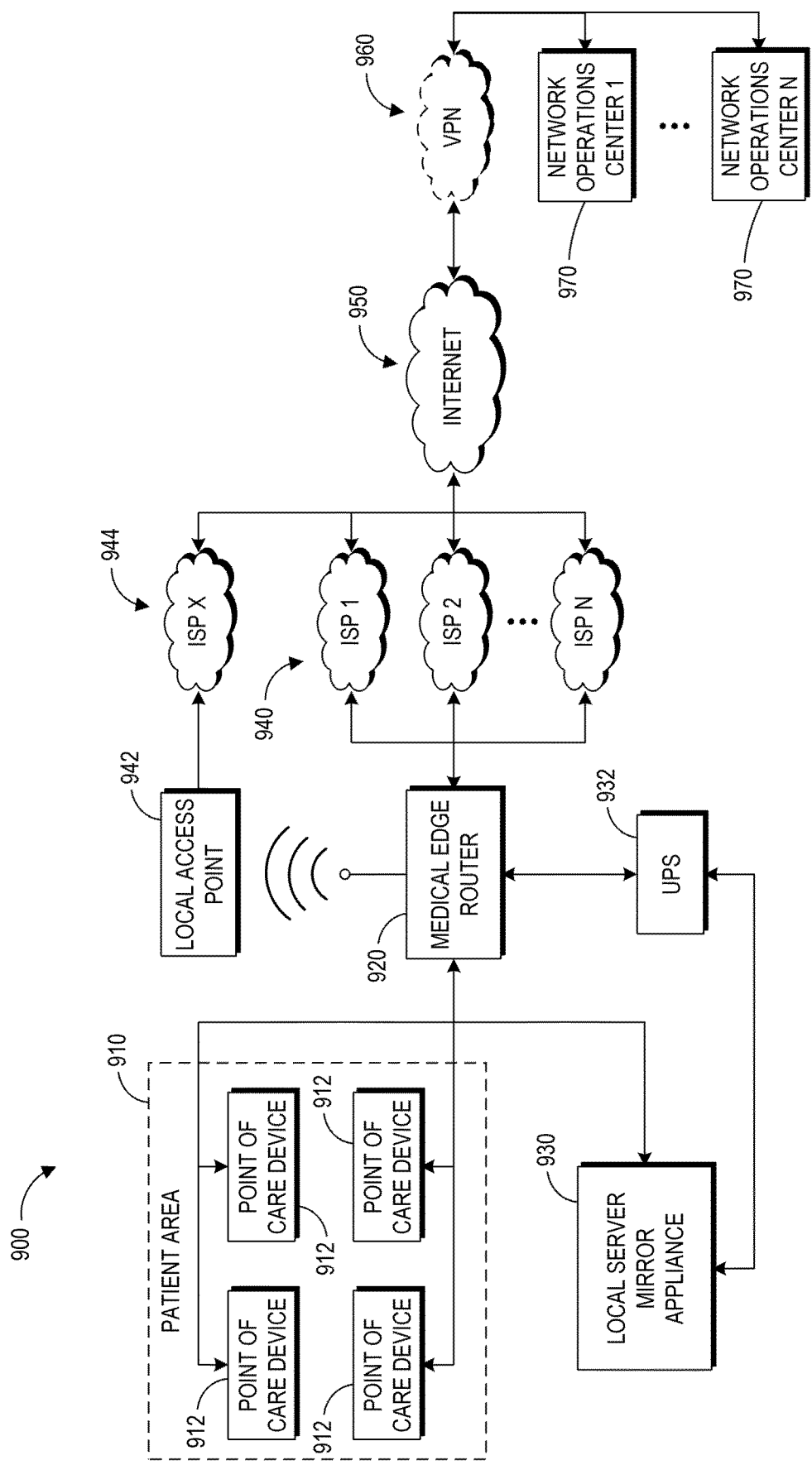
FIG. 9 depicts another embodiment of a computing environment in which various computing devices and patient monitoring devices can obtain network services from a medical network service.

Turning to FIG. 9, another embodiment of a computing environment 900 is shown for providing clinicians with access to patient care data. The computing environment 900 is compatible with and can be used in conjunction with the features of the computing environment 100 described above, as well as with other embodiments described above. For example, the computing environment 900 can provide access to a medical network service, such as the MNS 110 or 210. The MNS can be implemented in one or more network operation centers 970, as shown. Each of the network operation centers 970 can be implemented in a separate data center in geographically dispersed locations so as to provide redundant access and access that is geographically proximate to users of the MNS.

One of the major challenges associated with providing network-based medical monitoring services for hospitals and other clinical facilities is network connectivity. Networks, including the Internet, are prone to network failure and therefore, it can be desirable to provide for redundancy in communication channels or pathways that access the MNS. Advantageously, in the depicted embodiment of FIG. 9, the computing environment 900 includes multiple redundant pathways to communicate data from point-of-care devices 912 to the MNS in the network operation centers 970, which will be described herein.

As shown, the point-of-care devices 912 are arranged in a patient area 910, which may be a hospital or a subset thereof. The point-of-care devices 912 can be patient monitoring devices, such as any of the patient monitoring devices described above, and can monitor any physiological parameter of a patient, such as oxygen saturation, blood pressure, heart rate, ECG parameters, respiratory rates, hemoglobin, and the like. The point-of-care devices 912 can be bedside devices or body-worn patient monitoring devices, and in general, may provide physiological parameter data, trend data, alarms and alerts to clinician devices over a network. Further, the point-of-care devices 912 can provide such data outside of a hospital network to clinician devices over the Internet 950 (or other wide-area network) through a medical edge router 920.

In the depicted embodiment, the medical edge router 920 communicates with the network operation centers 970 over multiple communication pathways, including multiple Internet Service Provider networks 940. For convenience, this specification generally refers to the Internet Service Provider networks 940 as ISPs. The medical edge router 920 can be an intelligent edge router that provides redundant communications for transmitting patient data, among other features. For instance, in one embodiment, the medical edge router 920 can attempt to send patient data, including physiological parameters, trends and/or alarms, to the MNS in a network operations center 970 over a first one of the ISPs 940. If the first ISP 940 is unavailable, the medical edge router 920 can attempt to communicate with the MNS through a second one of the ISPs 940, and so forth, until the medical edge router 920 has attempted to contact the MNS through most or all of the ISPs 940.

In one embodiment, if the ISPs are unavailable, then the medical edge router 920 can attempt to contact the MNS through a wireless ISP 944; for example, by communicating wirelessly through a local access point 942, which then communicates via the ISP 944. In other embodiments, the medical edge router 920 can attempt to first communicate through broadband mechanisms, such as wired LAN, WAN or wireless or satellite-based broadband, prior to using dial-up or lower bandwidth links. In yet another embodiment, the medical edge router 920 performs back-up communications to clinicians via cellular networks if the ISPs 940, 944 are unavailable. In such instances, the medical edge router 920 may, for instance, send a text message (via SMS) or email or other communication to one or more clinicians that includes some or all of the data obtained from one or more point-of-care devices 912. Since text messages and emails tend to be limited in length, the medical edge router 920 can instead summarize data obtained from the point-of-care devices 912 and send the summarized data over the cellular network or other network.

In some embodiments, the ISPs 940 or 944 may be available, but one or more of the network operation centers 970 that host the MNS may be down and unavailable. Accordingly, it can be useful in such circumstances for the medical edge router 920 to communicate via SMS or email over one of the ISPs 940 or cellular networks (not shown), to clinicians. In any case, when communicating via SMS or email, the medical edge router 920 can reduce the amount of data sent or selectively prioritize the data sent to clinicians, to send higher-priority data in view of the reduced bandwidth available, in such communication of channels. In one embodiment, for example, the medical edge router 920 can send a summary of the alarms or parameter values from the point-of-care devices 912 to a clinician via SMS or email or a similar mechanism, without sending trend data, which can consume a significant amount of bandwidth. In another example, medical edge router 920 prioritizes alarms over parameter values over trend data, such that if an alarm is to be transmitted, the medical edge router 920 can transmit the alarm to a clinician device, instead of more bandwidth-intensive data. If no alarms are to be transmitted, the medical edge router 920 can transmit more bandwidth-intensive data.

In yet another embodiment, the medical edge router 920 is also connected to an uninterruptible power supply or UPS 932 that can provide the medical edge router 920 with continued power, should mains power become available. The UPS 932 can also power other systems in the clinical facility, including the point-of-care devices 912 and a local server mirror appliance 930. The local server mirror appliance 930 can be a server or other computing device that includes some or all of the functionality of the MNS described above. In one embodiment, the local server mirror appliance 930 includes important or critical patient care functionality of the MNS. For example, the appliance 930 may include a portion of the functionality of the MNS and may operate in parallel with the MNS to calculate parameter values or a wellness index in case of failure or inability to contact the MNS over the network.

Also shown is a VPN 960 through which the point-of-care devices 912 can connect to the network operation centers 970. The VPN 960 can provide security for such communications, although the VPN 960 may be optional in some embodiments.

It should also be noted that in certain embodiments, the computing environment 900 of FIG. 9 can include multiple edge routers 920, which can be used for failover purposes within the hospital network. For instance, each point-of-care device 912 can be connected to two or more edge routers 920 and can send data over each edge router 920 to reduce the potential of having a single point of failure in the network.

Figure 10:
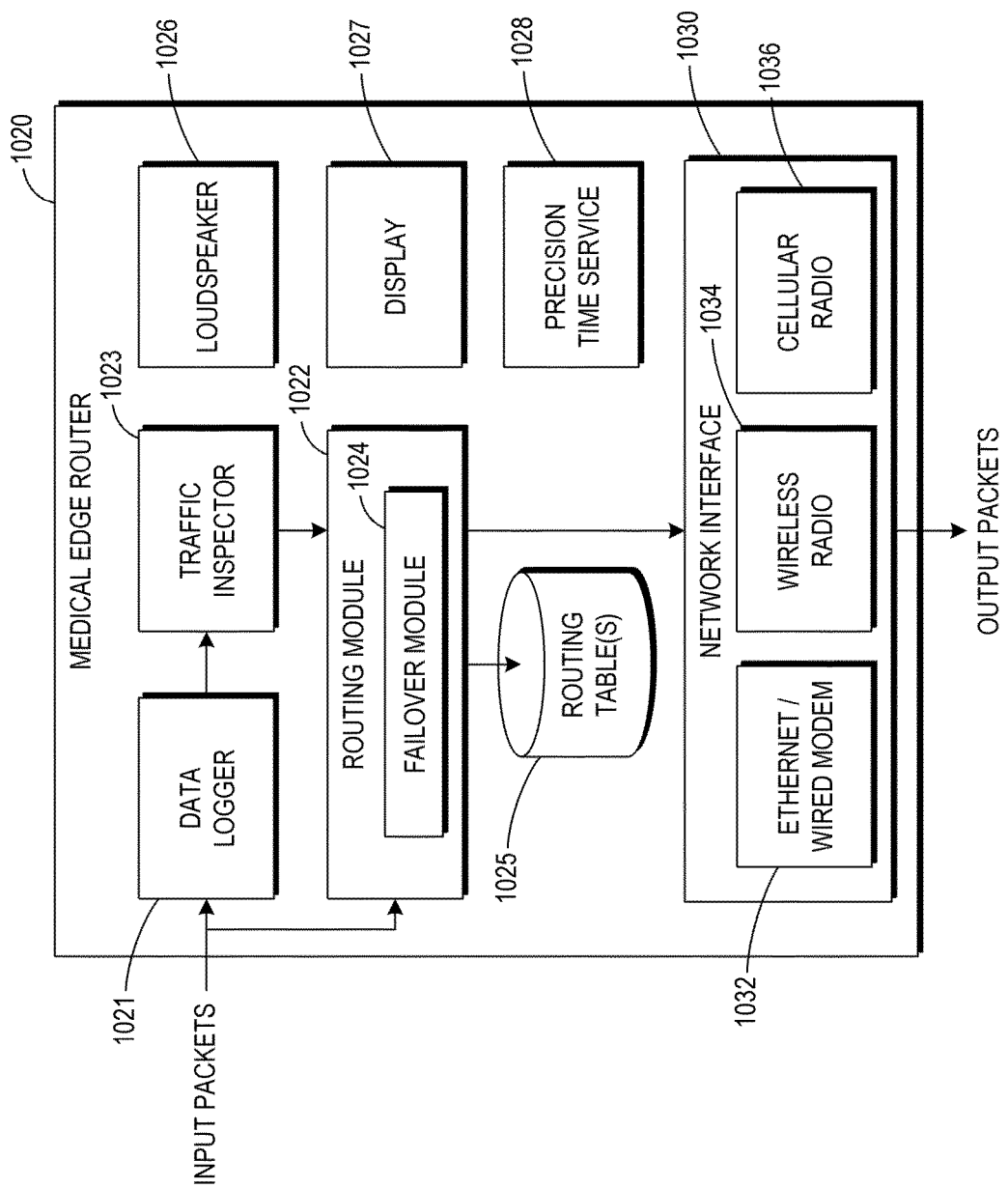
FIG. 10 depicts an embodiment of a medical edge router.

Turning to FIG. 10, a more detailed example of a medical edge router 1020 is shown. The medical edge router 1020 can have some or all the functionality of the medical edge router 920 described above with respect to FIG. 9. Various components of the medical edge router 1020 shown can be implemented in hardware and/or software. The medical edge router 1020 receives input packets and forwards output packets, which the medical edge router 1020 can route to an appropriate destination in the network. The medical edge router 1020 can be placed at the edge of a network in or near a clinical facility (see, e.g., FIG. 9) and therefore may provide access to other networks outside of the clinical facility network.

The example medical edge router 1020 shown includes a data logger 1021 and a routing module 1022 that both receive the input packets. The data logger 1021 can be a packet-sniffer or the like that copies the input packets and thereby makes the input packets available to a traffic inspector 1023. The data logger 1021 may also store the packets for subsequent analysis, including analysis for determining conditions leading up to a network communications failure after the failure occurred. The traffic inspector 1023 can inspect the input packets logged by the data logger 1021 to determine whether any of the input packets include alarms. If an alarm is detected, the traffic inspector 1023 can notify the routing module 1022 of such an alarm condition, enabling the routing module 1022 to prioritize the distribution of packets that relate to include alarms (including optionally packets having parameter data associated with the alarms).

The routing module 1022 includes a failover module 1024 that can receive communications from the traffic inspector 1023 about alarms and can select destinations for the packets accordingly. The routing module 1022 also communicates with one or more routing tables 1025 that can be populated using any suitable routing protocol, such as the Border Gateway Protocol (BGP) commonly used in routers in the Internet. The routing module 1022 can route the input packets to appropriate routers or switches in the Internet (or other networks) based on the information stored in the routing tables 1025. The routing module 1022 can update the routing tables 1025 over time, using BGP or another protocol.

The failover module 1024 can provide the redundant failover features described above, at least in part, with respect to FIG. 9. For instance, the failover module 1024 can determine whether an ISP or other network channel is unavailable and can fail over or escalate communications to another ISP or communication channel when network channel failure is detected.

The routing module 1022 can prioritize alarms, as described above, when detected by the traffic inspector 1023. When an alarm is included in an input packet, as indicated by the traffic inspector 1023, the routing module can prioritize the alarm by broadcasting the alarm over multiple or all channels used by the routing module 1022. For instance, the routing module 1022 can broadcast such packets over multiple ISPs, or over both wired and wireless ISPs, or over both an ISP and a cellular network, or the like.

Packets are sent from the routing module 1022 to a network interface card 1030 that can implement the data link and/or physical layers of the TCP/IP network stack. The network interface 1030 includes, in the depicted embodiment, an Ethernet or wired modem 1032, a wireless (e.g., WiFi) radio 1034, and a cellular radio 1036. The network interface 1030 outputs the output packets based on instructions from the routing module 1022. For instance, if the routing module 1022 instructs the network interface 1030 to send packets over a wired ISP, the network interface 1030 can send such packets via the Ethernet or wired modem 1032. Conversely, if the routing module 1022 instructs the network interface 1030 to send such packets via a WiFi or wireless link, the wireless radio 1034 of the network interface 1030 can transmit such packets. Similarly, the cellular radio 1036 can transmit certain packets over cellular networks (such as SMS packets), as instructed by the routing module 1022. The components of the network interface 1030 are example components only and could be added to or removed from in other embodiments.

In the depicted embodiment, the medical edge router 1020 also includes a loudspeaker 1026 and a display 1027. The loudspeaker 1026 can output audible alarms when network connectivity is detected as being down by the medical edge router 1022. For instance, whenever an ISP becomes unavailable, or another network communications channel becomes unavailable, the routing module 1022 can cause the loud speaker 1026 to issue an audible alarm. Likewise, the display 1027 can output visual alarms in response to the routing module 1022 detecting a network communication path being unavailable, enabling network personnel to troubleshoot the medical edge router 1020 when needed. The medical edge router 1020 can also send SNMP packets to IT personnel to alert IT personnel of network failures, failover conditions, and the like.

In addition, the medical edge router 1020 can also include a precision time service 1028 that can apply time stamps to packets sent by the routing module 1022. This precision time service 1028 can be synchronized or substantially synchronized with time services used by other medical edge routers 1020 in the hospital network or in other hospital networks remote from the medical edge router 1020 shown. Accordingly, packets received by the MNS in any one of the network operation centers 970 can maintain a synchronous or time-ordered view of the packets. It can be beneficial to maintain a synchronous or time-ordered view of medical data received from the point-of-care devices 912 to ensure or attempt to ensure that alarms and other data are received in the proper time order, so that clinicians can take appropriate action based on such data.

In one embodiment, the precision time service 1028 communicates with one or more GPS satellites to obtain a precision time value. In another embodiment, the precision time service 1028 communicates with an atomic clock, or the like, to obtain a precision time value, although other techniques may be used to obtain precision time values.

The medical edge router 1020 can have many other features than those shown in FIG. 10 (or fewer features). For instance, the medical edge router 1020 can monitor or manage performance of the local clinical facility network. Multiple medical edge routers 1020 can be included in or in communication with a single facility, such as a single medical edge router 1020 for each hospital floor. Many other embodiments are possible.

Figure 11:
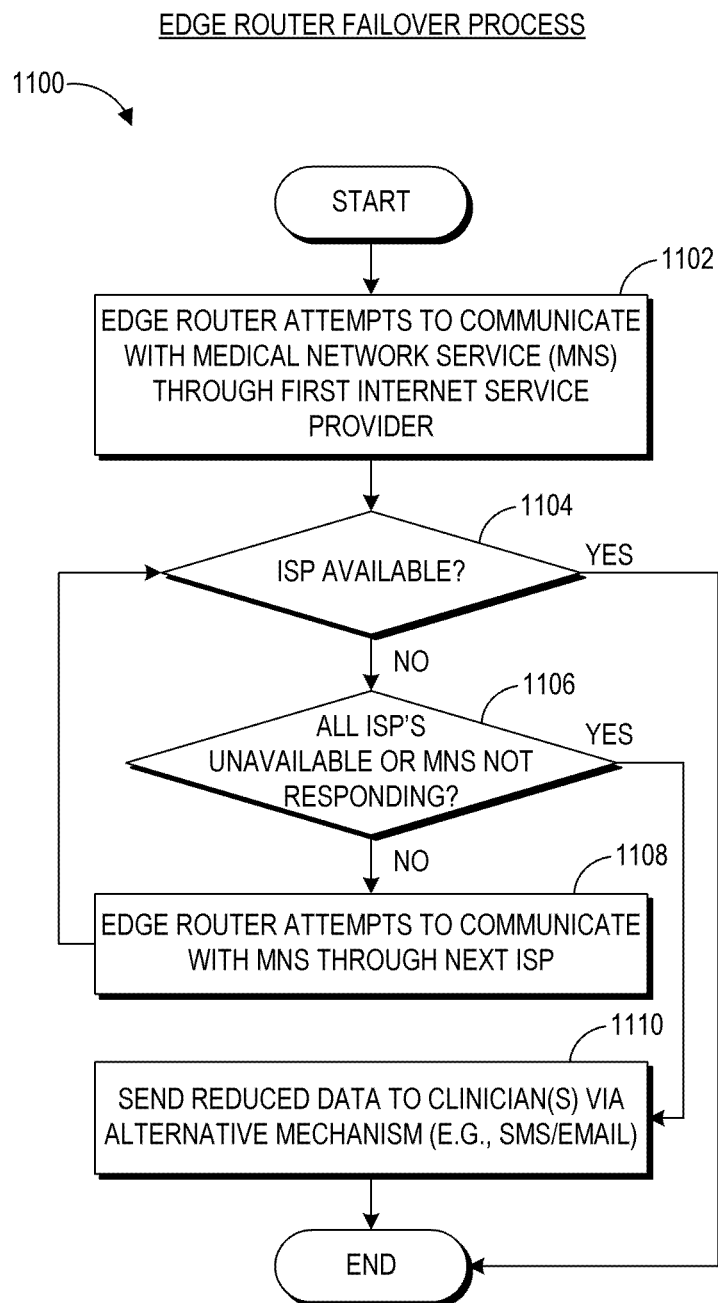
FIG. 11 depicts an embodiment of an edge router failover process.

Turning to FIG. 11, an example edge router failover process 1100 is shown. The edge router failure process 1100 can be implemented by the edge router 920 or 1020 described above and can advantageously provide for redundancy in hospital network communications. While the process 1100 will be described with respect to the medical edge router described above for convenience, it should be understood that the process 1100 could be implemented by any computing device or network device.

At block 1102, the edge router attempts to communicate with the medical network service (MNS) through a first ISP. At block 1104, the medical edge router determines whether the ISP is available. If so, the edge router is able to communicate its message to the MNS, and the process 1100 ends. However, if the ISP is not available, then the medical edge router determines at block 1106 whether all ISPs are unavailable, or whether the MNS is not responding. If all ISPs are unavailable, it may be helpful for the medical edge router to contact the MNS using another communication pathway, such as cellular or wireless. However, some ISPs may be available while the MNS is not responding, in which case it may also be useful to use a different communication pathway to provide patient information to clinicians.

If all ISPs are unavailable or the MNS is not responding, then the edge router can attempt to communicate with the MNS through the next ISP at block 1108, looping back to block 1104. However, if all ISPs are unavailable or the MNS is not responding, then the edge router can send reduced data to the clinicians via an alternative mechanism, such as email or SMS, at block 1110. For example, the edge router can transmit a summary of patient monitoring data over a cellular network or via email to clinicians. In one embodiment, in response to detecting that all IPSs are unavailable or the MNS is not responding, the routing module 1022 sends a request to the local server mirror appliance 930 or the point of care devices 912 for a summary of the patient monitoring data. Then, upon receipt of the summary data, the edge router can communicate the summarized data over an alternative communications channel. In other embodiments, the local server mirror appliance 930 and/or the point of care devices 912 send summary data to the edge router together with more verbose patient monitoring data so that the edge router can send the summary data without delay in case of communications pathways to the MNS or clinicians becoming unavailable.

Figure 12:
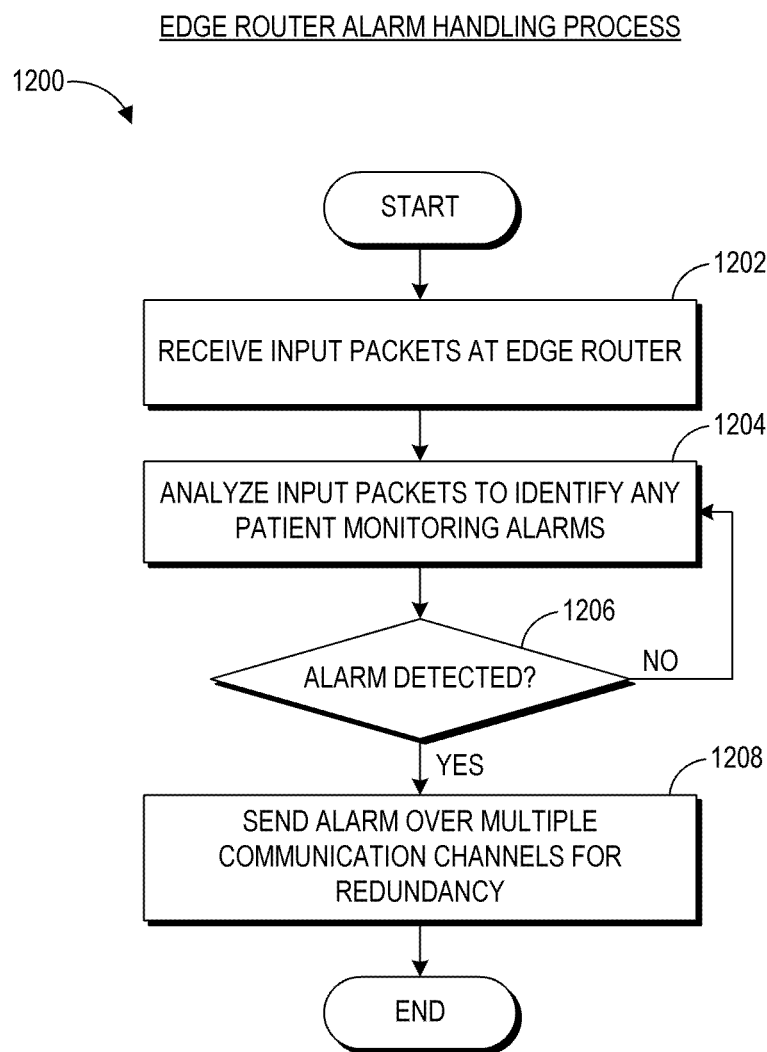
FIG. 12 depicts an embodiment of an edge router alarm handling process.

Turning to FIG. 12, an example embodiment of an edge router alarm-handling process 1200 is shown. The edge router alarm-handling process 1200 can also be implemented by either of the edge routers 920 or 1020 described above, and for convenience, will be described with respect to the medical edge router, although the process 1200 could be implemented by any computing device or network device.

At block 1202, the edge router receives input packets, and at block 1204, analyses those input packets to identify any patient monitoring alarms. For instance, the traffic inspector 1023 of the edge router 1020 can identify any patient monitoring alarms in a given packet. In one embodiment, the traffic inspector 1023 searches for a particular payload in a packet that indicates that an alarm is in the packet, and in another embodiment, alarm information is included in a header of the packet.

If an alarm is detected at block 1206, the traffic inspector 1023 sends the alarm over multiple communication channels for redundancy at block 1208, such as over multiple ISPs, or over a wired ISP and a wireless ISP, or over an ISP and over a cellular network, combinations of the same, or the like. If an alarm is not detected at block 1206, then the process 1200 can loop back to 1204, effectively allowing the traffic inspector 1023 to continue to monitor for the presence of alarms.

V. Terminology

Many other variations than those described herein will be apparent from this disclosure. For example, depending on the embodiment, certain acts, events, or functions of any of the algorithms described herein can be performed in a different sequence, can be added, merged, or left out all together (e.g., not all described acts or events are necessary for the practice of the algorithms). Moreover, in certain embodiments, acts or events can be performed concurrently, e.g., through multi-threaded processing, interrupt processing, or multiple processors or processor cores or on other parallel architectures, rather than sequentially. In addition, different tasks or processes can be performed by different machines and/or computing systems that can function together.

The various illustrative logical blocks, modules, and algorithm steps described in connection with the embodiments disclosed herein can be implemented as electronic hardware, computer software, or combinations of both. To clearly illustrate this interchangeability of hardware and software, various illustrative components, blocks, modules, and steps have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks and modules described in connection with the embodiments disclosed herein can be implemented or performed by a machine, such as a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A processor can be a hardware processor comprising digital logic circuitry. Further, a processor can be a microprocessor, but in the alternative, the processor can be a controller, microcontroller, or state machine, combinations of the same, or the like. A processor can also be implemented as a combination of hardware computing devices, e.g., a combination of a DSP and a microprocessor, a plurality of microprocessors, one or more microprocessors in conjunction with a DSP core, or any other such configuration. Although described herein primarily with respect to digital technology, a processor may also include primarily analog components. For example, any of the signal processing algorithms described herein may be implemented in analog circuitry. A computing environment can include any type of computer system, including, but not limited to, a computer system based on a microprocessor, a mainframe computer, a digital signal processor, a portable computing device, a personal organizer, a device controller, and a computational engine within an appliance, to name a few.

The steps of a method, process, or algorithm described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, or any other form of non-transitory computer-readable storage medium, media, or physical computer storage known in the art. An example storage medium can be coupled to the processor such that the processor can read information from, and write information to, the storage medium. In the alternative, the storage medium can be integral to the processor. The processor and the storage medium can reside in an ASIC. The ASIC can reside in a user terminal. In the alternative, the processor and the storage medium can reside as discrete components in a user terminal.

Conditional language used herein, such as, among others, "can," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

While the above detailed description has shown, described, and pointed out novel features as applied to various embodiments, it will be understood that various omissions, substitutions, and changes in the form and details of the devices or algorithms illustrated can be made without departing from the spirit of the disclosure. As will be recognized, certain embodiments of the inventions described herein can be embodied within a form that does not provide all of the features and benefits set forth herein, as some features can be used or practiced separately from others.

What is claimed is:

1. A system for remotely escalating a patient monitoring alarm to provide a continuum of care to a patient after discharge from a hospital, the system comprising:
   a memory comprising processor-executable instructions stored thereon, the processor-executable instructions pertaining to alarm escalation; and
   a hardware processor configured to execute the processor-executable instructions pertaining to alarm escalation in response to remotely receiving an alarm and data from a patient monitoring device based on at least one physiological parameter of the patient, the patient monitoring device being assigned to the patient in response to the patient being admitted to the hospital, the hardware processor configured to output an alarm profile template matching attributes of the patient to a clinician and transmit customized alarm settings for the patient to the patient monitoring device in response to acceptance of the alarm profile template by the clinician, wherein the hardware processor is further configured to:
   designate, based on data stored in the memory, first and second care providers who have been previously associated with the patient in the memory, wherein the first care provider is a primary care provider of the patient and the second care provider is a non-primary care provider of the patient;
   electronically determine a situational context of the first care provider;
   in response to determining the situation context of the first care provider indicates the first care provider is available and local to the patient, transmit the alarm to the first care provider for possible in-person intervention;
   in response to determining the situational context of the first care provider indicates the first care provider is available but located remote from the patient, and that the second care provider is local to the patient:
      transmit, to the first care provider, the alarm and data received from the patient monitoring device for interaction with the patient via telepresence technologies;
      electronically receive a recommended course of action from the first care provider regarding the alarm based on the interaction with the patient via telepresence technologies; and
      escalate the alarm by transmitting the recommended course of action and the alarm to the second care provider; and
   in response to determining the situational context of the first care provider indicates that the first care provider is unavailable and that the second care provider is local to the patient, automatically escalate the alarm to the second care provider by transmitting the alarm to the second care provider for possible in-person intervention.

2. The system of claim 1, wherein the hardware processor is further configured to store an alarm setting associated with the patient in a cloud data store.

3. The system of claim 1, wherein the recommended course of action comprises a diagnosis and a medication recommendation.

4. The system of claim 1, wherein the hardware processor is further configured to, prior to receiving the alarm, adjust an alarm setting for the patient.

5. The system of claim 4, wherein adjusting the alarm setting for the patient is based on a received electronic indication that the patient is ambulatory.

6. The system of claim 4, wherein the at least one physiological parameter of the patient comprises a heart rate of the patient.

7. The system of claim 6, wherein adjusting the alarm setting for the patient comprises increasing a heart rate threshold limit at which the alarm occurs.

8. The system of claim 4, wherein adjusting the alarm setting for the patient is based on a health condition of the patient.

9. A system for remotely escalating a patient monitoring alarm to provide a continuum of care to a patient after discharge from a hospital, the system comprising:
   a hardware processor configured to:
      remotely receive an alarm and physiological data from a device monitoring the patient, the device being assigned to the patient in response to the patient being admitted to the hospital, the hardware processor configured to output an alarm profile template matching attributes of the patient to a clinician and transmit customized alarm settings for the patient to the device in response to acceptance of the alarm profile template by the clinician;

designate first and second care providers associated with the patient, wherein the first care provider is a primary care provider of the patient and the second care provider is a non-primary care provider of the patient;

electronically determine a situational context of the first care provider;

in response to determining the situation context of the first care provider indicates the first care provider is available and local to the patient, transmit the alarm to the first care provider for possible in-person intervention;

in response to determining the situational context of the first care provider indicates the first care provider is available but located remote from the patient and that the second care provider is local to the patient:
- transmit, to the first care provider, the alarm and data received from the patient monitoring device for interaction with the patient via telepresence technologies;
- electronically receive a recommended course of action from the first care provider regarding the alarm based on the interaction with the patient via telepresence technologies; and
- escalate the alarm by transmitting the recommended course of action and the alarm to the second care provider; and in response to determining the situational context of the first care provider indicates that the first care provider is unavailable and that the second care provider is local to the patient, automatically escalate the alarm to the second care provider by transmitting the alarm to the second care provider for possible in-person intervention.

10. The system of claim 9, wherein the physiological data comprises one or both of trend data and parameter data.

11. The system of claim 9, wherein the recommended course of action comprises a diagnosis or a medication recommendation.

12. The system of claim 9, wherein the hardware processor is further configured to transmit the recommended course of action and the alarm to a device of the second care provider using video technology.

13. The system of claim 9, wherein the hardware processor is further configured to, prior to receiving the alarm, adjust an alarm setting for the patient.

14. The system of claim 13, wherein adjusting the alarm setting for the patient is based on a received electronic indication that the patient is ambulatory and/or a health condition of the patient.

15. The system of claim 9, wherein the hardware processor is further configured to store an alarm setting associated with the patient in a cloud data store.

16. A method for remotely escalating a patient monitoring alarm to provide a continuum of care to a patient after discharge from a hospital, the method comprising:

remotely receiving an alarm and physiological data from a device monitoring the patient, the device being assigned to the patient in response to the patient being admitted to the hospital, an alarm profile template matching attributes of the patient being outputted to a clinician and customized alarm settings for the patient being transmitted to the device in response to acceptance of the alarm profile template by the clinician;

designating, based on data stored in a memory of an alarm escalation system, first and second care providers who have been previously associated with the patient in the memory, wherein the first care provider is a primary care provider of the patient and the second care provider is a non-primary care provider of the patient, the primary care provider being more familiar with a medical history of the patient than the non-primary care provider;

electronically determining a situational context of the first care provider;

in response to determining the situation context of the first care provider indicates the first care provider is available and local to the patient, transmit the alarm to the first care provider for possible in-person intervention;

in response to determining the situational context of the first care provider indicates the first care provider is available but located remote from the patient, and that the second care provider is local to the patient:
- transmitting, to the first care provider, the alarm and data received from the patient monitoring device for interaction with the patient via telepresence technologies;
- electronically receiving a recommended course of action from the first care provider regarding the alarm based on the interaction with the patient via telepresence technologies; and
- escalating the alarm by transmitting the recommended course of action and the alarm to the second care provider; and in response to determining the situational context of the first care provider indicates that the first care provider is unavailable and that the second care provider is local to the patient, automatically escalating the alarm to the second care provider by transmitting the alarm to the second care provider for possible in-person intervention.

17. The method of claim 16, further comprising, prior to receiving the alarm, adjusting an alarm setting for the patient based on an electronic indication that the patient is ambulatory.

18. The method of claim 16, wherein said transmitting the recommended course of action and the alarm to the second care provider comprises using the telepresence technologies.

19. The system of claim 1, wherein the patient monitoring device is outfitted on the patient upon discharge from the hospital for monitoring of the patient.

20. The system of claim 1, wherein, in response to the clinician not accepting the alarm profile template, the hardware processor is configured to output options for the clinician to modify the alarm profile template.

* * * * *